United States Patent
Lai et al.

(10) Patent No.: US 11,884,707 B2
(45) Date of Patent: Jan. 30, 2024

(54) COMPOSITIONS FOR DETECTION, INHIBITION AND IMAGING OF INDOLEAMINE 2, 3-DIOXYGENASE 1 (IDO1) AND METHODS OF MAKING AND USING SAME

(71) Applicant: Regeneron Pharmaceuticals, Inc., Tarrytown, NY (US)

(72) Inventors: Bert Tsunyin Lai, Culver City, CA (US); Heather Dawn Agnew, Culver City, CA (US)

(73) Assignee: REGENERON PHARMACEUTICALS, INC., Tarrytown, NY (US)

(*) Notice: Subject to any disclaimer, the term of this patent is extended or adjusted under 35 U.S.C. 154(b) by 569 days.

(21) Appl. No.: 15/721,512

(22) Filed: Sep. 29, 2017

(65) Prior Publication Data
US 2018/0355003 A1    Dec. 13, 2018

Related U.S. Application Data

(60) Provisional application No. 62/401,655, filed on Sep. 29, 2016.

(51) Int. Cl.
*C07K 14/47*    (2006.01)
*G01N 33/50*    (2006.01)
(Continued)

(52) U.S. Cl.
CPC ............... *C07K 14/47* (2013.01); *C07K 7/06* (2013.01); *C07K 19/00* (2013.01); *G01N 33/50* (2013.01);
(Continued)

(58) Field of Classification Search
CPC ............ A61K 2300/00; A61K 39/3955; A61K 31/381; A61K 31/437; A61K 8/64;
(Continued)

(56) References Cited

U.S. PATENT DOCUMENTS

| 4,899,755 A | 2/1990 | Lauffer et al. |
| 5,021,556 A | 6/1991 | Srinivasan et al. |

(Continued)

FOREIGN PATENT DOCUMENTS

| EP | 2719706 | 4/2014 |
| WO | 8606605 A1 | 11/1986 |

(Continued)

OTHER PUBLICATIONS

Alexander et al. (1998) "Intracranial black-blood MR angiography with high-resolution 3D fast spin echo," Magnetic Resonance in Medicine. 40(2):298-310.

(Continued)

*Primary Examiner* — Aradhana Sasan
*Assistant Examiner* — Jia-Hai Lee
(74) *Attorney, Agent, or Firm* — PABST PATENT GROUP LLP

(57) ABSTRACT

The present application provides stable peptide-based IDO1 capture agents and methods of use as detection, imaging, diagnostic and therapeutic agents. The application further provides methods of manufacturing IDO1 imaging agents.

26 Claims, 21 Drawing Sheets
Specification includes a Sequence Listing.

(51) Int. Cl.
| | |
|---|---|
| *C07K 7/06* | (2006.01) |
| *C07K 19/00* | (2006.01) |
| *G01N 33/53* | (2006.01) |
| *G01N 33/534* | (2006.01) |
| *G01N 33/573* | (2006.01) |
| *G01N 33/60* | (2006.01) |
| *G01N 33/68* | (2006.01) |
| *A61K 38/00* | (2006.01) |

(52) U.S. Cl.
CPC ....... *G01N 33/534* (2013.01); *G01N 33/5306* (2013.01); *G01N 33/573* (2013.01); *G01N 33/60* (2013.01); *G01N 33/68* (2013.01); *A61K 38/00* (2013.01); *C07K 2319/01* (2013.01); *C07K 2319/60* (2013.01); *C07K 2319/70* (2013.01)

(58) Field of Classification Search
CPC ........ A61K 31/4192; A61K 2039/6031; A61K 47/30; A61K 47/42; A61K 49/0056; A61P 35/00; C12Q 1/6886; C07D 249/04; C07D 403/04; C07D 285/10; C07D 405/04; C12N 15/1137; G01N 2800/52; G01N 33/57484; G01N 33/574; G01N 2333/4703; C12Y 113/11052; C12Y 113/11011; C12Y 113/11017
See application file for complete search history.

(56) References Cited

U.S. PATENT DOCUMENTS

| | | | |
|---|---|---|---|
| 5,075,099 | A | 12/1991 | Srinivasan et al. |
| 5,118,797 | A | 6/1992 | Jurisson et al. |
| 5,183,653 | A | 2/1993 | Linder et al. |
| 5,364,613 | A | 11/1994 | Sieving et al. |
| 5,367,080 | A | 11/1994 | Toner et al. |
| 5,387,409 | A | 2/1995 | Nunn et al. |
| 5,474,756 | A | 12/1995 | Tweedle et al. |
| 5,547,668 | A | 8/1996 | Kranz |
| 5,608,110 | A | 3/1997 | Ramalingam et al. |
| 5,656,254 | A | 8/1997 | Ramalingam et al. |
| 5,662,885 | A | 9/1997 | Pollak et al. |
| 5,665,329 | A | 9/1997 | Ramalingam et al. |
| 5,688,487 | A | 11/1997 | Linder et al. |
| 5,720,934 | A | 2/1998 | Dean et al. |
| 5,780,006 | A | 7/1998 | Pollak et al. |
| 5,846,519 | A | 12/1998 | Tweedle et al. |
| 5,849,261 | A | 12/1998 | Dean et al. |
| 5,879,658 | A | 3/1999 | Dean et al. |
| 5,886,142 | A | 3/1999 | Thakur et al. |
| 5,976,495 | A | 11/1999 | Pollak et al. |
| 6,093,382 | A | 7/2000 | Wedeking et al. |
| 6,143,274 | A | 11/2000 | Tweedle et al. |
| 6,566,088 | B1 | 5/2003 | McKnight |
| 8,710,180 | B2 | 4/2014 | Pitram |
| 8,841,083 | B2 | 9/2014 | Heath |
| 8,906,830 | B2 | 12/2014 | Agnew |
| 9,188,584 | B2 | 11/2015 | Agnew |
| 9,221,889 | B2 | 12/2015 | Pitram |
| 9,239,332 | B2 | 1/2016 | Heath |
| 9,913,875 | B2 | 3/2018 | Farrow |
| 10,017,540 | B2 | 7/2018 | Henning |
| 10,598,671 | B2 | 3/2020 | Heath |
| 10,913,774 | B2 | 2/2021 | Henning |
| 11,007,245 | B2 | 5/2021 | Farrow |
| 2006/0153839 | A1 | 7/2006 | Mohamed |
| 2010/0009896 | A1 | 1/2010 | Agnew et al. |
| 2011/0177109 | A1 | 7/2011 | Smith, III |
| 2011/0263515 | A1 | 10/2011 | Agnew |
| 2012/0202219 | A1 | 8/2012 | Agnew |
| 2012/0252071 | A1 | 10/2012 | Grief |
| 2014/0302998 | A1 | 10/2014 | Heath |
| 2015/0099658 | A1 | 4/2015 | Pfeilsticker |
| 2015/0132314 | A1 | 5/2015 | Masternak |
| 2015/0344523 | A1 | 12/2015 | Deyle |
| 2016/0264627 | A1 | 9/2016 | Henning |
| 2016/0331800 | A1 | 11/2016 | Farrow |
| 2017/0319722 | A1 | 11/2017 | Agnew |
| 2018/0364253 | A1 | 12/2018 | Agnew |
| 2020/0407712 | A1 | 12/2020 | Boyd |
| 2022/0211648 | A1 | 7/2022 | Agnew |

FOREIGN PATENT DOCUMENTS

| | | | |
|---|---|---|---|
| WO | 9103200 | A1 | 3/1991 |
| WO | 9503280 | A1 | 2/1995 |
| WO | 9506633 | A1 | 3/1995 |
| WO | 9528179 | A1 | 10/1995 |
| WO | 9528967 | A1 | 11/1995 |
| WO | 9603427 | A1 | 2/1996 |
| WO | 9623526 | A2 | 8/1996 |
| WO | 9736619 | A2 | 10/1997 |
| WO | 1998/018496 | | 5/1998 |
| WO | 9818496 | A2 | 5/1998 |
| WO | 9818497 | A2 | 5/1998 |
| WO | 1998018496 | | 5/1998 |
| WO | 9846612 | A1 | 10/1998 |
| WO | 9852618 | A1 | 11/1998 |
| WO | 9917809 | A2 | 4/1999 |
| WO | 99/21576 | | 5/1999 |
| WO | 9921576 | | 5/1999 |
| WO | 02/083064 | | 10/2002 |
| WO | 02083064 | | 10/2002 |
| WO | 03/006620 | | 1/2003 |
| WO | 03006620 | | 1/2003 |
| WO | 2005/113762 | | 12/2005 |
| WO | 2005113762 | | 12/2005 |
| WO | 2007/050963 | | 5/2007 |
| WO | 2007050963 | | 5/2007 |
| WO | 2009/051555 | | 4/2009 |
| WO | 2009051555 | | 4/2009 |
| WO | 2009/105746 | | 8/2009 |
| WO | 2009105746 | | 8/2009 |
| WO | 2009/155420 | | 12/2009 |
| WO | 2009155420 | | 12/2009 |
| WO | 2010/135431 | | 11/2010 |
| WO | 2010135431 | | 11/2010 |
| WO | 2011/057347 | | 5/2011 |
| WO | 2011057347 | | 5/2011 |
| WO | 2012/106651 | | 8/2012 |
| WO | 2012106651 | | 8/2012 |
| WO | 2012106671 | A1 | 8/2012 |
| WO | 2013009869 | A2 | 1/2013 |
| WO | 2013033561 | A1 | 3/2013 |
| WO | WO2013034982 | A2 * | 3/2013 ............. A61K 38/08 |
| WO | 2014/056813 | | 4/2014 |
| WO | 2014056813 | | 4/2014 |
| WO | 2014074907 | A1 | 5/2014 |
| WO | 2014/205317 | | 12/2014 |
| WO | 2014205317 | | 12/2014 |
| WO | WO2016038565 | A1 * | 3/2016 ........... C07K 14/655 |
| WO | 2017/011769 | | 1/2017 |
| WO | 2017/176769 | | 1/2017 |
| WO | 2017011769 | | 1/2017 |
| WO | 2017176769 | | 10/2017 |
| WO | 2018/064597 | | 4/2018 |
| WO | 2018064597 | | 4/2018 |
| WO | 2018/111580 | | 6/2018 |
| WO | 2018111580 | | 6/2018 |
| WO | 2018/170096 | | 9/2018 |
| WO | 2018170096 | | 9/2018 |
| WO | 2018/200551 | | 11/2018 |
| WO | 2018200551 | | 11/2018 |
| WO | 2020/127227 | | 6/2020 |
| WO | 2020127227 | | 6/2020 |

OTHER PUBLICATIONS

Altschul et al. (1997) "Gapped BLAST and PSI-BLAST: a new generation of protein database search programs," Nucleic Acids Research. 25(17):3389-3402.

(56) References Cited

OTHER PUBLICATIONS

Claverie et al. (1993) "Information enhancement methods for large scale sequence analysis," Computers & Chemistry. 17(2):191-201.
Edelman et al. (1990) "Extracranial carotid arteries: evaluation with 'black blood' MR angiography," Radiology. 177(1):45-50.
Goodrich et al. (1996) "A quantitative study of ramped radio frequency, magnetization transfer, and slab thickness in three-dimensional time-of-flight magnetic resonance angiography in a patient population," Investigative Radiology. 31(6):323-332.
Iwata et al. (2000) "A new, convenient method for the preparation of 4-[18 F] fluorobenzyl halides," Applied Radiation and Isotopes. 52(1):87-92.
Liu et al. (1999) "99mTc-labeled small peptides as diagnostic radiopharmaceuticals," Chemical Reviews. 99(9):2235-2268.
Meyers et al. (1988) "Optimal Alignments in Linear Space," Computer Applic. Biol. Sci. 4(1):11-17.
Poethko et al. (2004) "Two-step methodology for high-yield routine radiohalogenation of peptides: 18F-labeled RGD and octreotide analogs," Journal of Nuclear Medicine. 45(5):892-902.
Schottelius et al. (2004) "First 18F-labeled tracer suitable for routine clinical imaging of sst receptor-expressing tumors using positron emission tomography," Clinical Cancer Research. 10(11):3593-3606.
Wilson et al. (1990) "Reductive Amination of [18F]Fluorobenzaldehydes: Readiosyntheses of [2-18F]-and [4-18F] Fluorodexetimides," Journal of Labeled Compounds and Radiopharmaceuticals. XXVIII(10):1189-1199.
Wootton et al. (1993) "Statistics of local complexity in amino acid sequences and sequence databases," Computers & Chemistry 17(2):149-163.
Agnew, et al., "Protein-Catalyzed Capture Agents", *Chemical Reviews*, 119(17):9950-9970 (2019).
Agnew, et al., "Iterative In Situ Click Chemistry Creates Antibody-like Protein-Capture Agents", *Angew. Chem. Int. Ed. Engl.*, 48(27):4944-4948 (2009).
Artali, et al., "A molecular dynamics study of human serum albumin binding sites", *Il Farmaco*, 60:485-495 (2005).
Bianchi et al., "Vaccination with peptide mimetics of the gp41 prehairpin fusion intermediate yields neutralizing antisera against HIV-1 isolates", *PNAS*, 107(23):10655-10660 (2010).
Boersma, "Gaining knowledge of single carbon chains", *Theory of condensed matter, Radboud Univ. Nijmegen*, 18 pages (2011).
Chan, et al., "Dual-targeting anti-angiogenic cyclic peptides as potential drug leads for cancer therapy", *Scientific Reports*, 6:35247, 13 pages (2016).
Chattopadhyay, et al., "Techniques to improve the direct ex vivo detection of low frequency antigen-specific CD8+ T cells with peptide-major histocompatibility complex class I tetramers", *Cytometry Part A*, 73(11): 1001-1009 (2008).
Chauhan, et al. "The Taming of the Cell Penetrating Domain of the HIV Tat: Myths and Realities", *J. Control Release*, 117(2): 148-162 (2007).
Chen, et al., "Fusion protein linkers: property, design and functionality", *Adv. Drug Deliv. Rev.*, 65(10): 1357-1369 (2013).
Cheong, et al., "A patent review of IDO1 inhibitors for cancer", *Expert Opinion on Therapeutic Patents*, 28(4):317-330 (2018).
Choksi, et al., "A CD8 DE loop peptide analog prevents graft-versus-host disease in a multiple minor histocompatibility antigen-mismatched bone marrow transplantation model", *Biology of Blood and Marrow Transplantation*, 10(10):669-680 (2004).
Coppock, et al., "Peptide-based protein capture agents with high affinity, selectivity, and stability as antibody replacements in bio detection assays", *Proc. of SPIE*, 9107:910711-1 (2014).
Das, et al., "A General Synthetic Approach for Designing Epitope Targeted Macrocyclic Peptide Ligands", *Angew. Chemie Int. Ed. Engl.*, 54(45):13219-24 (2015).
Dieck, et al., "Development of bispecific molecules for the in-situ detection of protein-protein interactions and protein phosphorylation", *Cell & Biology*, 21:357-368 (2014).

Eiber, et al., "Prostate-Specific Membrane Antigen Ligands for Imaging and Therapy", *The Journal of Nuclear Medicine*, 58(Supplement 2):67S-76S (2017).
Farrow, et al., "Epitope Targeting of Tertiary Protein Structure Enables Target-Guided Synthesis of a Potent In-Cell Inhibitor of Botulinum Neurotoxin", *Angew Chem Int Ed Engl.*, 54(24): 7114-7119 (2015).
Fisher, et al, "Trivalent Gd-DOTA reagents for modification of proteins", *RSC Adv.*, 5: 96194-96200 (2015).
Fitzer-Attas, et al., "Harnessing Syk family tyrosine kinases as signaling domains for chimeric single chain of the Variable Domain Receptors: Optimal Design for T Cell Activation", *J. Immunol.*, 160(1):145-154 (1998).
Gao, et al., "Crystal structure of the complex between human CD8alpha(alpha) and HLA-A2", *Nature*, 387:630-4 (1997).
Gen Bank: AAH25715.1, "CD8a molecule [*Homo sapiens*]" retrieved from the internet Jun. 17, 2022.
Handl, et al., "Hitting multiple targets with multimeric ligands", *Expert Opin. Ther. Targets*, 8(6):565-586 (2004).
Hill, et al., "Constraining Cyclic Peptides to Mimic Protein Structure Motifs", *Angewandte Chemie*, 53(48):13020-13041 (2014).
Hirai, et al., "MK-2206, an Allosteric Akt Inhibitor, Enhances Antitumor Efficacy by Standard Chemotherapeutic Agents or Molecular Targeted Drugs In vitro and In vivo", *Molecular Cancer Therapeutics*, 9(7): 1956-1967 (2010).
Hudson, et al, "Multiplex epitope mapping using bacterial surface display reveals both linear and conformational epitopes", *Scientific Reports*, 2(706):1-9 (2012).
Josan, et al., "Cell-specific targeting by heterobivalent ligands", *Bioconjug Chem.*, 22(7): 1270-1278 (2011).
Lai, et al., "Epitope-Targeted Macrocyclic Peptide Ligand with Picomolar Cooperative Binding to Interleukin-17F", *Chemistry*, 24(15):3760-3767 (2018).
Li, et al., "Identification of the CD8 DE loop as a surface functional epitope. Implications for major histocompatibility complex class 1 binding and CD8 inhibitor design", *Journal Of Biological Chemistry*, 273(26): 16442-16445 (1998).
Lin, et al., "Inhibition of HIV-1 Tat-mediated transcription by a coumarin derivative, BPRHIV001, through the Akt pathway", *Journal of Virology*, 85(17): 9114-9126 (2011).
Lindlsey, et al., "The P13K/Akt Pathway: Recent Progress in the Development of ATP-Competitive and Allosteric Akt Kinase Inhibitors", *Current Cancer Drug Targets*, 8: 7-18 (2008).
Ma, et al., "A cyclic peptide-polymer probe for the detection of Clostridium botulinum neurotoxin serotype A", *Toxicon*, 47(8):901-908 (2006).
Mabry, et al., "Engineering of stable bispecific antibodies targeting IL-17 A and IL-23", *Protein Engineering, Design & Selection*, 23(3):115-127 (2010).
Macraild et al., "Antibody Recognition of Disordered Antigens", *Structure* 24:148-157 (2016).
Macraild et al., "Conformational Dynamics and Antigenicity in the Disordered Malaria Antigen Merozoite Surface Protein 2", *PLOS One*, 13 pages (2015).
Mamidyala et al., In situ click chemistry: probing the binding landscapes of biological molecules, *Chemical Society Reviews*, 39(4):1252-1261 (2010).
Manea, et al., "Antibody Recognition and Conformational Flexibility of a Plaque-Specific-Amyloid Epitope Modulated by Non-native Peptide Flanking Regions", *J. Med. Chem.*, 51(5):1150-1161 (2008).
Matsuura, "Identification of conformational neutralizing epitopes on the capsid protein of canine calicivirus", *Journal of General Virology*, 82:1695-1702 (2001).
Melenhorst et el., "Detection of low avidity CD8(+) T cell populations with coreceptor-enhanced peptide-major histocompatibility complex class I tetramers", *J Immunol Methods*, 338(1-2): 31-39 (2008).
Merriam-Webster online definition of "correspond" downloaded Jun. 29, 2020 from internet, https://www.merriam-webster.com/dictionary/correspond (Year: 2020).
Millward, et al., "In situ click chemistry: from small molecule discovery to synthetic antibodies", *Integr. Biol* (*Camb*)., 5(1): 87-95 (2013).

(56) References Cited

OTHER PUBLICATIONS

Millward, et al., "Iterative in situ click chemistry assembles a branched capture agent and allosteric inhibitor for Akt1", JACS, 133(45):18280-18288 (2011).

Miossec, "Update on interleukin-17: a role in the pathogenesis of inflammatory arthritis and implication for clinical practice", RMD Open, 3(1):e000284 (2017).

Mor, et al., Mimicking the Structure of the V3 Epitope Bound to HIV-1 Neutralizing Antibodies, Biochemistry, 48(15):3288-3303 (2009).

Muller, et al., "DOTA Conjugate with an Albumin-Binding Entity Enables the First Folic Acid-Targeted 177Lu-Radionuclide Tumor Therapy in Mice", The Journal of Nuclear Medicine, 54(1):124-131 (2013).

Muller, et al., "Folic acid conjugates for nuclear imaging of folate receptor-positive cancer", J. Nucl. Med., 52(1): 1-4 (2011).

Nag et al., "A chemical epitope-targeting strategy for protein capture agents: the serine 474 epitope of the kinase Akt2", Angewandte Chemie International Edition, 52:13975-13979 (2013).

O'Shannessy, et al., "Characterization of the human folate receptor alpha via novel antibody-based probes", Oncotarget, 2(12):1227-1243 (2011).

Pansca, et al., "Structural disorder in eukaryotes", PLoS One, www.plosone.org Apr. 1, 2012, 7(4): e34687, 10 pages (2012).

Pfeilsticker, et al., "A cocktail of thermally stable, chemically synthesized capture agents for the efficient detection of anti-gp41 antibodies from human sera", PLoS One, 8(10): Article No. e76224, 5 pages (2013).

Saito, et al., "Identification of anti-CD98 antibody mimotopes for inducing antibodies with antitumor activity by mimotope immunization", Cancer Science, 105(4): 396-401 (2014).

Sarbassov, et al., "Phosphorylation and regulation of Akt/PKB by the rictor-mTOR complex", Science, American Association for The Advancement of Science, 307(5712): 1098-1101 (2005).

Schweinsberg, et al., "Novel glycated [99mTc (CO)3]-labeled bombesin analogues for improved targeting of gastrin-releasing peptide receptor-positive tumors", Bioconjugate Chem., 19(12):2432-2439 (2008).

Son, et al., "New Cyclic Lipopeptides of the Iturin Class Produced by Saltern-Derived Bacillus sp. KCB14S006", Marine Drugs, 14(4): 72 (2016).

Subramanyam, et al., "Inhibition of Protein Kinase Akt1 by Apoptosis Signal-regulating Kinase-1 (ASK1) Is Involved in Apoptotic Inhibition of Regulatory Volume Increase", Journal of Biological Chemistry, 285(9): 6109-6117(2010).

Tang et al., "Chimeric molecules facilitate the degradation of androgen receptors and repress the growth of LNCaP cells", Asian Journal of Andrology, 11(1): 119-126 (2009).

Tao, et al., "Expression, purification and identification of an immunogenic fragment in the ectodomain of prostate-specific membrane antigen", Experimental And Therapeutic Medicine, 11(3): 747-752 (2016).

Todorova, et al., "Biochemical nature and mapping of PSMA epitopes recognized by human antibodies induces after immunization with gene-based vaccines", Anticancer Research, 25: 4727-4732 (2005).

Torres, et al., "A revolutionary therapeutic approach for psoriasis: bi specific biological agents", Expert Opinion on Investigational Drugs, 25(7): 751-754 (2016).

Wang, et al., "Epitope Mapping Using Phage-Display Random Fragment Libraries", Epitope Mapping Protocols, Methods in Molecular Biology, 524: 315-332 (2009). Abstract Only.

Wang, et al., "Radioligand Therapy of Prostate Cancer with a Long-Lasting Prostate-Specific Membrane Antigen Targeting Agent 90 Y-DOTA-EB-MCG", Bioconjugate Chemistry, 29(7): 2309-2315 (2018).

Wooldridge, et al., "Tricks with tetramers: how to get the most from multimeric peptide-MHC", Immunology, 126:147-164 2009 (2009).

Zhang, et al., "Structure and function of interleukin-17 family cytokines", Protein & Cell, 2(1): 26-40 (2011).

Coppock, et al., "Peptide-based protein capture agents with high affinity, selectivity, and stability as antibody replacements in biodetection assays", Optical Sensing 9107:106 (2014).

Fitzer-Attas, et al., "Harnessing Syk family tyrosine kinases as signaling domains for chimeric single chain of the Variable Domain recept", J. Immunol., 160(1):145-154 (1998).

Gen Bank: AAH25715.1 , "CD8a molecule [Homo sapiens]" retrived from the internet Jun. 17, 2022.

Li, et al., "Identification of the CD8 DE loop as a surface functional epitope. Implications for major histocompatibility complex class I binding and CD8 inhibitor design", Journal Of Biological Chemistry, 273(26): 16442-16445 (1998).

Lindsley, et al., "The P13K/Akt Pathway: Recent Progress in the Development of ATP-Competitive and Allosteric Akt Kinase Inhibitors", Current Cancer Drug Targets, 8: 7-18 (2008).

Muller, et al., "DOTA Conjugate with an Albumin-Binding Entity Enables the First Folic Acid-Targeted 177Lu-Radionuclide Tumor Therapy in Mice", The Jour. of Nucl. Med., 54(11):124-131.

Son, et al., "New Cyclic Lipopeptides of the Iturin Class Produced by Saltern-Derived Bacillus sp. KCB14S006", Marine Drugs, 14(4):72 (2016).

Agalave, et al., "Click chemistry: 1,2,3-triazoles as pharmacophores", Chem. Asian J., 6:(10)2696-27018 (2011).

Almehdi, et al., "SARS-CoV-2 spike protein: pathogenesis, vaccines, and potential therapies", Infection, 49: 855-876 (2021).

BPS Bioscience: INCB024360 Analog Data Sheet (2012).

Glaven, et al., "Linking single domain antibodies that recognize different epitopes on the same target", Biosensors, 2:43-56 (2012).

He, et al., "Vaccine design based on 16 epitopes of SARS-CoV-2 spike protein", Journal of Medical Virology, 93:2115-2131 (2021).

Kirszbaum, et al., "The alpha-chain of murine CD8 lacks an invariant Ig-like disulfide bond but contains a unique intrachain loop instead", J. Immunol., 142(11):3931-6 (1989).

Koonin, et al., "Sequence—Evolution—Function: Computational Approaches in Comparative Genomics", Boston: Kluwer Academic; 2003, Chapter 2 Evolutionary Concept in Genetics and Genomics (2003).

Reeck, et al., "'Homolgy' in Proteins and Nucleic Acids: A Terminology Muddle and a Way out of it", Cell, 50:667 (1987).

Smith, et al., "Zinc Mediated Azide-Alkyne Ligation to 1,5- and 1,4,5-Substituted 1,2,3-Triazoles", Org. Lett., 15(18):4826-4829 (2013).

Sormanni, et al., "Rational design of antibodies targeting specific epitopes within intrinsically disordered proteins", PNAS, 112(32):9902-9907 (2015).

Sormanni, et al., "Supporting Information", PNAS, 112(32):1-10 (2015). Supplemental Materials.

Testa, et al., "CD 123 is a membrane biomarker and a therapeutic target in hematologic malignancies", Biomarker Research, 2:4 (2014).

Wang, et al., "Structural basis of the CD8 alpha beta/MHC class I interaction: focused recognition orients CD8 beta to a T cell proximal position", J. Immunol., 183(4):2554-64 (2009).

Yang, et al., "Structural biology of SARS-CoV-2 and implications for therapeutic development", Nature Reviews, 19:685-700 (2021).

\* cited by examiner

FIG. 1A
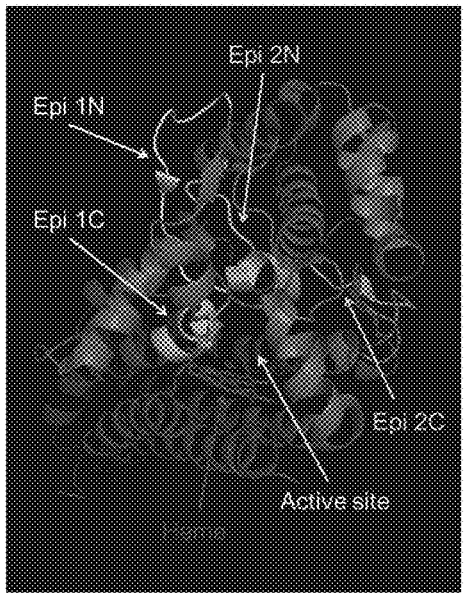
FIG. 1B
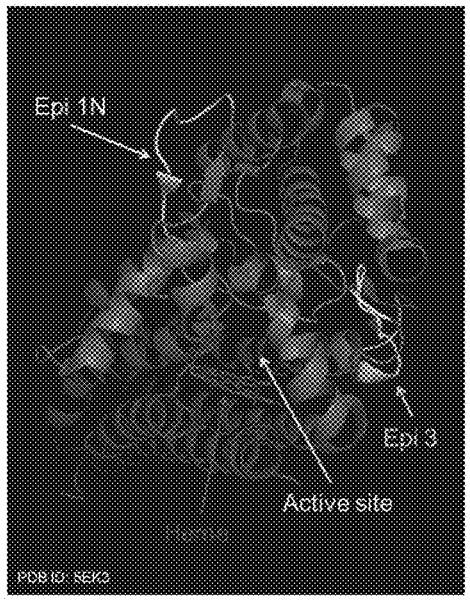
FIG. 1C
| | |
|---|---|
| Mouse IDO1 | GVWDTPKMFSGGSAGQSSIFQ (a.a. 255-275) |
| Human IDO1 | GFWEDPKEFAGGSAGQSSVFQ (a.a. 251-271) |
| Epitope 1 | GFWEDPKE[F→Az4]AGGSAGQSSVFQ |
| | |
| Mouse IDO1 | LPPILSYADCVLANWKKKDPNG (a.a. 124-145) |
| Human IDO1 | LPPILVYADCVLANWKKKDPNK (a.a. 120-141) |
| Epitope 2 | LPPILVYADCV[L→Az4]ANWKKKDPNK |
| | |
| Mouse IDO1 | NGPMTYENMDILFSFP (a.a. 144-159) |
| Human IDO1 | NKPLTYENMDVLFSFR (a.a. 140-155) |
| Epitope 3 | NKPLTYENM[D→Az4]VLFSFR |

FIG. 14A

E1Ctrl      6XHis-PEG-GFWEDPKE<u>F</u>AGGSAGQSSVFQ
Epitope1N   6XHis-PEG-GFWEDPKE<u>F</u>*QAFGVGSSAQGS*
Epitope1C   6XHis-PEG-*EPDFKEWG*<u>F</u>AGGSAGQSSVFQ

FIG. 14B

E2Ctrl      6XHis-PEG-LPPILVYADCV<u>L</u>ANWKKKDPNK
Epitope2N   6XHis-PEG-LPPILVYADCV<u>L</u>*KAKNNPWKKD*
Epitope2C   6XHis-PEG-*LCPDPAIVLY*<u>L</u>ANWKKKDPNK

FIG. 14C

COMPOSITIONS FOR DETECTION, INHIBITION AND IMAGING OF INDOLEAMINE 2, 3-DIOXYGENASE 1 (IDO1) AND METHODS OF MAKING AND USING SAME

RELATED APPLICATION

This application claims priority to U.S. Provisional Patent Application No. 62/401,655, filed on Sep. 29, 2016, the content of which is incorporated herein by reference in its entirety.

SEQUENCE LISTING

The Sequence Listing submitted Aug. 28, 2018 as a text file named "INDI_31_1_US_ST25.txt," created on Jun. 29, 2018, and having a size of 12,964 bytes is hereby incorporated by reference pursuant to 37 C.F.R. § 1.52(e)(5).

BACKGROUND

Anticancer therapies using immune checkpoint inhibitors result in remarkably durable clinical remissions in some patients, while other patients experience a short-term benefit or no benefit at all. The enzyme indoleamine 2,3-dioxygenase 1 (IDO1) is a resistance mechanism in the context of immunotherapies targeting immune checkpoints. IDO1 is a cytosolic protein that causes immunosuppression by breakdown of tryptophan in the tumor microenvironment and tumor-draining lymph nodes. The depletion of tryptophan and accumulation of toxic catabolites renders effector T cells inactive and dendritic cells immunosuppressive. There is a need in the art for IDO1 inhibitors for detecting IDO1 and for preventing IDO1-mediated immunotherapy resistance.

SUMMARY

Provided herein are compositions that specifically bind indoleamine 2,3-dioxygenase 1 (IDO1).

In one aspect, provided herein is a composition that specifically binds indoleamine 2,3-dioxygenase 1 (IDO1) comprising a first ligand having affinity for an epitope on IDO1, wherein the ligand comprises a 5-10 amino acid sequence of D-amino acids and artificial amino acids and wherein IDO1 comprises an active site.

In an embodiment, the epitope comprises 8 to 30 amino acids.

In an embodiment, the epitope is located within 38 Å of the IDO1 active site.

In an embodiment, the ligand comprises 5 to 9 amino acids.

In an embodiment, the ligand comprises a small molecule inhibitor. In certain embodiments, the small molecule inhibitor is an inhibitor of IDO1 enzymatic activity.

In an embodiment, the ligand comprises a 1-methyl-tryptophan (Me-Trp) moiety.

In an embodiment, the epitope comprises the amino acid sequence GFWEDPKEFAGGSAGQSSVFQ (SEQ ID NO: 1). In an embodiment, the ligand comprises an amino acid sequence selected from the group consisting of X1rf(Me-Trp)X2, wherein X1 and X2 are independently D-Ala, D-Arg, D-Asn, D-Asp, D-Glu, Gly, D-His, D-Leu, D-Lys, D-Phe, D-Pro, D-Ser, D-Thr, D-Trp, D-Tyr, or D-Val or is not present, nsfr(Me-Trp), and wyrX3y, wherein X3 is D-Ala or is not present. In other embodiments, the ligand comprises an amino acid sequence selected from the group consisting of frf(Me-Trp)s, arf(Me-Trp)s, rf(Me-Trp)s, frf(Me-Trp)a, frf(Me-Trp), and rf(Me-Trp). In other embodiments, the ligand comprises an amino acid sequence of wyray or wyry.

In an embodiment, the epitope comprises the amino acid sequence LPPILVYADCVLANWKKKDPNK (SEQ ID NO: 2). In an embodiment, the ligand comprises an amino acid sequence selected from the group consisting of rys(Me-Trp)r, X4lf(Me-Trp)(F-Phe), wherein X4 is D-Ala, D-Arg, D-Asn, D-Asp, D-Glu, Gly, D-His, D-Leu, D-Lys, D-Phe, D-Pro, D-Ser, D-Thr, D-Trp, D-Tyr, or D-Val or is not present, nlw(Me-Trp)r, and sX5ww(F-Phe), wherein X5 is D-Ala, D-Arg, D-Asn, D-Asp, D-Glu, Gly, D-His, D-Leu, D-Lys, D-Phe, D-Pro, D-Ser, D-Thr, D-Trp, D-Tyr, or D-Val or is not present. In other embodiments, the ligand comprises an amino acid sequence of nlf(Me-Trp)(F-Phe), alf(Me-Trp)(F-Phe), or lf(Me-Trp)(F-Phe). In other embodiments, the ligand comprises an amino acid sequence of spww(F-Phe), saww(F-Phe), or sww(F-Phe).

In an embodiment, the epitope comprises the amino acid sequence NKPLTYENMDVLFSFR (SEQ ID NO: 3). In an embodiment, the ligand comprises an amino acid sequence selected from the group consisting of rffyl and nsh(F-Phe)r.

In an embodiment, the composition further comprises a small molecule that inhibits the activity of IDO1. In an embodiment, the small molecule that inhibits the activity of IDO1 is covalently attached to the ligand.

In an aspect, provided herein is a composition that specifically binds IDO1, wherein the composition comprises a first ligand having affinity for a first epitope on IDO1, a second ligand having affinity for a second epitope on IDO1, and a linker covalently connecting the first ligand to the second ligand, wherein the first and second ligands comprise 5-10 amino acid sequences of D-amino acids and artificial amino acids and wherein IDO1 comprises an active site.

In an embodiment, the first and second epitopes independently comprise 8 to 30 amino acids.

In an embodiment, the first and second epitopes are located within 38 Å of the IDO1 active site.

In an embodiment, the first and second ligands independently comprise 5 to 9 amino acids.

In an embodiment, at least one of the first and second ligands comprises a Me-Trp moiety.

In an embodiment, the first epitope and the second epitope are distinct from each other and comprise an amino acid sequence selected from the group consisting of GFWEDPKEFAGGSAGQSSVFQ (SEQ ID NO: 1), LPPILVYADCVLANWKKKDPNK (SEQ ID NO: 2), and NKPLTYENMDVLFSFR (SEQ ID NO: 3). In an embodiment, the first ligand and the second ligand each bind the first or the second epitope and comprise an amino acid sequence selected from the group consisting of X1rf(Me-Trp)X2, wherein X1 and X2 are independently D-Ala, D-Arg, D-Asn, D-Asp, D-Glu, Gly, D-His, D-Leu, D-Lys, D-Phe, D-Pro, D-Ser, D-Thr, D-Trp, D-Tyr, or D-Val or is not present, nsfr(Me-Trp), wyrX3y, wherein X3 is D-Ala or is not present, rys(Me-Trp)r, X4lf(Me-Trp)(F-Phe), wherein X4 is D-Ala, D-Arg, D-Asn, D-Asp, D-Glu, Gly, D-His, D-Leu, D-Lys, D-Phe, D-Pro, D-Ser, D-Thr, D-Trp, D-Tyr, or D-Val or is not present, nlw(Me-Trp)r, sX5ww(F-Phe), wherein X5 is D-Ala, D-Arg, D-Asn, D-Asp, D-Glu, Gly, D-His, D-Leu, D-Lys, D-Phe, D-Pro, D-Ser, D-Thr, D-Trp, D-Tyr, or D-Val or is not present, rffyl, and nsh(F-Phe)r. In other embodiments, the ligand comprises an amino acid sequence selected from the group consisting of frf(Me-Trp)s, arf (Me-Trp)s, rf(Me-Trp)s, frf(Me-Trp)a, frf(Me-Trp), and rf(Me-Trp). In other embodiments, the ligand comprises an amino acid sequence of wyray or wyry. In other embodiments, the ligand comprises an amino acid sequence of nlf(Me-Trp)(F-Phe), alf(Me-Trp)(F-Phe), or lf(Me-Trp)(F-Phe). In other embodiments, the ligand comprises an amino acid sequence of spww(F-Phe), saww(F-Phe), or sww(F-Phe).

In an embodiment, either the first ligand or the second ligand comprises a 1,4-substituted-1,2,3-triazole residue (Tz4) or a 1,5-substituted-1,2,3-triazole residue (Tz5). In an embodiment, the triazole residue is a 1,4-substituted-1,2,3-triazole (Tz4) residue.

In an embodiment, the length of the linker corresponds to the distance between the first epitope and the second epitope. In an embodiment, the length of the linker is from about 11 Å to about 38 Å.

In an embodiment, the composition further comprises a detectable moiety. In an embodiment, the detectable moiety is selected from the group consisting of biotin, copper-DOTA, biotin-PEG$_3$, aminooxyacetate, $^{19}$FB, $^{18}$FB, and FITC-PEG$_3$. In an embodiment, the detectable moiety is selected from the group consisting of $^{64}$Cu DOTA, $^{68}$Ga DOTA, $^{68}$Ga NOTA, $^{18}$F, Al$^{18}$F NOTA, $^{64}$Cu, $^{68}$Ga, $^{89}$Zr, $^{124}$I, $^{86}$Y, $^{94m}$Tc, $^{110m}$In, $^{11}$C and $^{76}$Br. In an embodiment, the detectable moiety is $^{18}$F.

In another aspect, provided herein is a method of detecting IDO1 in a biological sample, comprising contacting the biological sample with one or more compositions of any one of the previous claims.

In an embodiment, the method further comprises binding IDO1 to said one or more composition, and detecting the detectable moiety linked to said one or more imaging agents.

In another aspect, provided herein is a method of identifying a composition that specifically binds to a target protein, wherein the composition comprises a 5-10 amino acid sequence of D-amino acids and artificial amino acids, comprising contacting an epitope of the target protein to a library of molecules wherein the members of the library comprise distinct peptides of 5-10 amino acids, wherein the amino acids are D-amino acids or artificial amino acids, and wherein the epitope of the target protein comprises 8-30 amino acids and comprises an azide click handle; covalently binding members of the library that specifically bind to the epitope to the azide click handle; and identifying the amino acid sequence of the library members that covalently bind to the epitope.

In an embodiment, the target protein is IDO1.

In an embodiment, the epitope of IDO1 comprises an amino acid sequence with one substitution from a sequence selected from the group consisting of GFWEDPKEFAGGSAGQSSVFQ (SEQ ID NO: 1), LPPILVYADCVLANWKKKDPNK (SEQ ID NO: 2), and NKPLTYENMDVLFSFR (SEQ ID NO: 3).

In an embodiment, the epitope of IDO1 comprises an amino acid sequence selected from the group consisting of GFWEDPKEAz4AGGSAGQSSVFQ (SEQ ID NO: 4), LPPILVYADCVAz4ANWKKKDPNK (SEQ ID NO: 5), and NKPLTYENMAz4VLFSFR (SEQ ID NO: 6).

In another aspect, provided herein is a method of treating a cancer in a subject in need thereof comprising administering a therapeutically effective amount of a composition that specifically binds IDO1 comprising a first ligand having affinity for an epitope on IDO1, wherein the ligand comprises a 5-10 amino acid sequence of D-amino acids and artificial amino acids and wherein IDO1 comprises an active site, thereby treating the cancer.

In another aspect, provided herein is a method of reducing IDO1 enzymatic activity comprising contacting IDO1 with an effective amount of a composition that specifically binds IDO1, wherein the composition comprises a first ligand having affinity for a first epitope on IDO1, a second ligand having affinity for a second epitope on IDO1, and a linker covalently connecting the first ligand to the second ligand, wherein the first and second ligands comprise 5-10 amino acid sequences of D-amino acids and artificial amino acids, thereby reducing IDO1 enzymatic activity.

In another aspect, provided herein is a method of detecting IDO1 comprising contacting IDO1 with an effective amount of a composition that specifically binds IDO1, wherein the composition comprises a first ligand having affinity for a first epitope on IDO1, a second ligand having affinity for a second epitope on IDO1, and a linker covalently connecting the first ligand to the second ligand, wherein the first and second ligands comprise 5-10 amino acid sequences of D-amino acids and artificial amino acids. In certain embodiments, the IDO1 to be detected is located in the cytosol of an intact cell.

BRIEF DESCRIPTION OF THE DRAWINGS

FIGS. 1A, 1B, and 1C: Epitopes derived from the IDO1 protein. FIG. 1A. Crystal structure of human IDO1 with Epitopes 1 and 2, the heme group and active site shown. FIG. 1B. Crystal structure of human IDO1 with Epitopes 1N and 3 shown. FIG. 1C. Sequences of the designed IDO1 epitopes. An azide click handle (Az4) is substituted at the bracketed amino acid positions (SEQ ID NOs: 10, 1, 11, 12, 2, 13, 14, 3 and 15, respectively, in order of appearance).

FIG. 3A. Chemical Structure. FIG. 3B. Sandwich ELISA for human IDO1 protein against biotin-PEG$_3$-modified Cy(frf(Me-Trp)s) yields EC$_{50}$ value of 20 nM.

FIG. 4A. Chemical Structure. FIG. 4B. Sandwich ELISA for human IDO1 protein against biotin-PEG$_3$-modified Cy(nsfr(Me-Trp)) yields EC$_{50}$ value of 124 nM.

FIG. 5A. Chemical Structure. FIG. 5B. Sandwich ELISA for human IDO1 protein against biotin-PEG$_3$-modified Cy(rys(Me-Trp)r) yields EC$_{50}$ value of 81 nM. A solution of 200 nM macrocycle was immobilized in this assay.

FIG. 6A. Chemical Structure. FIG. 6B. Sandwich ELISA for human IDO1 protein against biotin-PEG$_3$-modified Cy(nlf(Me-Trp)(F-Phe)) yields EC$_{50}$ value of 20 nM.

FIG. 7A. Chemical Structure. FIG. 7B. Sandwich ELISA for human IDO1 protein against biotin-PEG$_3$-modified Cy(nlw (Me-Trp)r) yields EC$_{50}$ value of 43 nM.

FIG. 8A. Chemical Structure. FIG. 8B. Sandwich ELISA for human IDO1 protein against biotin-PEG$_3$-modified Cy(spww(F-Phe)) yields EC$_{50}$ value of 65 nM.

FIG. 9A. Chemical Structure. FIG. 9B. Sandwich ELISA for human IDO1 protein against biotin-PEG$_3$-modified Cy(rffyl) yields EC$_{50}$ value of 125 nM.

FIG. 10A. Chemical Structure. FIG. 10B. Sandwich ELISA for human IDO1 protein against biotin-PEG$_3$-modified Cy(nsh(F-Phe)r) yields EC$_{50}$ value of 68 nM.

FIG. 11A. Chemical Structure. FIG. 11B. Sandwich ELISA for human IDO1 protein against biotin-PEG$_3$-modified Cy(wyray) yields EC$_{50}$ value of 25 nM.

FIG. 12A. Binding affinities for frf(Me-Trp)s. FIG. 12B. Binding affinities for rys(Me-Trp)r. FIG. 12C. Binding affinities for nlf(Me-Trp)(F-Phe). FIG. 12D. Binding affinities for nlw(Me-Trp)r. FIG. 12E. Binding affinities for spww(F-Phe). FIG. 12F. Binding affinities for wyray. FIG. 12G. Binding affinities for rffyl. FIG. 12H. Binding affinities for nsh(F-Phe)r.

FIG. 13A. Structure of INCB024360 analogue. FIG. 13B. Recombinant human IDO1 inhibition data for INCB024360 analogue compared to macrocycles frf(Me-Trp)s, spww(F-Phe), and rys(Me-Trp)r.

FIGS. 14A, 14B, 14C, 14D, and 14E: Orientation of macrocycle binding to IDO1 Epitopes 1 and 2. FIG. 14A. 6×His-tagged variants of IDO1 Epitope1 (SEQ ID NOs: 16-18, respectively, in order of appearance) were synthesized to contain strategic scrambling of the sequences either N-terminal or C-terminal to the location of the click handle (F259). FIG. 14B. Similarly, 6×His-tagged variants of IDO1 Epitope2 (SEQ ID NOs: 19-21, respectively, in order of appearance) were synthesized to contain strategic scrambling of the sequences either N-terminal or C-terminal to L131. Regions of scrambled sequence are shown in italics. FIG. 14C. Point ELISA for the 6×His-tagged IDO1 epitopes against frf(Me-Trp)s ("6×His" disclosed as SEQ ID NO: 7). FIG. 14D. Point ELISA for the 6×His-tagged IDO1 epitopes against nlw(Me-Trp)r ("6×His" disclosed as SEQ ID NO: 7). FIG. 14E. Point ELISA for the 6×His-tagged IDO1 epitopes against spww(F-Phe) ("6×His" disclosed as SEQ ID NO: 7).

FIG. 15A. Alanine scan of macrocycle to determine amino acids critical to IDO1 binding. FIG. 15B. Smaller macrocycles (3-mer and 4-mer) to compare ring size and IDO1 binding.

FIG. 16A. Alanine scan of macrocycle to determine amino acids critical to IDO1 binding. FIG. 16B. Smaller macrocycles (4-mer) to compare ring size and IDO1 binding.

FIG. 17A. Alanine scan of macrocycle to determine amino acids critical to IDO1 binding. FIG. 17B. Smaller macrocycles (3-mer and 4-mer) to compare ring size and IDO1 binding.

FIG. 18A. Alanine scan of macrocycle to determine amino acids critical to IDO1 binding. FIG. 18B. Smaller macrocycles (4-mer) to compare ring size and IDO1 binding.

DETAILED DESCRIPTION

Figure 2:
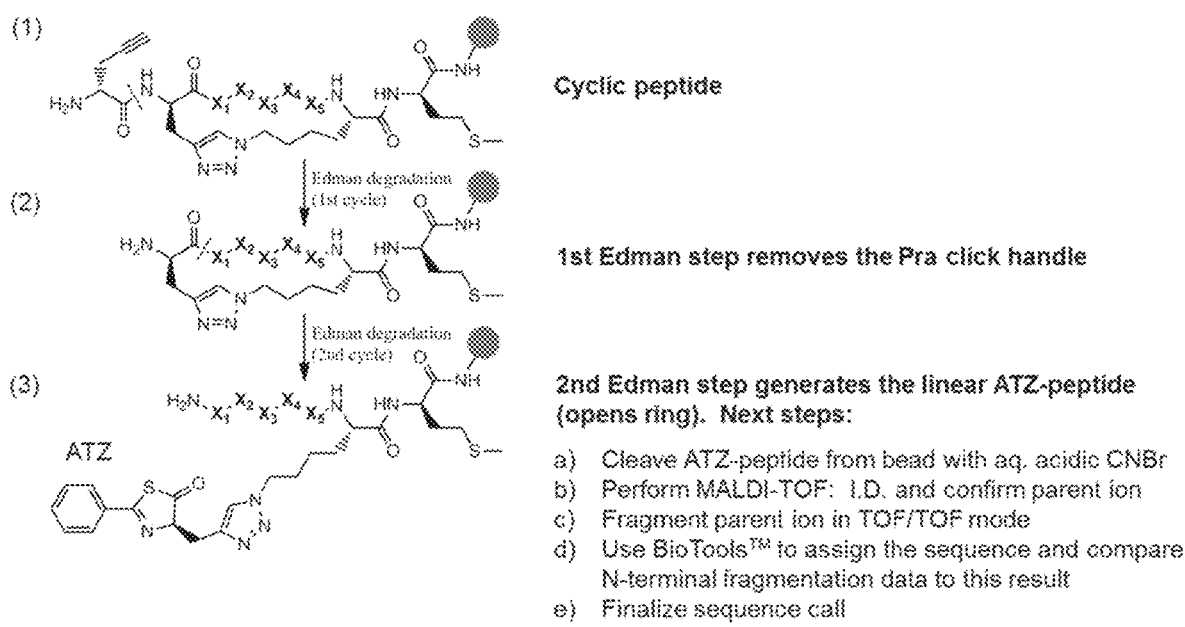
FIG. 2: Preparing Cyclic Peptide Hits for MALDI-TOF/TOF Sequencing. (1) Triazole-cyclized hit bead of the form H$_2$N-Pra-Cy(XXXXX-click)-(D-Met)-TG. (2) Bead after 1 st manual Edman degradation step. (3) Bead after 2nd manual Edman degradation step. The resultant linear ATZ-peptide is of a form compatible with MALDI-TOF/TOF sequencing.
Figure 3A:
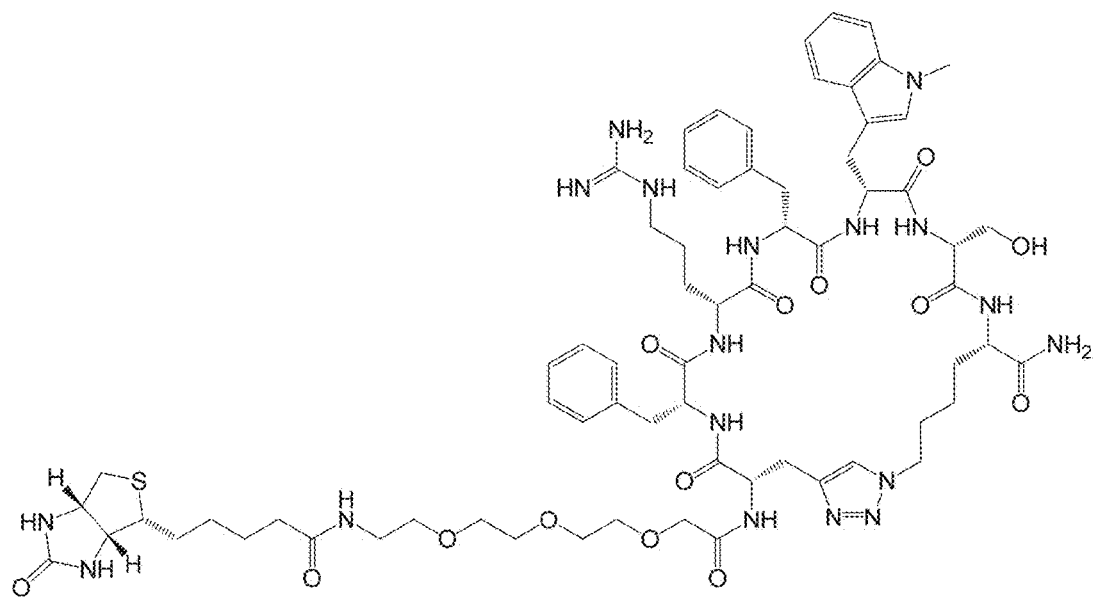
FIGS. 3A and 3B: In vitro characterization of macrocycle biotin-PEG$_3$-Cy(frf(Me-Trp)s). MALDI-MS (m/z): calcd. for C$_{68}$H$_{94}$N$_{18}$O$_{14}$S (M+H) 1419.65; found 1420.38.
Figure 3B:
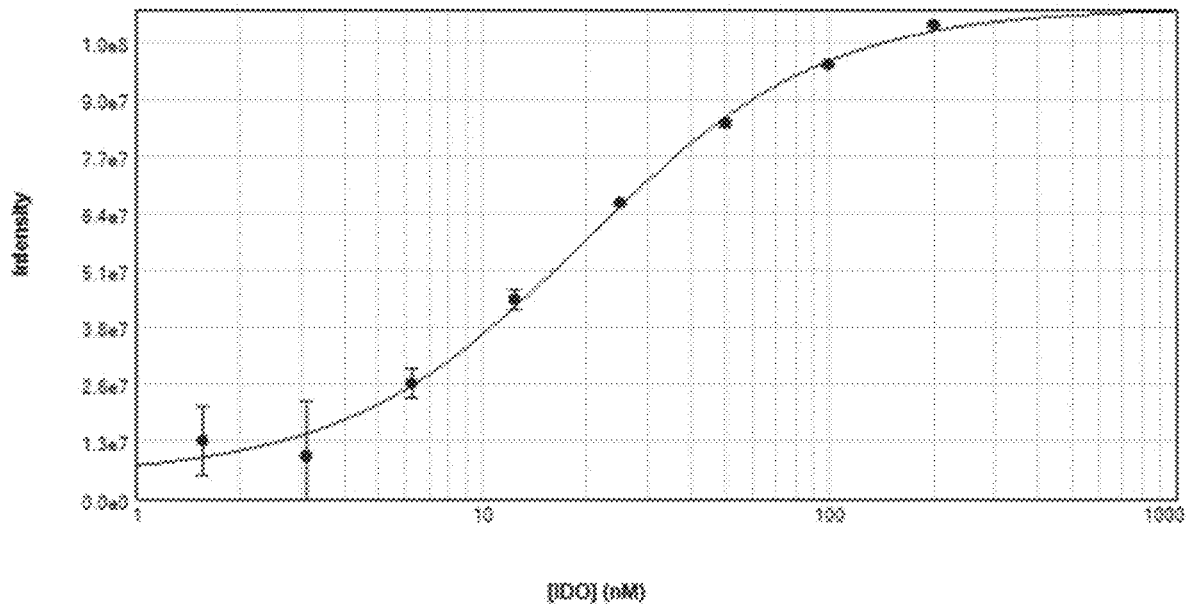
Figure 4A:
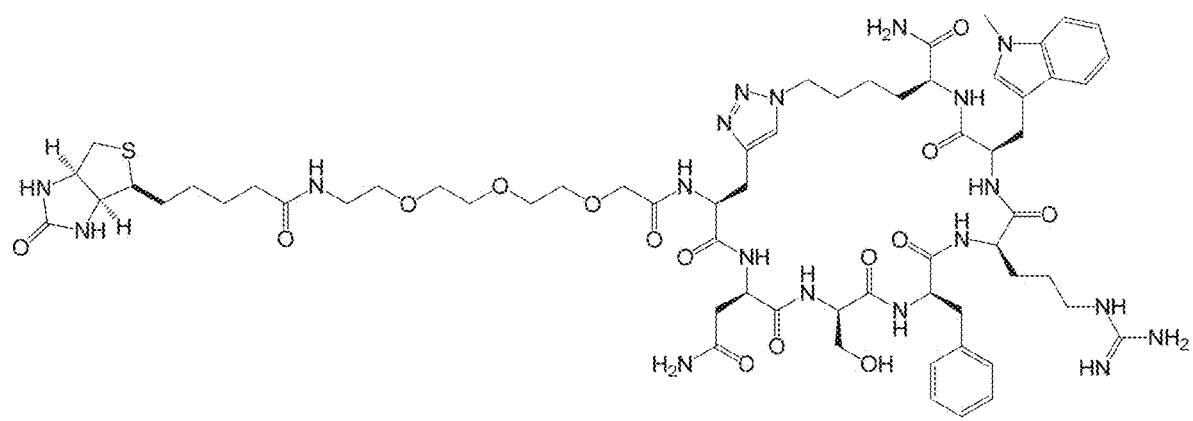
FIGS. 4A and 4B: In vitro characterization of macrocycle biotin-PEG$_3$-Cy(nsfr(Me-Trp)). MALDI-MS (m/z): calcd. for C$_{63}$H$_{91}$N$_{19}$O$_{15}$S (M+H) 1386.58; found 1387.26.
Figure 4B:
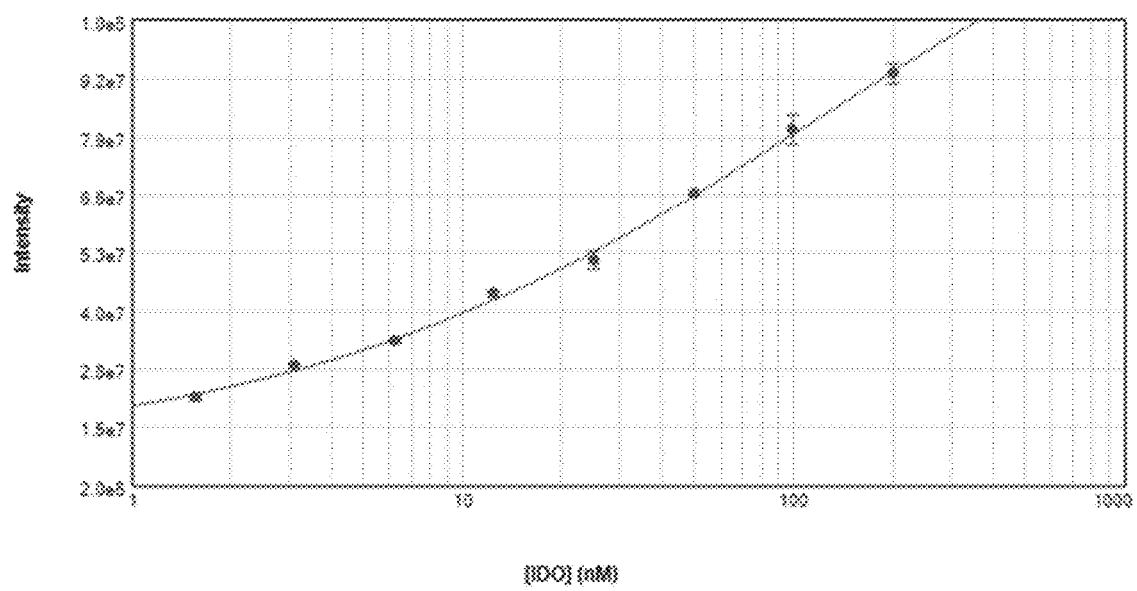
Figure 5A:
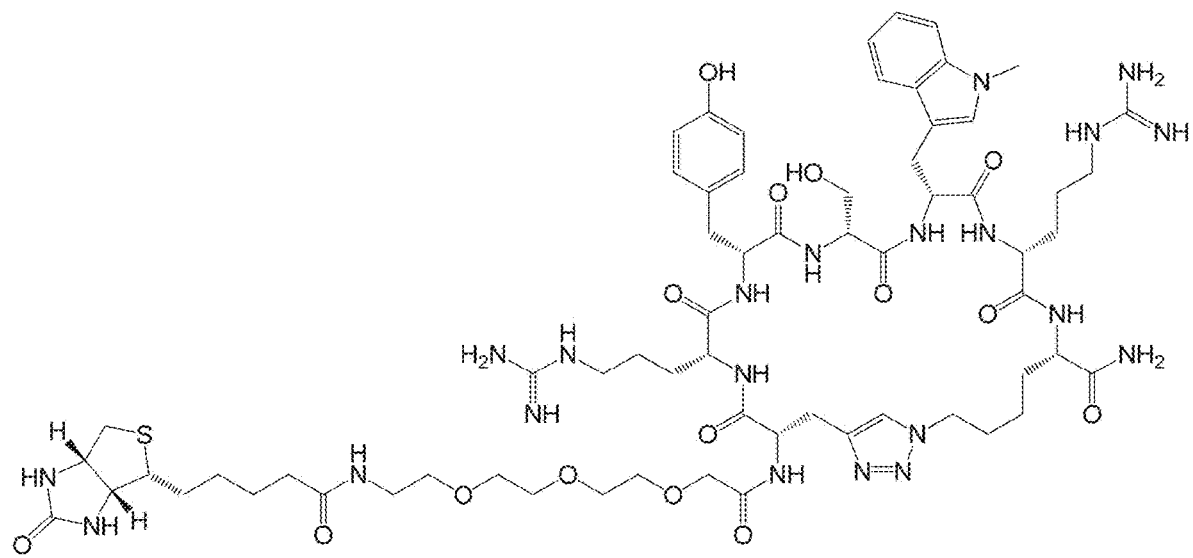
FIGS. 5A and 5B: In vitro characterization of macrocycle biotin-PEG$_3$-Cy(rys(Me-Trp)r). MALDI-MS (m/z): calcd. for C$_{65}$H$_{97}$N$_{21}$O$_{15}$S (M+H) 1444.66; found 1445.11.
Figure 5B:
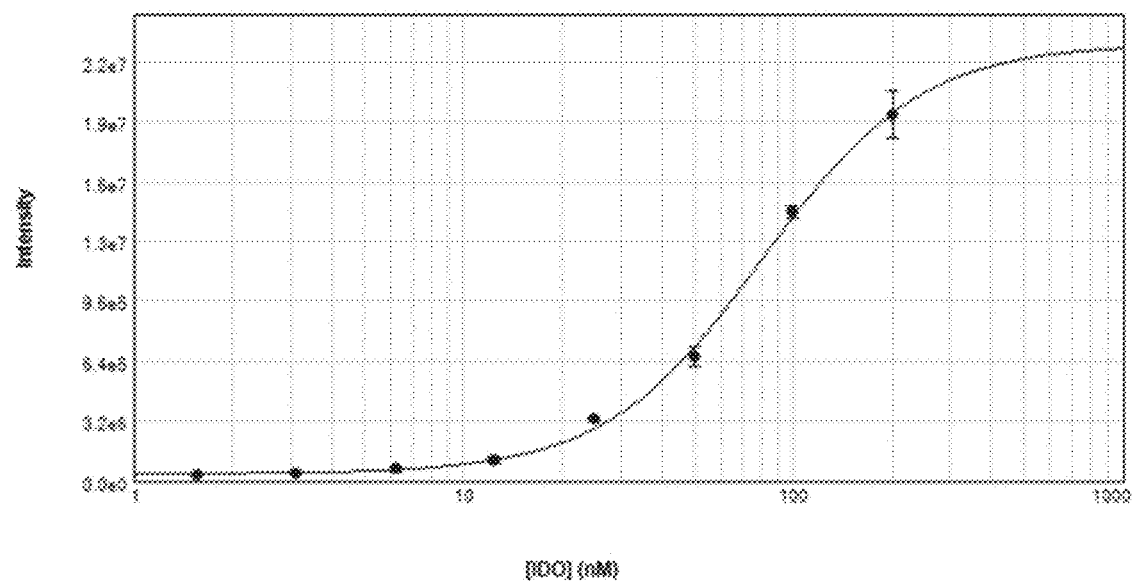
Figure 6A:
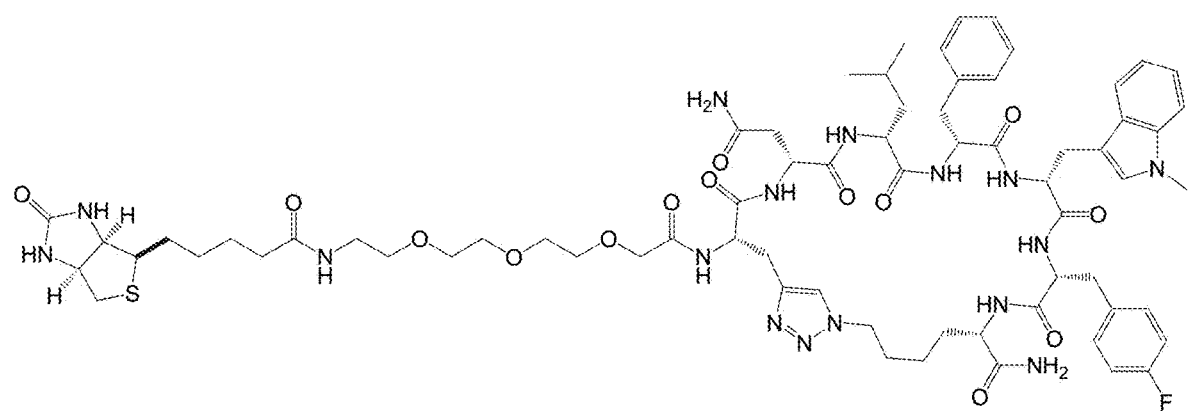
FIGS. 6A and 6B: In vitro characterization of macrocycle biotin-PEG$_3$-Cy(nlf(Me-Trp)(F-Phe)). MALDI-MS (m/z): calcd. for C$_{69}$H$_{93}$FN$_{16}$O$_{14}$S (M+H) 1421.64; found 1421.47.
Figure 6B:
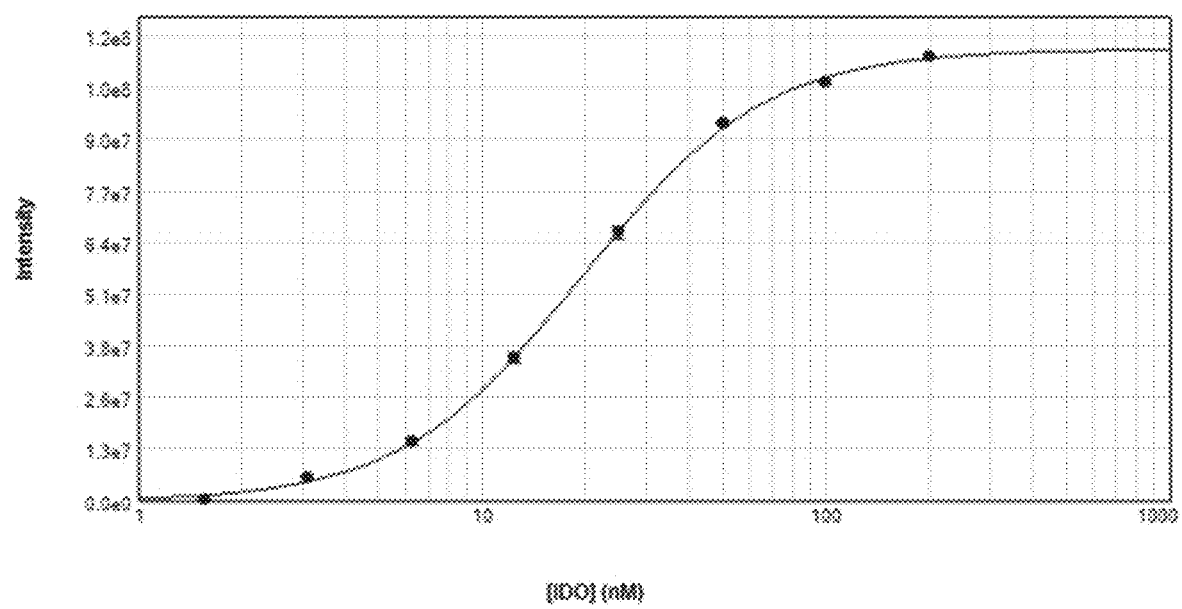
Figure 7A:
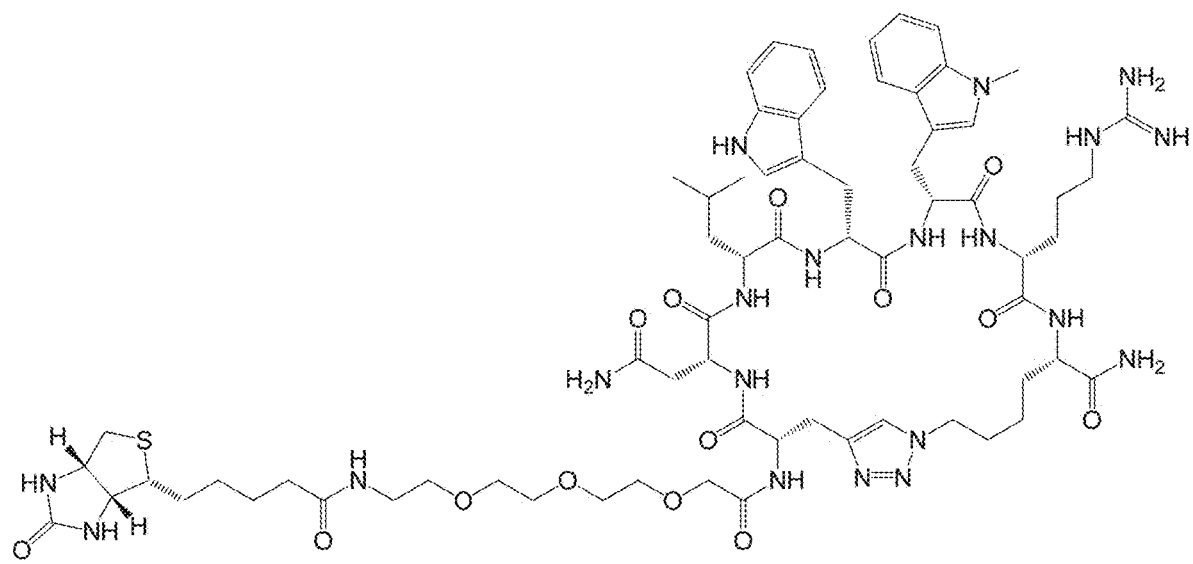
FIGS. 7A and 7B: In vitro characterization of macrocycle biotin-PEG$_3$-Cy(nlw(Me-Trp)r). MALDI-MS (m/z): calcd. for C$_{68}$H$_{98}$N$_{20}$O$_{14}$S (M+H) 1451.70; found 1452.17.
Figure 7B:
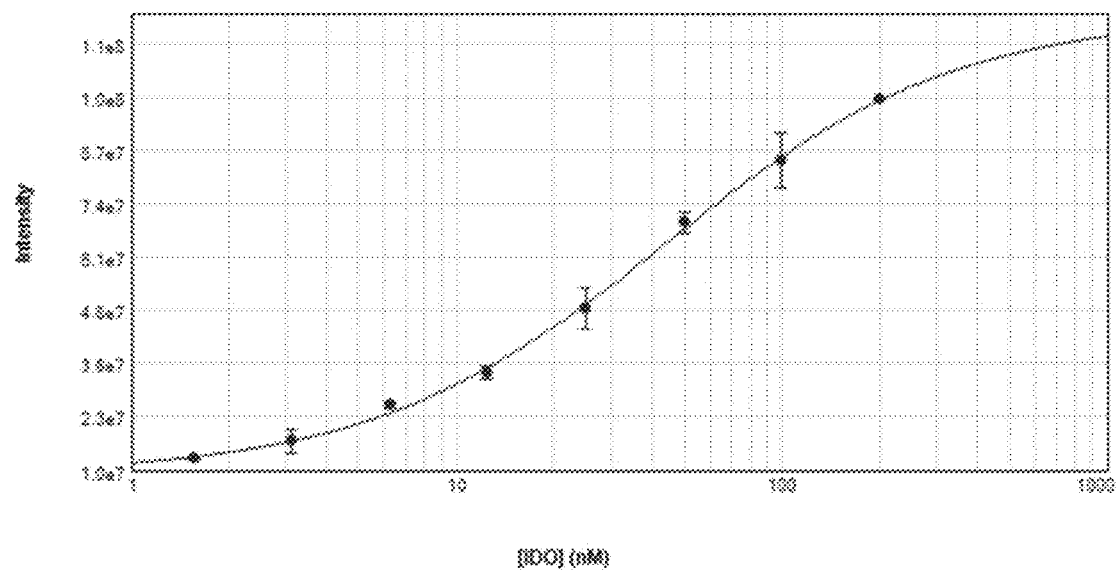
Figure 8A:
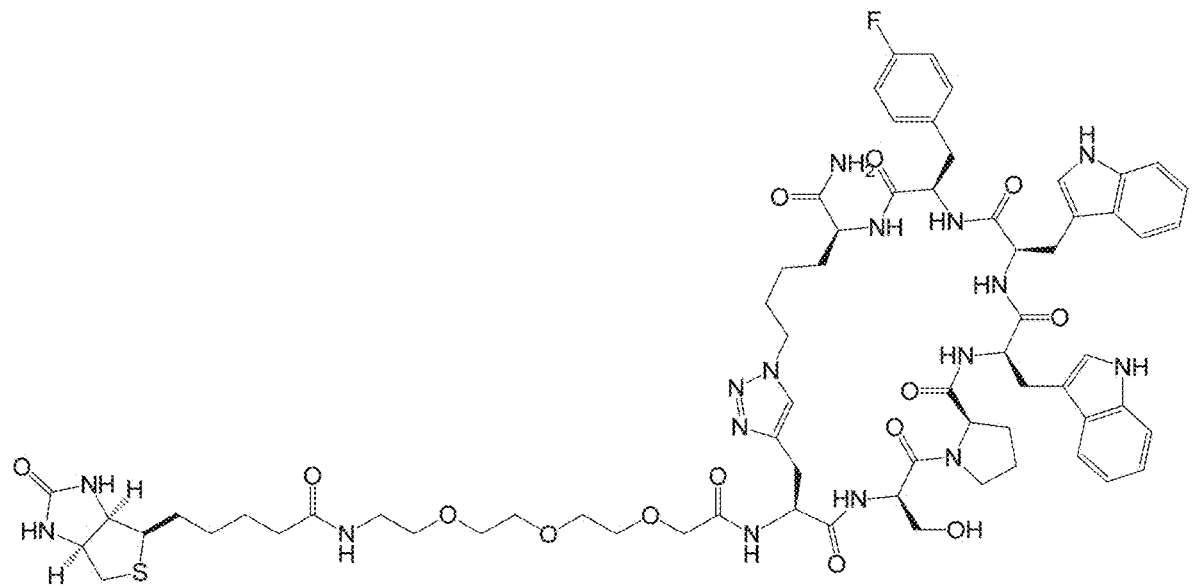
FIGS. 8A and 8B: In vitro characterization of macrocycle biotin-PEG$_3$-Cy(spww(F-Phe)). MALDI-MS (m/z): calcd. for C$_{68}$H$_{87}$FN$_{16}$O$_{14}$S (M+H) 1403.58; found 1403.60.
Figure 8B:
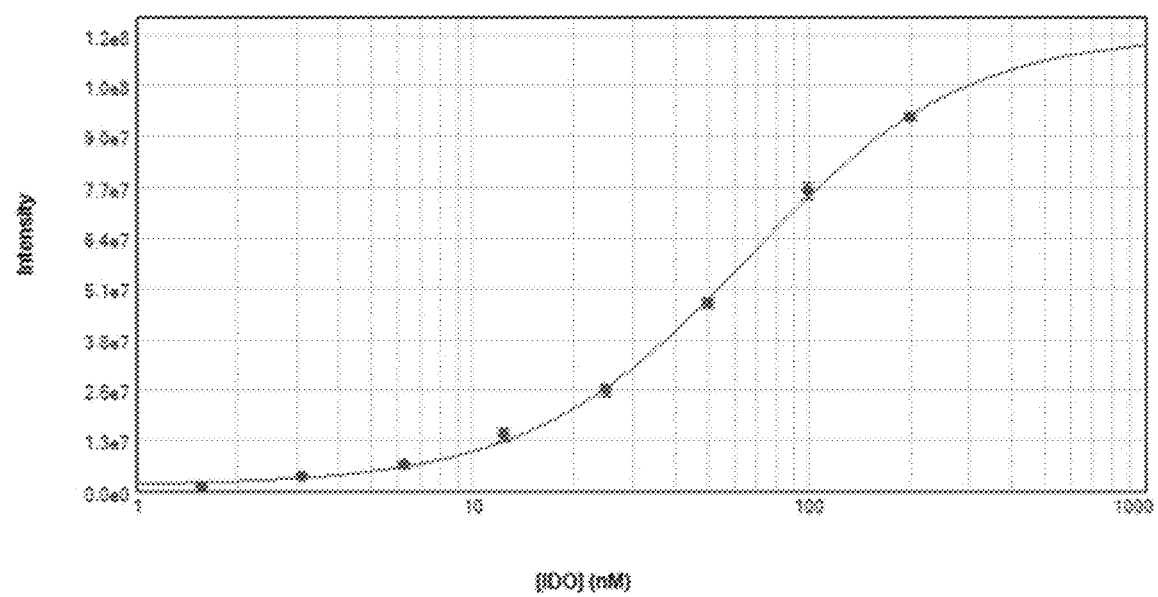
Figure 9A:
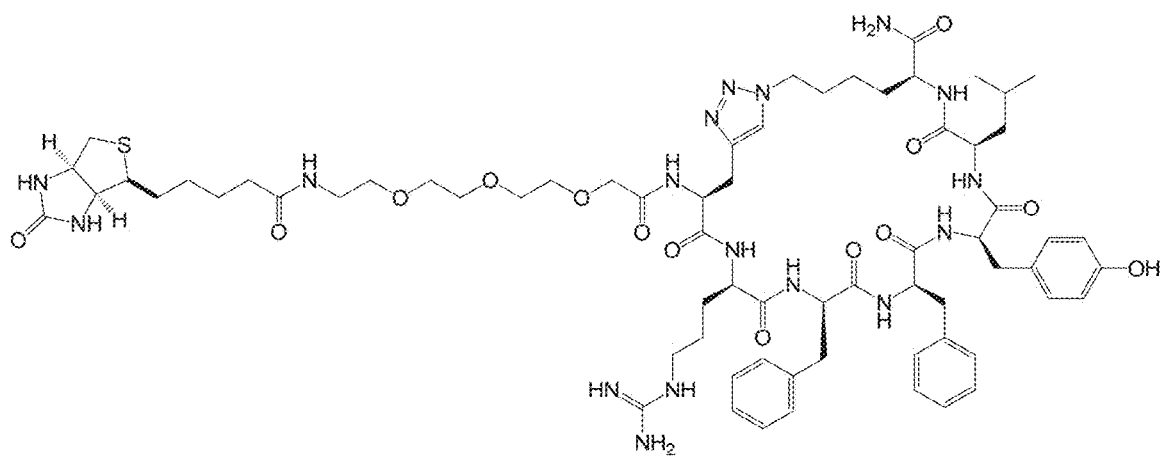
FIGS. 9A and 9B: In vitro characterization of macrocycle biotin-PEG$_3$-Cy(rffyl). MALDI-MS (m/z): calcd. for C$_{68}$H$_{97}$N$_{17}$O$_{14}$S (M+H) 1408.67; found 1408.92.
Figure 9B:
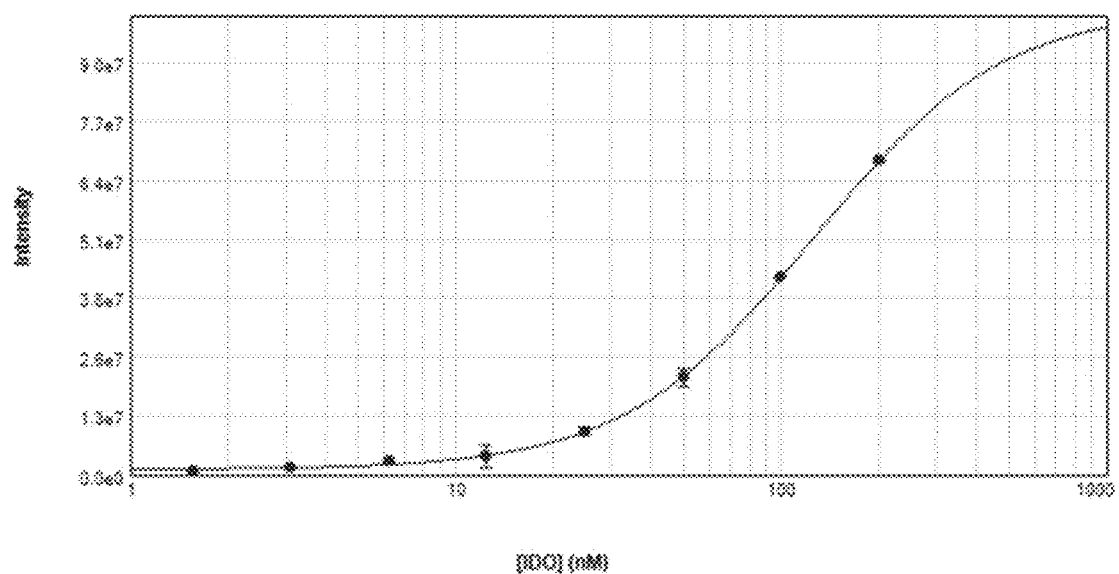
Figure 10A:
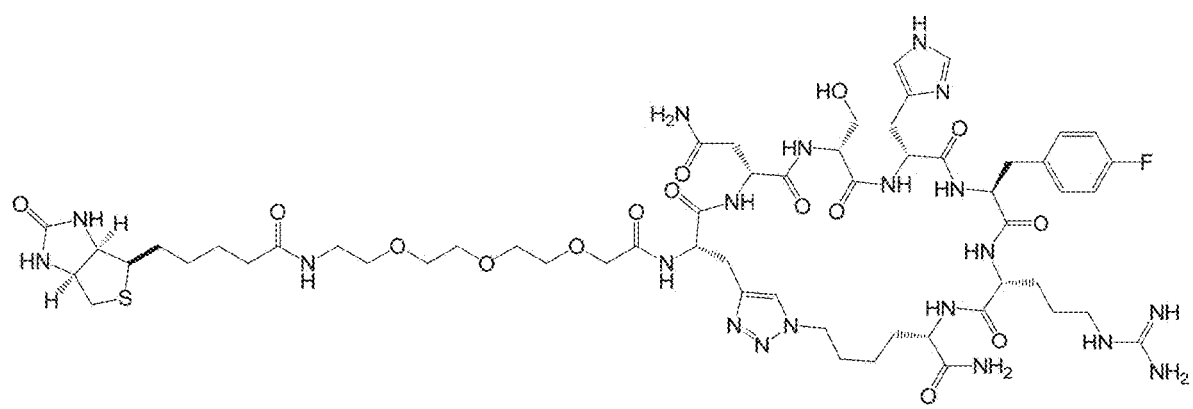
FIGS. 10A and 10B: In vitro characterization of macrocycle biotin-PEG$_3$-Cy(nsh(F-Phe)r). MALDI-MS (m/z): calcd. for C$_{57}$H$_{86}$FN$_{20}$O$_{15}$S (M+H) 1341.62; found 1341.63.
Figure 10B:
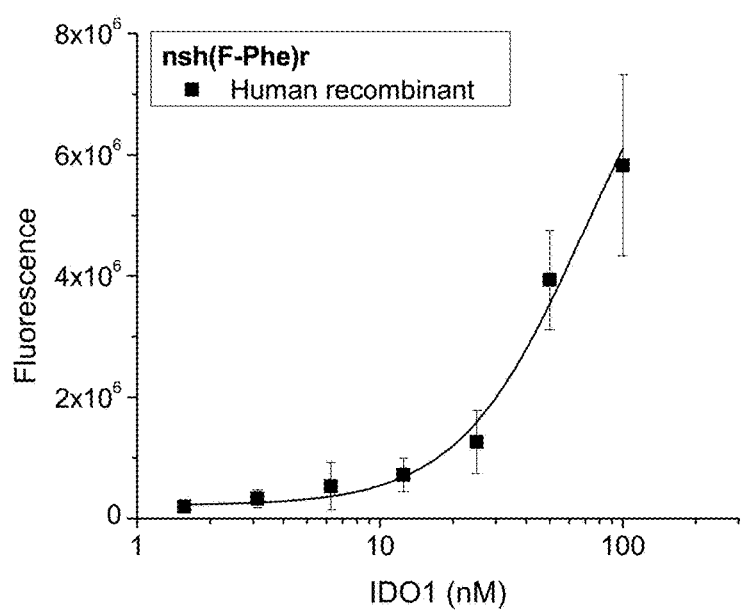
Figure 11A:
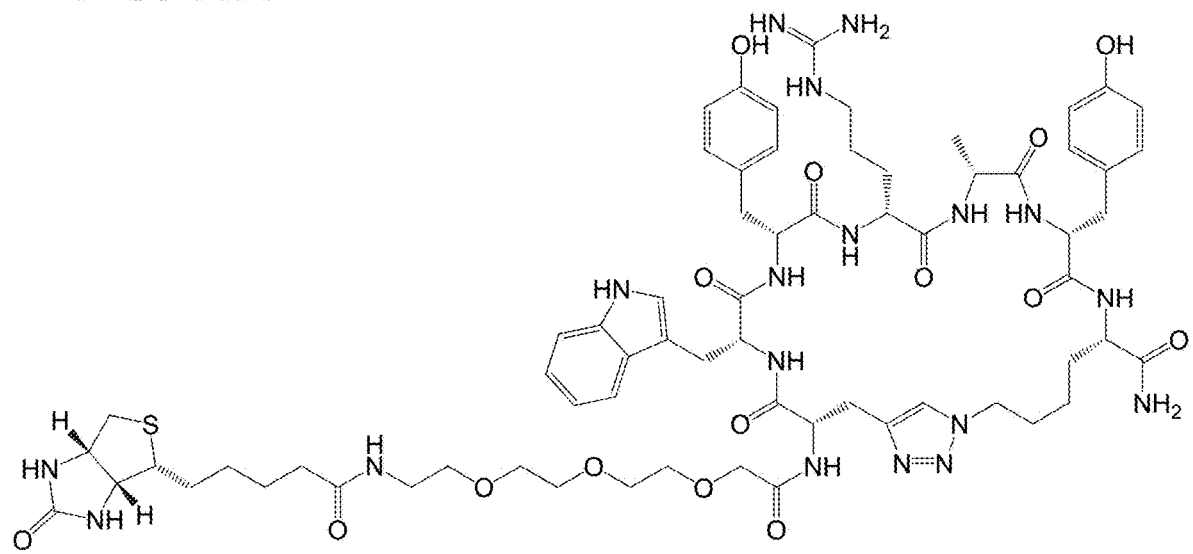
FIGS. 11A and 11B: In vitro characterization of macrocycle biotin-PEG$_3$-Cy(wyray). MALDI-MS (m/z): calcd. for C$_{67}$H$_{92}$N$_{18}$O$_{15}$S (M+H) 1420.67; found 1421.04.
Figure 11B:
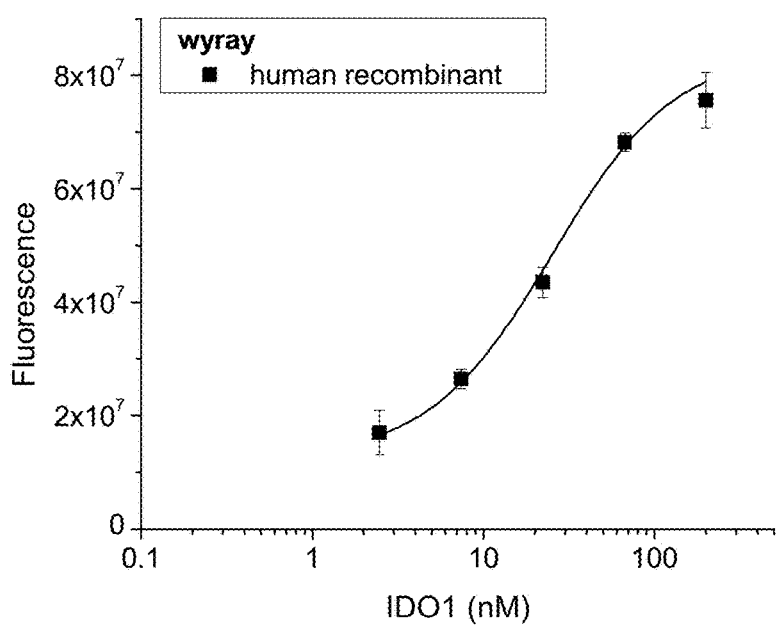
Figure 12A:
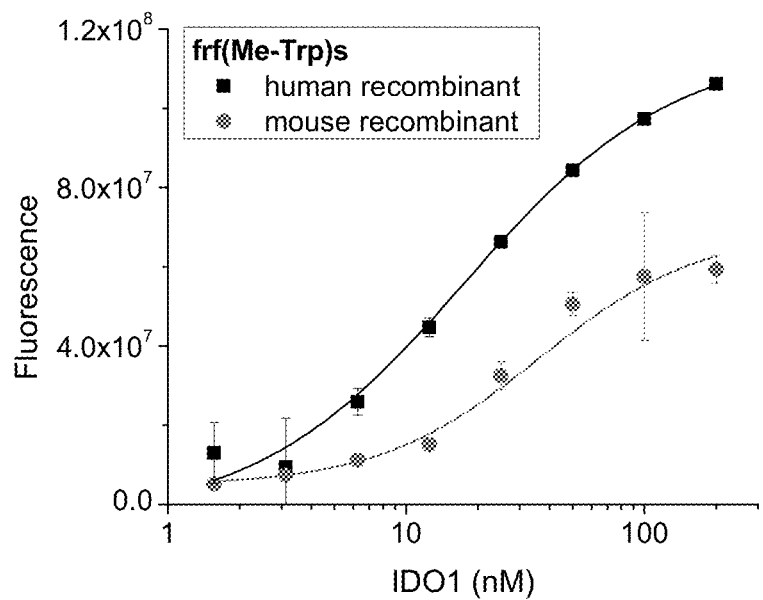
FIGS. 12A, 12B, 12C, 12D, 12E, 12F, 12G, and 12H: Binding affinities. Binding affinities of anti-human IDO1 macrocyclic peptide ligands against human (black, square) and murine (grey, circle) IDO1 proteins, as measured by ELISA.
Figure 12B:
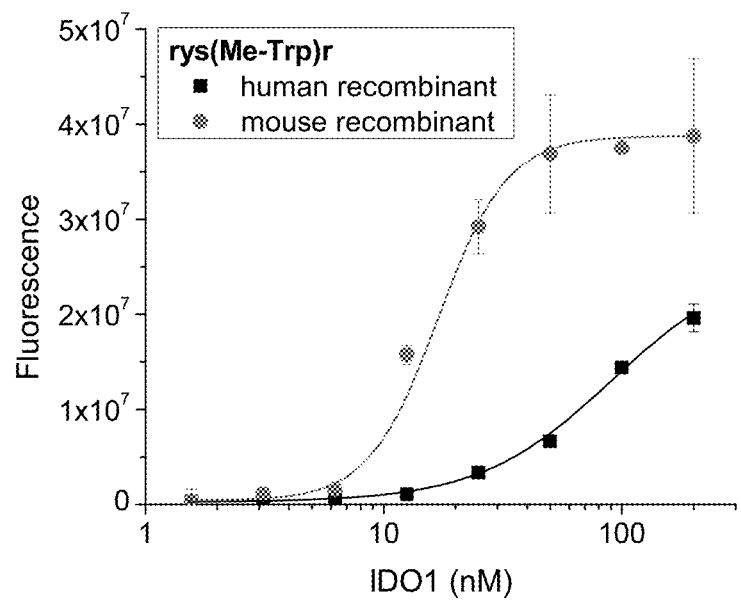
Figure 12C:
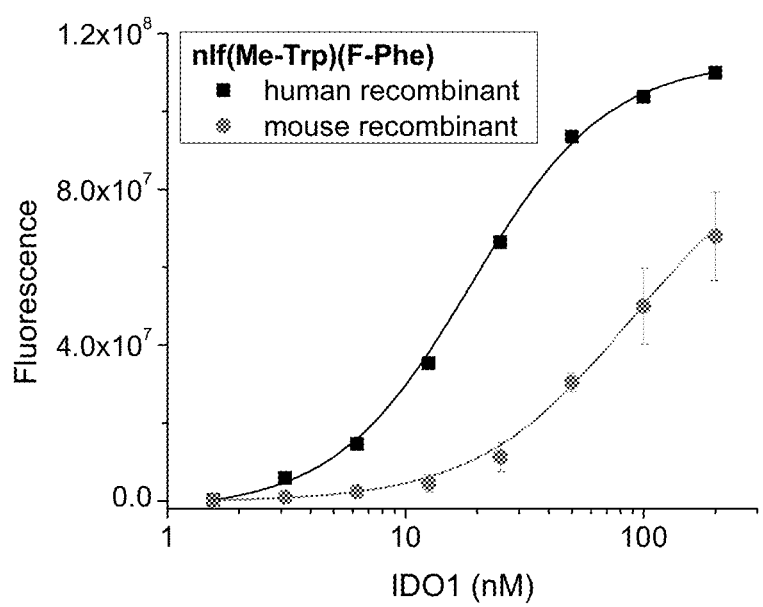
Figure 12D:
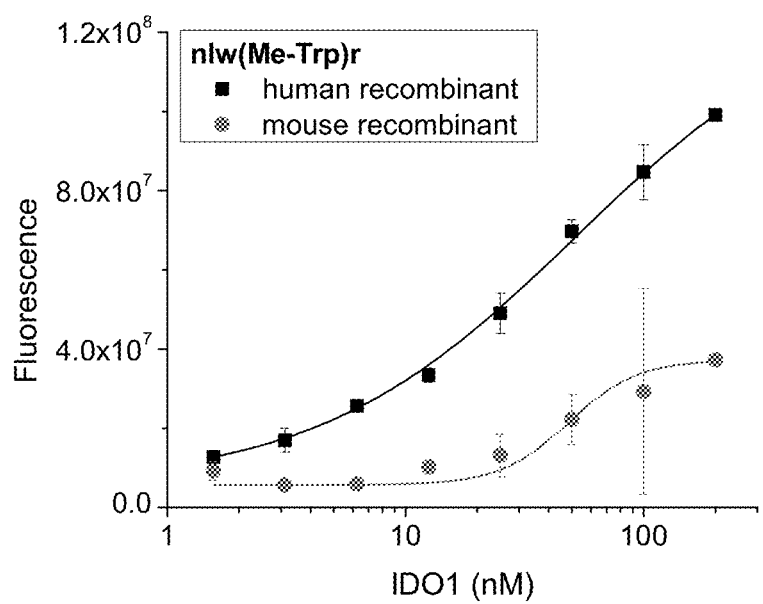
Figure 12E:
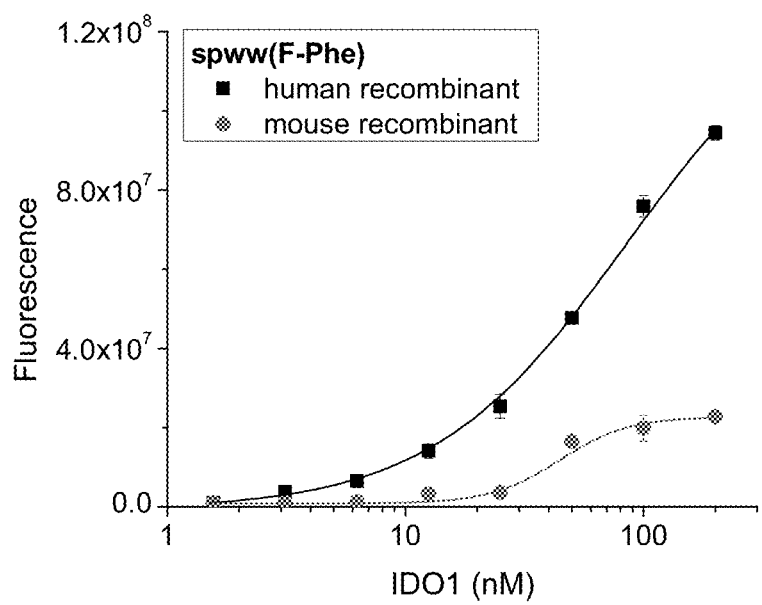
Figure 12F:
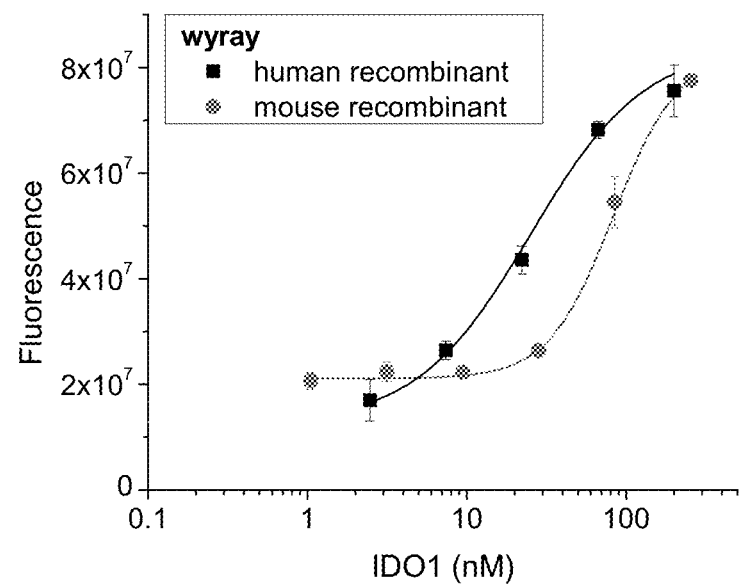
Figure 12G:
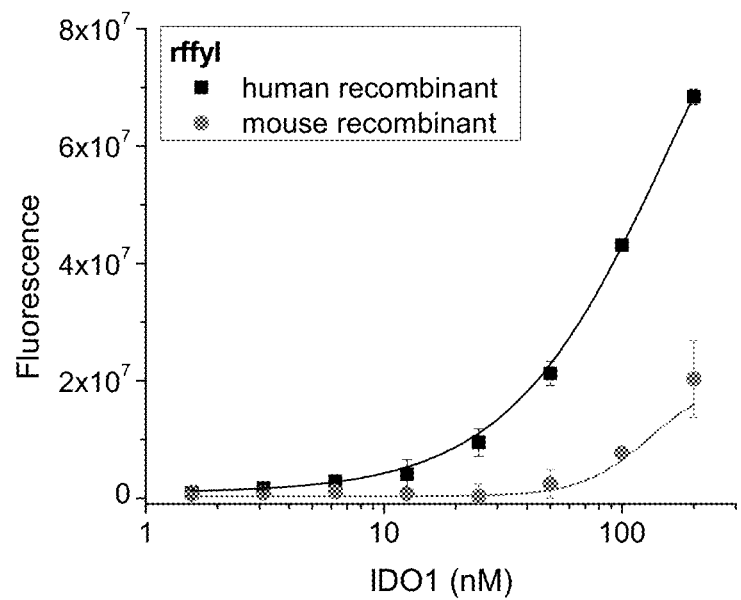
Figure 12H:
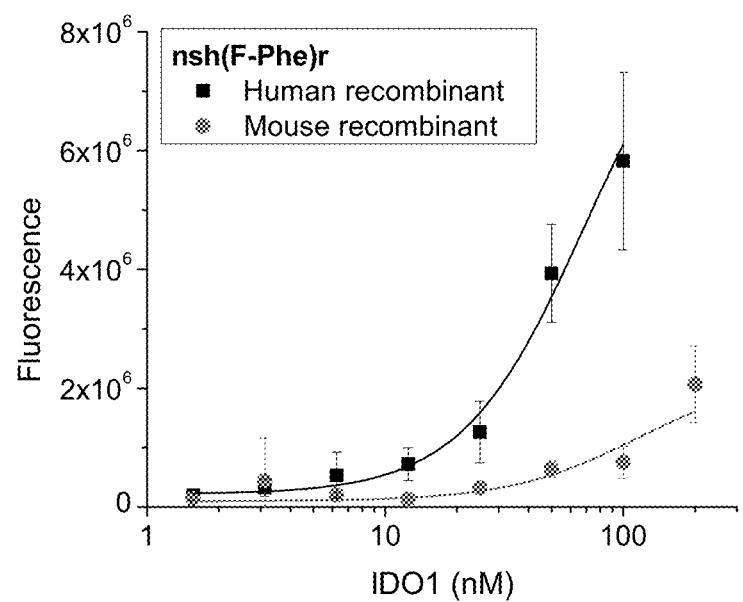

The following description of the invention is merely intended to illustrate various embodiments of the invention. As such, the specific modifications discussed are not to be construed as limitations on the scope of the invention. It will be apparent to one skilled in the art that various equivalents, changes, and modifications may be made without departing from the scope of the invention, and it is understood that such equivalent embodiments are to be included herein.

Unless the context requires otherwise, throughout the specification and claims, the word "comprise" and variations thereof, such as "comprises" and "comprising" are to be construed in an open, inclusive sense, that is as "including, but not limited to".

Reference throughout this specification to "one embodiment" or "an embodiment" means that a particular feature, structure or characteristic described in connection with the embodiment is included in at least one embodiment of the present invention. Thus, the appearances of the phrases "in one embodiment" or "in an embodiment" in various places throughout this specification are not necessarily all referring to the same embodiment. Furthermore, the particular features, structures, or characteristics may be combined in any suitable manner in one or more embodiments.

Epitope-targeted macrocyclic peptide ligands against IDO1 were identified using protein catalyzed capture agent (PCC) technology and were further developed as in vivo positron emission tomography (PET) imaging agents and IDO1 inhibitors. Three human IDO1 epitopes have been designed and screened against one-bead-one-compound (OBOC) peptide libraries. Two epitopes are located at or near the active site, while the third epitope is situated on the protein surface. Epitope-targeted macrocyclic peptide ligands were identified against IDO1 with binding affinities (EC50 values) ranging from 20 to 125 nM. In total, there are nine PCC macrocyclic ligands (three for IDO1 Epitope1, four for IDO1 Epitope2, and two for IDO1 Epitope3).

Epitope-targeted macrocyclic peptide ligands against IDO1 were developed by in situ click screening of one-bead-one-compound (OBOC) peptide libraries. Screens were performed against human IDO1 epitopes that show high homology with mouse IDO1. These ligands were designed to bind to specific synthetic epitopes of IDO1, in a manner reminiscent of monoclonal antibodies (mAbs). Cyclic peptides have an ability to display protein-like epitopes with restricted conformational flexibility and thus often display enhanced bioavailability, increased stability towards metabolic degradation, and superior binding affinities as compared to their linear counterparts.

In one embodiment, the peptide library is composed of exclusively D-amino acids and artificial amino acids. IDO1 inhibitor, 1-methyl-Ltryptophan (Me-Trp), is added during synthesis of the library for increasing hits that recognize the IDO1 active site. In another embodiment, 4-fluoro-L-phenylalanine (F-Phe) is added during synthesis of the library for increasing cell penetration.

Two biligand strategies are pursued to achieve low nM to pM binding. Biligands can be developed by attaching a small molecule inhibitor to an epitope-targeted PCC macrocycle anchor. This approach takes advantage of a small molecule inhibitor which can add specificity and assist in cell penetration. Biligands can also be developed by joining together pairs of two epitope-targeted PCC macrocyclic peptide ligands using a chemical linker to promote cell penetration. Cell penetration and cellular activity studies of ligands and biligands are pursued with input from medicinal chemistry. The optimized, cell-penetrant PCCs display specific binding and in vivo pharmacokinetics compatible with imaging IDO1 in vivo using fluorine-18 PET. Separately, the PCCs are investigated as novel therapeutic compounds.

In certain embodiments, the term "IDO1" as used herein refers to human IDO1. In some embodiments, IDO1 comprises one of the following amino acid sequence or an amino acid sequence substantially identical to it.

```
Human IDO1 protein
                                         (SEQ ID NO: 8)
AHAMENSWTISKEYHIDEEVGFALPNPQENLPDFYNDWMFIAKHLPDLI

ESGQLRERVEKLNMLSIDHLTDHKSQRLARLVLGCITMAYVWGKGHGDV

RKVLPRNIAVPYCQLSKKLELPPILVYADCVLANWKKKDPNKPLTYENM

DVLFSFRDGDCSKGFFLVSLLVEIAAASAIKVIPTVFKAMQMQERDTLL

KALLEIASCLEKALQVFHQIHDHVNPKAFFSVLRIYLSGWKGNPQLSDG

LVYEGFWEDPKEFAGGSAGQSSVFQCFDVLLGIQQTAGGGHAAQFLQDM

RRYMPPAHRNFLCSLESNPSVREFVLSKGDAGLREAYDACVKALVSLRS

YHLQIVTKYILIPASQQPKENKTSEDPSKLEAKGTGGTDLMNFLKTVRS

TTEKSLLKEG

Mouse IDO1 protein
                                         (SEQ ID NO: 9)
ALSKISPTEGSRRILEDHHIDEDVGFALPHPLVELPDAYSPWVLVARNL

PVLIENGQLREEVEKLPTLSTDGLRGHRLQRLAHLALGYITMAYVWNRG

DDDVRKVLPRNIAVPYCELSEKLGLPPILSYADCVLANWKKKDPNGPMT

YENMDILFSFPGGDCDKGFFLVSLLVEIAASPAIKAIPTVSSAVERQDL

KALEKALHDIATSLEKAKEIFKRMRDFVDPDTFFHVLRIYLSGWKCSSK

LPEGLLYEGVWDTPKMFSGGSAGQSSIFQSLDVLLGIKHEAGKESPAEF

LQEMREYMPPAHRNFLFFLESAPPVREFVISRHNEDLTKAYNECVNGLV

SVRKFHLAIVDTYIMKPSKKKPTDGDKSEEPSNVESRGTGGTNPMTFLR

SVKDTTEKALLSWP
```

As used herein, the term "mammal" includes humans and both domestic animals such as laboratory animals and household pets (e.g., cats, dogs, swine, cattle, sheep, goats, horses, rabbits), and non-domestic animals such as wildlife and the like.

The term "capture agent" as used herein refers to a composition that comprises one or more target-binding moieties, or ligands which specifically binds to a target protein via those target-binding moieties. Each target-binding moiety exhibits binding affinity for the target protein, either individually or in combination with other target-binding moieties. In certain embodiments, each target-binding moiety binds to the target protein via one or more non-covalent interactions, including for example hydrogen bonds, hydrophobic interactions, and van der Waals interactions. A capture agent may comprise one or more organic molecules, including for example polypeptides, peptides, polynucleotides, and other non-polymeric molecules. In some aspects a capture agent is a protein catalyzed capture agent. In specific embodiments, capture agents comprising one or more peptide ligands that specifically bind IDO1 are also referred to as epitope-targeted macrocyclic peptide ligands against IDO1.

Reference to "capture agents" further refers to pharmaceutically acceptable salts thereof. "Pharmaceutically acceptable salt" includes both acid and base addition salts.

"Pharmaceutically acceptable acid addition salt" refers to those salts which retain the biological effectiveness and properties of the free bases, which are not biologically or otherwise undesirable, and which are formed with inorganic acids such as, but are not limited to, hydrochloric acid, hydrobromic acid, sulfuric acid, nitric acid, phosphoric acid and the like, and organic acids such as, but not limited to, acetic acid, 2,2-dichloroacetic acid, adipic acid, alginic acid, ascorbic acid, aspartic acid, benzenesulfonic acid, benzoic acid, 4-acetamidobenzoic acid, camphoric acid, camphor-10-sulfonic acid, capric acid, caproic acid, caprylic acid, carbonic acid, cinnamic acid, citric acid, cyclamic acid, dodecylsulfuric acid, ethane-1,2-disulfonic acid, ethanesulfonic acid, 2-hydroxyethanesulfonic acid, formic acid, fumaric acid, galactaric acid, gentisic acid, glucoheptonic acid, gluconic acid, glucuronic acid, glutamic acid, glutaric acid, 2-oxo-glutaric acid, glycerophosphoric acid, glycolic acid, hippuric acid, isobutyric acid, lactic acid, lactobionic acid, lauric acid, maleic acid, malic acid, malonic acid, mandelic acid, methanesulfonic acid, mucic acid, naphthalene-1,5-disulfonic acid, naphthalene-2-sulfonic acid, 1-hydroxy-2-naphthoic acid, nicotinic acid, oleic acid, orotic acid, oxalic acid, palmitic acid, pamoic acid, propionic acid, pyroglutamic acid, pyruvic acid, salicylic acid, 4-aminosalicylic acid, sebacic acid, stearic acid, succinic acid, tartaric acid, thiocyanic acid, p-toluenesulfonic acid, trifluoroacetic acid, undecylenic acid, and the like.

"Pharmaceutically acceptable base addition salt" refers to those salts which retain the biological effectiveness and properties of the free acids, which are not biologically or otherwise undesirable. These salts are prepared from addition of an inorganic base or an organic base to the free acid. Salts derived from inorganic bases include, but are not limited to, the sodium, potassium, lithium, ammonium, calcium, magnesium, iron, zinc, copper, manganese, aluminum salts and the like. Preferred inorganic salts are the ammonium, sodium, potassium, calcium, and magnesium salts. Salts derived from organic bases include, but are not limited to, salts of primary, secondary, and tertiary amines, substituted amines including naturally occurring substituted amines, cyclic amines and basic ion exchange resins, such as ammonia, isopropylamine, trimethylamine, diethylamine, triethylamine, tripropylamine, diethanolamine, ethanolamine, deanol, 2 dimethylaminoethanol, 2 diethylaminoethanol, dicyclohexylamine, lysine, arginine, histidine, caffeine, procaine, hydrabamine, choline, betaine, benethamine, benzathine, ethylenediamine, glucosamine, methylglucamine, theobromine, triethanolamine, tromethamine, purines, piperazine, piperidine, N ethylpiperidine, polyamine resins and the like. Particularly preferred organic bases are isopropylamine, diethylamine, ethanolamine, trimethylamine, dicyclohexylamine, choline and caffeine.

The capture agents described herein, or their pharmaceutically acceptable salts may contain one or more asymmetric centers and may thus give rise to enantiomers, diastereomers, and other stereoisomeric forms that may be defined, in terms of absolute stereochemistry, as (R) or (S) or, as (D) or (L) for amino acids. The present invention is meant to include all such possible isomers, as well as their racemic and optically pure forms. Optically active (+) and ( ), (R) and (S), or (D) and (L) isomers may be prepared using chiral synthons or chiral reagents, or resolved using conventional techniques, for example, chromatography and fractional crystallization. Conventional techniques for the preparation/isolation of individual enantiomers include chiral synthesis from a suitable optically pure precursor or resolution of the racemate (or the racemate of a salt or derivative) using, for example, chiral high pressure liquid chromatography (HPLC). When the compounds described herein contain olefinic double bonds or other centers of geometric asymmetry, and unless specified otherwise, it is intended that the compounds include both E and Z geometric isomers. Likewise, all tautomeric forms are also intended to be included. (D)-amino acids (also referred to as D-amino acids) are referred to herein in lower case letters (e.g. D-valine is referred to as "v"), while (L)-amino acids (also referred to herein as L-amino acids) are referred to in upper case letters (e.g. L-valine or valine is referred to as "V"). Glycine is non-chiral and is referred to as "G".

A "stereoisomer" refers to a compound made up of the same atoms bonded by the same bonds but having different three-dimensional structures, which are not interchangeable. The present invention contemplates various stereoisomers and mixtures thereof and includes "enantiomers", which refers to two stereoisomers whose molecules are nonsuperimposeable mirror images of one another.

A "tautomer" refers to a proton shift from one atom of a molecule to another atom of the same molecule. The present invention includes tautomers of any said compounds.

The term "epitope" as used herein refers to a distinct molecular surface of a protein (e.g., IDO1). Typically, the epitope is a polypeptide and it can act on its own as a finite sequence of 10-40 amino acids.

The terms "polypeptide," "peptide," and "protein" are used interchangeably herein to refer to an amino acid sequence comprising a polymer of amino acid residues. The terms apply to amino acid polymers in which one or more amino acid residues is an artificial chemical mimetic of a corresponding naturally occurring amino acid, as well as to naturally occurring amino acid polymers and non-naturally occurring amino acid polymers.

The term "amino acid" refers to naturally occurring and synthetic amino acids, as well as amino acid analogs and amino acid mimetics that function in a manner similar to the naturally occurring amino acids, and isomers thereof. Naturally occurring amino acids are those encoded by the genetic code, as well as those amino acids that are later modified, e.g., hydroxyproline, carboxyglutamate, O-phosphoserine, and isomers thereof. The term "amino acid analogs" refers to compounds that have the same basic chemical structure as a naturally occurring amino acid, i.e., a carbon that is bound to a hydrogen, a carboxyl group, an amino group, and an R group, e.g., homoserine, norleucine, methionine sulfoxide, methionine methyl sulfonium. Such analogs have modified R groups (e.g., norleucine) or modified peptide backbones, but retain the same basic chemical structure as a naturally occurring amino acid. The term "amino acid mimetics" refers to chemical compounds that have a structure that is different from the general chemical structure of an amino acid, but that functions in a manner similar to a naturally occurring amino acid. Amino acids may be referred to herein by either their commonly known three letter symbols or by the one-letter symbols recommended by the IUPAC-IUB Biochemical Nomenclature Commission.

The term "artificial amino acid" as used herein refers to an amino acid that is different from the twenty naturally occurring amino acids (alanine, arginine, glycine, asparagine, aspartic acid, cysteine, glutamine, glutamic acid, serine, threonine, histidine, lysine, methionine, proline, valine, isoleucine, leucine, tyrosine, tryptophan, phenylalanine) in its side chain functionality. The non-natural amino acid can be a close analog of one of the twenty natural amino acids, or it can introduce a completely new functionality and chemistry, as long as the hydrophobicity of the non-natural amino acid is either equivalent to or greater than that of the natural amino acid. The non-natural amino acid can either replace an existing amino acid in a protein (substitution), or be an addition to the wild type sequence (insertion). The incorporation of non-natural amino acids can be accomplished by known chemical methods including solid-phase peptide synthesis or native chemical ligation, or by biological methods. In certain embodiments, artificial amino acids include 4-fluoro-L-phenylalanine (F-Phe) and 1-methyl-L-tryptophan (Me-Trp).

The terms "specific binding," "selective binding," "selectively binds," or "specifically binds" as used herein refer to capture agent binding to an epitope on a predetermined antigen. Typically, the capture agent binds with an affinity ($K_D$) of approximately less than $10^{-7}$ M, such as approximately less than $10^{-8}$ M, $10^{-9}$ M or $10^{-10}$ M or even lower.

The term "$K_D$" as used herein refers to the dissociation equilibrium constant of a particular capture agent-antigen interaction.

The term "$k_d$" ($sec^{-1}$) as used herein refers to the dissociation rate constant of a particular capture agent-antigen interaction. Said value is also referred to as the $k_{off}$ value.

The term "$k_a$" ($M^{-1} \times sec^{-1}$) as used herein refers to the association rate constant of a particular capture agent-antigen interaction.

The term "$K_D$" (M) as used herein refers to the dissociation equilibrium constant of a particular capture agent-antigen interaction.

The term "$K_A$" ($M^{-1}$) as used herein refers to the association equilibrium constant of a particular capture agent-antigen interaction and is obtained by dividing the $k_a$ by the $k_d$.

The term "imaging agent" refers to capture agents that have been labeled for detection. In certain embodiments, imaging agents are isotopically-labelled by having one or more atoms replaced by an atom having a different atomic mass or mass number. Examples of isotopes that can be incorporated into the disclosed compounds include isotopes of hydrogen, carbon, nitrogen, oxygen, phosphorous, fluorine, chlorine, and iodine, such as $^2H$, $^3H$, $^{11}C$, $^{13}C$, $^{14}C$, $^{13}N$, $^{15}N$, $^{15}O$, $^{17}O$, $^{18}O$, $^{31}P$, $^{32}P$, $^{35}S$, $^{18}F$, $^{36}Cl$, $^{123}I$, and $^{125}I$, respectively. These radiolabeled compounds could be useful to help determine or measure the effectiveness of the compounds, by characterizing, for example, the site or mode of action, or binding affinity to a pharmacologically important site of action. Certain isotopically-labelled disclosed imaging agents, for example, those incorporating a radioactive isotope, are useful in drug and/or substrate tissue distribution studies. The radioactive isotopes tritium, i.e. $^3H$, and carbon-14, i.e. $^{14}C$, are particularly useful for this purpose in view of their ease of incorporation and ready means of detection.

Substitution with heavier isotopes such as deuterium, i.e. $^2H$, may afford certain therapeutic advantages resulting from greater metabolic stability, for example, increased in vivo half-life or reduced dosage requirements, and hence may be preferred in some circumstances.

Substitution with positron emitting isotopes, such as $^{11}C$, $^{18}F$, $^{15}O$ and $^{13}N$, can be useful in Positron Emission Topography (PET) studies for examining substrate receptor occupancy. Isotopically-labeled imaging agents can generally be prepared by conventional techniques known to those skilled in the art or by processes analogous to those described in the Examples as set out below using an appropriate isotopically-labeled reagent in place of the non-labeled reagent previously employed.

The present disclosure is also meant to encompass the in vivo metabolic products of the disclosed imaging agents. Such products may result from, for example, the oxidation, reduction, hydrolysis, amidation, esterification, and the like of the administered compound, primarily due to enzymatic processes. Accordingly, the invention includes compounds produced by a process comprising administering a compound of this invention to a mammal for a period of time sufficient to yield a metabolic product thereof. Such products are typically identified by administering a radiolabelled compound of the invention in a detectable dose to an animal, such as rat, mouse, guinea pig, monkey, or to human, allowing sufficient time for metabolism to occur, and isolating its conversion products from the urine, blood or other biological samples.

A "pharmaceutical composition" refers to a formulation of a compound of the invention and a medium generally accepted in the art for the delivery of the biologically active compound to mammals, e.g., humans. Such a medium includes all pharmaceutically acceptable carriers, diluents or excipients therefor.

The term "condition" as used herein refers generally to a disease, event, or a change in health status. A change in health status may be associated with a particular disease or event, in which case the change may occur simultaneously with or in advance of the disease or event. In those cases where the change in health status occurs in advance of a disease or event, the change in health status may serve as a predictor of the disease or event. For example, a change in health status may be an alteration in the expression level of a particular gene associated with a disease or event. Alternatively, a change in health status may not be associated with a particular disease or event.

The terms "treat," "treating," or "treatment" as used herein generally refer to preventing a condition or event, slowing the onset or rate of development of a condition or delaying the occurrence of an event, reducing the risk of developing a condition or experiencing an event, preventing or delaying the development of symptoms associated with a condition or event, reducing or ending symptoms associated with a condition or event, generating a complete or partial regression of a condition, lessening the severity of a condition or event, or some combination thereof.

An "effective amount" or "therapeutically effective amount" as used herein refers to an amount effective, at dosages and for periods of time necessary, to achieve a desired therapeutic result. A therapeutically effective amount of a disclosed binding agent may vary according to factors such as the disease state, age, sex, and weight of the individual, and the ability of the binding agent to elicit a desired response in the individual.

The term "stable" as used herein with regard to a binding agent, protein catalyzed capture agent, or pharmaceutical formulation thereof refers to the agent or formulation retaining structural and functional integrity for a sufficient period of time to be utilized in the methods described herein.

The term "synthetic" as used herein with regard to a protein catalyzed capture agent or binding agent refers to the binding agent having been generated by chemical rather than biological means.

Unless otherwise stated, sequence identity/similarity values provided herein refer to the value obtained using the BLAST 2.0 suite of programs using default parameters (Altschul, et al., (1997) Nucleic Acids Res. 25:3389-402).

As those of ordinary skill in the art will understand, BLAST searches assume that proteins can be modeled as random sequences. However, many real proteins comprise regions of nonrandom sequences, which may be homopolymeric tracts, short-period repeats, or regions enriched in one or more amino acids. Such low-complexity regions may be aligned between unrelated proteins even though other regions of the protein are entirely dissimilar. A number of low-complexity filter programs can be employed to reduce such low-complexity alignments. For example, the SEG (Wooten and Federhen, (1993) Comput. Chem. 17:149-63) and XNU (Claverie and States, (1993) Comput. Chem. 17:191-201) low-complexity filters can be employed alone or in combination.

As used herein, "sequence identity" or "identity" in the context of two nucleic acid or polypeptide sequences includes reference to the residues in the two sequences, which are the same when aligned for maximum correspondence over a specified comparison window. When percentage of sequence identity is used in reference to proteins it is recognized that residue positions which are not identical often differ by conservative amino acid substitutions, where amino acid residues are substituted for other amino acid residues with similar chemical properties (e.g., charge or hydrophobicity) and therefore do not change the functional properties of the molecule. Where sequences differ in conservative substitutions, the percent sequence identity may be adjusted upwards to correct for the conservative nature of the substitution. Sequences, which differ by such conservative substitutions, are said to have "sequence similarity" or "similarity." Means for making this adjustment are well known to those of skill in the art. Typically this involves scoring a conservative substitution as a partial rather than a full mismatch, thereby increasing the percentage sequence identity. Thus, for example, where an identical amino acid is given a score of 1 and a non-conservative substitution is given a score of zero, a conservative substitution is given a score between zero and 1. The scoring of conservative substitutions is calculated, e.g., according to the algorithm of Meyers and Miller, (1988) Computer Applic. Biol. Sci. 4:11-17, e.g., as implemented in the program PC/GENE (Intelligenetics, Mountain View, Calif., USA).

As used herein, "percentage of sequence identity" means the value determined by comparing two optimally aligned sequences over a comparison window, wherein the portion of the polynucleotide sequence in the comparison window may comprise additions or deletions (i.e., gaps) as compared to the reference sequence (which does not comprise additions or deletions) for optimal alignment of the two sequences. The percentage is calculated by determining the number of positions at which the identical nucleic acid base or amino acid residue occurs in both sequences to yield the number of matched positions, dividing the number of matched positions by the total number of positions in the window of comparison and multiplying the result by 100 to yield the percentage of sequence identity.

The term "substantial identity" or "substantially identical" of polynucleotide sequences means that a polynucleotide comprises a sequence that has between 50-100% sequence identity, preferably at least 50% sequence identity, preferably at least 60% sequence identity, preferably at least 70%, more preferably at least 80%, more preferably at least 90% and most preferably at least 95%, compared to a reference sequence using one of the alignment programs described using standard parameters. One of skill will recognize that these values can be appropriately adjusted to determine corresponding identity of proteins encoded by two nucleotide sequences by taking into account codon degeneracy, amino acid similarity, reading frame positioning and the like. Substantial identity of amino acid sequences for these purposes normally means sequence identity of between 55-100%, preferably at least 55%, preferably at least 60%, more preferably at least 70%, 80%, 90% and most preferably at least 95%.

Development of IDO1 Binding Agents

Antibodies are currently the default detection agent for use in diagnostic platforms. However, antibodies possess several disadvantages, including high cost, poor stability, and, in many cases, lack of proper characterization and high specificity. The ideal replacement for use in diagnostic assays should be synthetic, stable to a range of thermal and chemical conditions, and display high affinity and specificity for the target of interest.

A high quality monoclonal antibody possesses low-nanomolar affinity and high target specificity. Interestingly, structural and genetic analyses of the antigen recognition surface have shown that the majority of the molecular diversity of the variable loops is contained in a single highly variable loop (CDR-H3). In humans, this loop ranges in size from 1-35 residues (15 on average), can adopt a wide range of structural conformations, and is responsible for most of the interactions with the antigen. The other five loops are significantly less diverse and adopt only a handful of conformations. This suggests that a carefully selected "anchor" peptide can dominate the mode and strength of the interaction between a binding agent and its target protein. It also suggests that other peptide components, while providing only modest contributions to the total interaction energy, can supply important scaffolding features and specificity elements.

In situ click chemistry is a technique in which a small molecule enzymatic inhibitor is separated into two moieties, each of which is then expanded into a small library—one containing acetylene functionalities, and the other containing azide groups. The enzyme itself then assembles the 'best fit' inhibitor from these library components by selectively promoting 1,3-dipolar cycloaddition between the acetylene and azide groups to form a triazole linkage (the 'click' reaction). The protein effectively plays the role of an extremely selective variant of the Cu(I) catalyst that is commonly used for such couplings. The enzyme promotes the click reaction only between those library components that bind to the protein in the right orientation. The resultant inhibitor can exhibit far superior affinity characteristics relative to the initial inhibitor that formed the basis of the two libraries.

Sequential in situ click chemistry extends the in situ click chemistry concept to enable the discovery of multiligand capture agents (see: USSN 20100009896, incorporated herein by reference). This process was used previously to produce a triligand capture agent against the model protein carbonic anhydrase II (CAII). Sequential in situ click chemistry has several advantages. First, structural information about the protein target is replaced by the ability to sample a very large chemical space to identify the ligand components of the capture agent. For example, an initial ligand may be identified by screening the protein against a large ($>10^6$ element) one-bead-one-compound (OBOC) peptide library, where the peptides themselves may be comprised of natural, non-natural, and/or artificial amino acids. The resultant anchor ligand is then utilized in an in situ click screen, again using a large OBOC library, to identify a biligand binder. A second advantage is that the process can be repeated, so that the biligand is used as an anchor to identify a triligand, and so forth. The final binding agent can then be scaled up using relatively simple and largely automated chemistries, and it can be developed with a label, such as a biotin group, as an intrinsic part of its structure. This approach permits the exploration of branched, cyclic, and linear binding agent architectures. While many strategies for protein-directed multiligand assembly have been described, most require detailed structural information on the target to guide the screening strategy, and most (such as the original in situ click approach), are optimized for low-diversity small molecule libraries.

IDO1 Capture Agents

In one aspect, provided herein is a stable, synthetic capture agent that specifically binds IDO1, wherein the capture agent comprises one or more "anchor" ligands (also referred to as simply "ligands" herein) and a linker where there are one or more ligands, and wherein the ligands selectively bind IDO1. These are referred to herein as capture agents.

In certain embodiments, a ligand comprises one or more polypeptides or peptides. In certain of these embodiments, a target-binding moiety comprises one or more peptides comprising D-amino acids, L-amino acids, and/or amino acids substituted with functional groups selected from the group consisting of substituted and unsubstituted alkyl, substituted and unsubstituted azido, substituted and unsubstituted alkynyl, substituted and unsubstituted biotinyl, substituted and unsubstituted azidoalkyl, substituted and unsubstituted polyethyleneglycolyl, and substituted and unsubstituted 1,2,3-triazole. In specific embodiments, the ligand comprises a peptide comprising D-amino acids and artificial amino acids.

In certain embodiments, the ligands are linked to one another via a covalent linkage through a linker. In certain of these embodiments, the ligand and linker are linked to one another via an amide bond or a 1,4-disubstituted-1,2,3-triazole linkage as shown below:

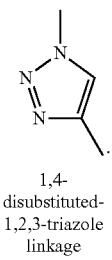

1,4-disubstituted-1,2,3-triazole linkage

In those embodiments where the ligands and linker are linked to one another via a 1,4-disubstituted-1,2,3-triazole linkage, the 1,4-disubstituted-1,2,3-triazole linkage may be formed by Cu-Catalyzed Azide/Alkyne Cycloaddition (CuAAC).

In certain embodiments, the ligands and linker are linked to one another by a Tz4 linkage having the following structure:

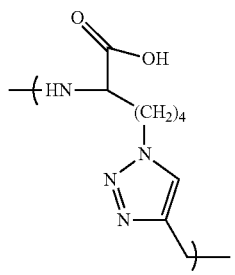

In certain embodiments, the ligands and linker are linked to one another by a Tz5 linkage having the following structure:

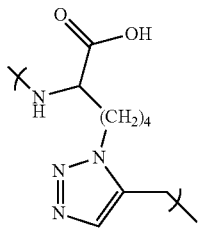

In those embodiments wherein one or more of the ligands and linker are linked to one another via amide bonds, the amide bond may be formed by coupling a carboxylic acid group and an amine group in the presence of a coupling agent (e.g., 0-(7-azabenzotriazol-1-yl)-N,N,N',N'-tetramethyluronium hexafluorophosphate (HATU), N-hydroxy-7-aza-benzotriazole (HOAt), or diisopropylethylamine (DIEA) in DMF).

In certain embodiments, the capture agents provided herein are stable across a range of reaction conditions and/or storage times. A capture agent that is "stable" as used herein maintains the ability to specifically bind to a target protein. In certain embodiments, the capture agents provided herein are more stable than an antibody binding to the same target protein under one or more reaction and/or storage conditions. For example, in certain embodiments the capture agents provided herein are more resistant to proteolytic degradation than an antibody binding to the same target protein.

In certain embodiments, the capture agents provided herein have a shelf-life of greater than six months, meaning that they are stable in storage for greater than six months. In certain of these embodiments, the capture agents have a shelf-life of one year or greater, two years or greater, or more than three years. In certain of these embodiments, the capture agents are stored as a lyophilized powder. In certain embodiments, the capture agents provided herein have a longer shelf-life than an antibody binding to the same target protein.

In certain embodiments, the capture agents provided herein are stable at temperatures ranging from about −80° to about 120° C. In certain of these embodiments, the capture agents are stable within a temperature range of −80° to −40° C.; −40° to −20° C.; −20° to 0° C.; 0° to 20° C.; 20° to 40° C.; 40° to 60° C.; 60° to 80° C.; and/or 80° to 120° C. In certain embodiments, the capture agents provided herein are stable across a wider range of temperatures than an antibody binding to the same target protein, and/or remain stable at a specific temperature for a longer time period than an antibody binding to the same target protein.

In certain embodiments, the IDO1 capture agents provided herein are stable at a pH range from about 3.0 to about 8.0. In certain embodiments, the range is about 4.0 to about 7.0. In certain embodiments, the range is about 7.0 to about 8.0.

In certain embodiments, the IDO1 capture agents provided herein are stable in human serum for more than 12 hours. In certain of these embodiments, the capture agents are stable in human serum for more than 18 hours, more than 24 hours, more than 36 hours, or more than 48 hours. In certain embodiments, the capture agents provided herein are stable for a longer period of time in human serum than an antibody binding to the same target protein. In certain embodiments, the capture agents are stable as a powder for two months at a temperature of about 60° C.

In certain embodiments, the IDO1 capture agents provided herein may comprise one or more detection labels, including for example biotin, copper-1,4,7,10-tetraazacyclododecane-1,4,7,10-tetraacetic acid (copper-DOTA), $^{64}$Cu DOTA, $^{68}$Ga DOTA, $^{18}$F, $^{64}$Cu, $^{68}$Ga, $^{89}$Zr, $^{124}$I, $^{86}$Y, $^{94m}$Tc, $^{110m}$In, 11C, $^{76}$Br, $^{123}$I, $^{131}$I, $^{67}$Ga, $^{111}$In and $^{99m}$Tc, or other radiolabeled products that may include gamma emitters, proton emitters, positron emitters, tritium, or covered tags detectable by other methods (i.e., gadolinium) among others. In a particular embodiment, the detection label is $^{18}$F. The capture agents may be used as diagnostic agents.

In certain embodiments, the IDO1 capture agents provided herein may be modified to obtain a desired chemical or biological activity. Examples of desired chemical or biological activities include, without limitation, improved solubility, stability, bioavailability, detectability, or reactivity. Examples of specific modifications that may be introduced to a capture agent include, but are not limited to, cyclizing the capture agent through formation of a disulfide bond; modifying the capture agent with other functional groups or molecules. Similarly, a capture agent may be synthesized to bind to non-canonical or non-biological epitopes on proteins, thereby increasing their versatility. In certain embodiments, the capture agent may be modified by modifying the synthesis blocks of the target-binding moieties before the coupling reaction.

In certain embodiments, the IDO1 capture agents provided herein are stable across a wide range of temperatures, pH values, storage times, storage conditions, and reaction conditions, and in certain embodiments the imaging agents are more stable than a comparable antibody or biologic. In certain embodiments, the capture agents are stable in storage as a lyophilized powder. In certain embodiment, the capture agents are stable in storage at a temperature of about −80° C. to about 60° C. In certain embodiments, the capture agents are stable at room temperature. In certain embodiments, the capture agents are stable in human serum for at least 24 hours. In certain embodiments, the capture agents are stable at a pH in the range of about 3 to about 12. In certain embodiments, the capture agents are stable as a powder for two months at a temperature of about 60° C.

Methods of Making/Screening Capture Agents

Provided herein in certain embodiments are methods of screening target-binding moieties and/or making imaging agents that comprise these target-binding moieties. Methods for screening target-binding moieties and/or making imaging agents that comprise these target-binding moieties can also be found in International Publication Nos. WO 2012/106671, WO 2013/033561, WO 2013/009869 and WO 2014/074907, each of which is incorporated by reference, herein, in their entireties.

In certain embodiments, two separately-identified ligands that bind to two different regions of the same protein (the target) are chemically linked together to form a biligand. By optimizing a linker of the two ligands, the biligand formed by the ligands and linker can exhibit a binding affinity that is far superior to either of the individual ligands. This enhanced binding effect is called binding cooperativity. For an ideal cooperative binder, the thermodynamic binding energies of the individual ligands to the target will sum to yield the binding energy of the linked biligand. This means that the binding affinity constant ($K_D$) of the linked biligand will be the product of the binding affinity of the individual ligands (i.e. $K_D=K_{D1} \times K_{D2}$, where the subscripts 1 and 2 refer to the two ligands). In practice, full cooperative binding is rarely, if ever, achieved. Thus, a comparison of the properties of a linked biligand against those of a fully cooperative binder provides a measurement of how optimally the two ligands were linked.

If the protein target has a known and well-defined tertiary (folded) structure, then key aspects of this targeting method involve strategies for identifying ligands that bind to preferred regions of the protein, followed by approaches for identifying an optimized linker. If the protein does not have a well-defined tertiary structure, the disclosure describes strategies designed to still achieve a significant measure of cooperative binding from a biligand.

For developing a set of PCC binders against a target protein, first one or more PCCs that bind an epitope on the target protein are identified. Optionally, one or more different PCCs binding to a second epitope are identified. Additional PCCs that bind to a third, fourth, etc., epitope may be useful as well. The epitope targeted PCC method teaches that this may be accomplished by screening peptide libraries against synthetic epitopes (SynEps). A SynEp is a polypeptide that has the sequence of the naturally occurring target epitope, except that one position contains an artificial amino acid that presents an azide or acetylene chemical group, called a click handle. The SynEp is further modified to contain an assay handle, such as a biotin group, at the N- or C-terminus. The screening procedure can be done using any procedure disclosed herein or known in the art. By screening, one identifies at least one unique peptide binder to each of at least two epitopes on the target. Those peptide binders are validated via carrying out binding assays against the full protein target as well as against the SynEps. For those binding assays, the SynEps are prepared with the naturally occurring residue in place of the click handle.

Ideally, the different regions of the target protein to which the different ligands bind will be relatively close together (a few nanometers or less) in the tertiary protein structure. For even a single SynEp, a screen can produce PCCs that bind to two different sites. During the SynEp screening steps, PCCs that bind to the N-terminal side of the epitope or the C-terminal side may both be identified.

Once the epitope targeted PCCs are identified, there are several methods for selecting a linker.

In a first embodiment, if the folded structure of the protein is known, and if the PCCs bind to that folded structure, then one can use that information, plus knowledge of which PCCs bind to which epitopes, to estimate an optimal linker length. Analysis of the binding arrangement, together with the structure of the protein from, for example, the Protein Data Bank, permits an estimate of the length of an optimized linker. Such an estimate can narrow down the choice of candidate linkers to a very small number. One example might be to use such a length estimate to select one or two length-matched polyethylene glycol oligomers for testing. The best linker is the one that brings the biligand affinity closest to that a fully cooperative binder.

In a second embodiment, if the folded structure of the protein is not known, or if the protein simply does not have a well-defined folded structure, then one uses as much information as is available to determine the composition of a library of candidate linker molecules. That library is then screened to identify a best linker.

In a third embodiment, if the folded structure of the protein is not known or if the protein simply does not have a well-defined folded structure, then, using what knowledge about the protein does exist, simply select a linker to append the two PCCs. Even if an optimized, fully cooperative binder is not identified in this way, the linked biligand will almost certainly outperform either of the two monoligands because of cooperativity effects.

In certain embodiments, linkers can include polyethylene glycol (PEG), alkane, alkene, triazole, amide, or peptides.

In Vitro

For detection of IDO1 in solution, a binding or capture agent as described herein can be detectably labeled to form an imaging agent, then contacted with the solution, and thereafter formation of a complex between the imaging agent and the IDO1 target can be detected. As an example, a fluorescently labeled imaging agent can be used for in vitro IDO1 detection assays, wherein the imaging agent is added to a solution to be tested for IDO1 under conditions allowing binding to occur. The complex between the fluorescently labeled imaging agent and the IDO1 target can be detected and quantified by, for example, measuring the increased fluorescence polarization arising from the complex-bound peptide relative to that of the free peptide.

Alternatively, a sandwich-type "ELISA" assay can be used, wherein a imaging agent is immobilized on a solid support such as a plastic tube or well, then the solution suspected of containing IDO1 is contacted with the immobilized binding moiety, non-binding materials are washed away, and complexed polypeptide is detected using a suitable detection reagent for recognizing IDO1.

For detection or purification of soluble IDO1 from a solution, imaging agents of the invention can be immobilized on a solid substrate such as a chromatographic support or other matrix material, then the immobilized binder can be loaded or contacted with the solution under conditions suitable for formation of an imaging agent/IDO1 complex. The non-binding portion of the solution can be removed and the complex can be detected, for example, using an anti-IDO1 antibody, or an anti-binding polypeptide antibody, or the IDO1 can be released from the binding moiety at appropriate elution conditions.

In Vivo Diagnostic Imaging

A particularly preferred use for the imaging agents of the invention is for creating visually readable images of IDO1 or IDO1-expressing cells in a biological fluid, such as, for example, in human serum. The IDO1 imaging agents disclosed herein can be conjugated to a label appropriate for diagnostic detection. Preferably, an imaging agent exhibiting much greater specificity for IDO1 than for other serum proteins is conjugated or linked to a label appropriate for the detection methodology to be employed. For example, the imaging agent can be conjugated with or without a linker to a paramagnetic chelate suitable for Magnetic Resonance Imaging (MRI), with a radiolabel suitable for x-ray, Positron Emission Tomography (PET), Single Photon Emission Computed Tomography (SPECT) or scintigraphic imaging (including a chelator for a radioactive metal), with an ultrasound contrast agent (e.g., a stabilized microbubble, a microballoon, a microsphere or what has been referred to as a gas filled "liposome") suitable for ultrasound detection, or with an optical imaging dye.

In another embodiment, rather than directly labeling an imaging agent with a detectable label or radiotherapeutic construct, one or more peptides or constructs of the invention can be conjugated with for example, avidin, biotin, or an antibody or antibody fragment that will bind the detectable label or radiotherapeutic.

A. Magnetic Resonance Imaging

The IDO1 imaging agents described herein can advantageously be conjugated with a paramagnetic metal chelate in order to form a contrast agent for use in MRI.

Preferred paramagnetic metal ions have atomic numbers 21-29, 42, 44, or 57-83. This includes ions of the transition metal or lanthanide series which have one, and more preferably five or more, unpaired electrons and a magnetic moment of at least 1.7 Bohr magneton. Preferred paramagnetic metals include, but are not limited to, chromium (III), manganese (II), manganese (III), iron (II), iron (III), cobalt (II), nickel (II), copper (II), praseodymium (III), neodymium (III), samarium (III), gadolinium (III), terbium (III), dysprosium (III), holmium (III), erbium (III), europium (III) and ytterbium (III), chromium (III), iron (III), and gadolinium (III). The trivalent cation, Gd3+, is particularly preferred for MRI contrast agents, due to its high relaxivity and low toxicity, with the further advantage that it exists in only one biologically accessible oxidation state, which minimizes undesired metabolism of the metal by a patient. Another useful metal is Cr3+, which is relatively inexpensive. Gd(III) chelates have been used for clinical and radiologic MR applications since 1988, and approximately 30% of MRI exams currently employ a gadolinium-based contrast agent.

The paramagnetic metal chelator is a molecule having one or more polar groups that act as a ligand for, and complex with, a paramagnetic metal. Suitable chelators are known in the art and include acids with methylene phosphonic acid groups, methylene carbohydroxamine acid groups, carboxyethylidene groups, or carboxymethylene groups. Examples of chelators include, but are not limited to, diethylenetriaminepentaacetic acid (DTPA), 1,4,7,10-tetraazacyclotetradecane-1,4,7,10-tetraacetic acid (DOTA), 1-substituted 1,4,7-tricarboxymethyl-1,4,7,10-teraazacyclododecane (DO3A), ethylenediaminetetraacetic acid (EDTA), and 1,4,8,11-tetraazacyclotetradecane-1,4,8,11-tetraacetic acid (TETA). Additional chelating ligands are ethylene bis-(2-hydroxy-phenylglycine) (EHPG), and derivatives thereof, including 5-CI-EHPG, 5-Br-EHPG, 5-Me-EHPG, 5-t-Bu-EHPG, and 5-sec-Bu-EHPG; benzodiethylenetriamine pentaacetic acid (benzo-DTPA) and derivatives thereof, including dibenzo-DTPA, phenyl-DTPA, diphenyl-DTPA, benzyl-DTPA, and dibenzyl DTPA; bis-2 (hydroxybenzyl)-ethylene-diaminediacetic acid (HBED) and derivatives thereof; the class of macrocyclic compounds which contain at least 3 carbon atoms, more preferably at least 6, and at least two heteroatoms (0 and/or N), which macrocyclic compounds can consist of one ring, or two or three rings joined together at the hetero ring elements, e.g., benzo-DOTA, dibenzo-DOTA, and benzo-NOTA, where NOTA is 1,4,7-triazacyclononane N,N',N"-triacetic acid, benzo-TETA, benzo-DOTMA, where DOTMA is 1,4,7,10-tetraazacyclotetradecane-1,4,7,10-tetra(methyl tetraacetic acid), and benzo-TETMA, where TETMA is 1,4,8,11-tetraazacyclotetradecane-1,4,8,11-(methyl tetraacetic acid); derivatives of 1,3-propylene-diaminetetraacetic acid (PDTA) and triethylenetetraaminehexaacetic acid (TTNA); derivatives of 1,5,10-N,N',N"-tris(2,3-dihydroxybenzoyl)-tricatecholate (LICAM); and 1,3,5-N,N',N"-tris(2,3-dihydroxybenzoyl)aminomethylbenzene (MECAM). A preferred chelator for use in the present invention is DTPA, and the use of DO3A is particularly preferred. Examples of representative chelators and chelating groups contemplated by the present invention are described in WO 98/18496, WO 86/06605, WO 91/03200, WO 95/28179, WO 96/23526, WO 97/36619, PCT/US98/01473, PCT/US98/20182, and U.S. Pat. Nos. 4,899,755, 5,474,756, 5,846,519 and 6,143,274, all of which are hereby incorporated by reference.

In accordance with the present disclosure, the chelator of the MRI contrast agent is coupled to the IDO1 imaging agent. The positioning of the chelate should be selected so as not to interfere with the binding affinity or specificity of the IDO1 imaging agent. The chelate also can be attached anywhere on the imaging agent.

In general, the IDO1 imaging agent can be bound directly or covalently to the metal chelator (or other detectable label), or it can be coupled or conjugated to the metal chelator using a linker, which can be, without limitation, amide, urea, acetal, ketal, double ester, carbonyl, carbamate, thiourea, sulfone, thioester, ester, ether, disulfide, lactone, imine, phosphoryl, or phosphodiester linkages; substituted or unsubstituted saturated or unsaturated alkyl chains; linear, branched, or cyclic amino acid chains of a single amino acid or different amino acids (e.g., extensions of the N- or C-terminus of the IDO1 binding moiety); derivatized or underivatized polyethylene glycols (PEGs), polyoxyethylene, or polyvinylpyridine chains; substituted or unsubstituted polyamide chains; derivatized or underivatized polyamine, polyester, polyethylenimine, polyacrylate, poly(vinyl alcohol), polyglycerol, or oligosaccharide (e.g., dextran) chains; alternating block copolymers; malonic, succinic, glutaric, adipic and pimelic acids; caproic acid; simple diamines and dialcohols; any of the other linkers disclosed herein; or any other simple polymeric linkers known in the art (see, for example, WO 98/18497 and WO 98/18496). Preferably the molecular weight of the linker can be tightly controlled. The molecular weights can range in size from less than 100 to greater than 1000. Preferably the molecular weight of the linker is less than 100. In addition, it can be desirable to utilize a linker that is biodegradable in vivo to provide efficient routes of excretion for the imaging reagents of the present invention. Depending on their location within the linker, such biodegradable functionalities can include ester, double ester, amide, phosphoester, ether, acetal, and ketal functionalities.

In general, known methods can be used to couple the metal chelate and the IDO1 imaging agent using such linkers (WO 95/28967, WO 98/18496, WO 98/18497 and discussion therein). The IDO1 binding moiety can be linked through an N- or C-terminus via an amide bond, for example, to a metal coordinating backbone nitrogen of a metal chelate or to an acetate arm of the metal chelate itself. The present disclosure contemplates linking of the chelate on any position, provided the metal chelate retains the ability to bind the metal tightly in order to minimize toxicity.

MRI contrast reagents prepared according to the disclosures herein can be used in the same manner as conventional MRI contrast reagents. Certain MR techniques and pulse sequences can be preferred to enhance the contrast of the site to the background blood and tissues. These techniques include (but are not limited to), for example, black blood angiography sequences that seek to make blood dark, such as fast spin echo sequences (Alexander, A. et al., 1998. Magn. Reson. Med., 40: 298-310) and flow-spoiled gradient echo sequences (Edelman, R. et al., 1990. Radiology, 177: 45-50). These methods also include flow independent techniques that enhance the difference in contrast, such as inversion-recovery prepared or saturation-recovery prepared sequences that will increase the contrast between IDO1-expressing tissue and background tissues. Finally, magnetization transfer preparations also can improve contrast with these agents (Goodrich, K. et al., 1996. Invest. Radia, 31: 323-32).

The labeled reagent is administered to the patient in the form of an injectable composition. The method of administering the MRI contrast agent is preferably parenterally, meaning intravenously, intraarterially, intrathecally, interstitially, or intracavitarilly. For imaging IDO1-expressing tissues, such as tumors, intravenous or intraarterial administration is preferred. For MRI, it is contemplated that the subject will receive a dosage of contrast agent sufficient to enhance the MR signal at the site IDO1 expression by at least 10%. After injection with the IDO1 imaging agent containing MRI reagent, the patient is scanned in the MRI machine to determine the location of any sites of IDO1 expression. In therapeutic settings, upon identification of a site of IDO1 expression (e.g., fluid or tissue), an anti-cancer agent (e.g., inhibitors of IDO1) can be immediately administered, if necessary, and the patient can be subsequently scanned to visualize viral load.

B. Nuclear Imaging (Radionuclide Imaging) and Radiotherapy

The IDO1 imaging agents of the invention can be conjugated with a radionuclide reporter appropriate for scintigraphy, SPECT, or PET imaging and/or with a radionuclide appropriate for radiotherapy. Constructs in which the IDO1 imaging agents are conjugated with both a chelator for a radionuclide useful for diagnostic imaging and a chelator useful for radiotherapy are within the scope of the invention.

For use as a PET agent a disclosed imaging agent may be complexed with one of the various positron emitting metal ions, such as $^{51}Mn$, $^{52}Fe$, $^{60}Cu$, $^{68}Ga$, $^{72}As$, $^{94m}Tc$, or $^{110}In$. The binding moieties of the invention can also be labeled by halogenation using radionuclides such as $^{18}F$, $^{124}I$, $^{125}I$, $^{131}I$, $^{123}I$, $^{77}Br$, and $^{76}Br$. Preferred metal radionuclides for scintigraphy or radiotherapy include $^{99m}Tc$, $^{51}Cr$, $^{67}Ga$, $^{68}Ga$, $^{47}Sc$, $^{51}Cr$, $^{167}Tm$, $^{141}Ce$, $^{111}In$, $^{168}Yb$, $^{175}Yb$, $^{140}La$, $^{90}Y$, $^{88}Y$, $^{153}Sm$, $^{166}Ho$, $^{165}Dy$, $^{166}Dy$, $^{62}Cu$, $^{64}Cu$, $^{67}Cu$, $^{97}Ru$, $^{103}Ru$, $^{186}Re$, $^{188}Re$, $^{203}Pb$, $^{211}Bi$, $^{212}Bi$, $^{213}Bi$, $^{214}Bi$, $^{105}Rh$, $^{109}Pd$, $^{117m}Sn$, $^{149}Pm$, $^{161}Tb$, $^{177}Lu$, $^{198}Au$ and $^{199}Au$. The choice of metal will be determined based on the desired therapeutic or diagnostic application. For example, for diagnostic purposes the preferred radionuclides include $^{64}Cu$, $^{67}Ga$, $^{68}Ga$, $^{99m}Tc$, and $^{111}In$. For therapeutic purposes, the preferred radionuclides include $^{64}Cu$, $^{90}Y$, $^{105}Rh$, $^{111}In$, $^{117m}Sn$, $^{149}Pm$, $^{153}Sm$, $^{161}Tb$, $^{166}Tb$, $^{166}Dy$, $^{166}Ho$, $^{175}Yb$, $^{177}Ln$, $^{186/188}Re$, and $^{199}Au$. $^{99m}Tc$ is useful for diagnostic applications because of its low cost, availability, imaging properties, and high specific activity. The nuclear and radioactive properties of $^{99m}Tc$ make this isotope an ideal scintigraphic imaging agent. This isotope has a single photon energy of 140 keV and a radioactive half-life of about 6 hours, and is readily available from a $^{99}Mo$-$^{99m}Tc$ generator. $^{18}F$, 4-[$^{18}F$]fluorobenzaldehyde ($^{18}FB$), Al[$^{18}F$]-NOTA, $^{68}Ga$-DOTA, and $^{68}Ga$-NOTA are typical radionuclides for conjugation to IDO1 imaging agents for diagnostic imaging.

The metal radionuclides may be chelated by, for example, linear, macrocyclic, terpyridine, and $N_3S$, $N_2S_2$, or $N_4$ chelants (see also, U.S. Pat. Nos. 5,367,080, 5,364,613, 5,021,556, 5,075,099, 5,886,142), and other chelators known in the art including, but not limited to, HYNIC, DTPA, EDTA, DOTA, DO3A, TETA, NOTA and bisamino bisthiol (BAT) chelators (see also U.S. Pat. No. 5,720,934). For example, N.sub.4 chelators are described in U.S. Pat. Nos. 6,143,274; 6,093,382; 5,608,110; 5,665,329; 5,656,254; and 5,688,487. Certain N.sub.35 chelators are described in PCT/CA94/00395, PCT/CA94/00479, PCT/CA95/00249 and in U.S. Pat. Nos. 5,662,885; 5,976,495; and 5,780,006. The chelator also can include derivatives of the chelating ligand mercapto-acetyl-acetyl-glycyl-glycine (MAG3), which contains an $N_3S$, and $N_2S_2$ systems such as MAMA (monoamidemonoaminedithiols), DADS ($N_2S$ diaminedithiols), CODADS and the like. These ligand systems and a variety of others are described in, for example, Liu, S, and Edwards, D., 1999. Chem. Rev., 99:2235-2268, and references therein.

The chelator also can include complexes containing ligand atoms that are not donated to the metal in a tetradentate array. These include the boronic acid adducts of technetium and rhenium dioximes, such as are described in U.S. Pat. Nos. 5,183,653; 5,387,409; and 5,118,797, the disclosures of which are incorporated by reference herein, in their entirety.

The chelators can be covalently linked directly to the IDO1 imaging agent via a linker, as described previously, and then directly labeled with the radioactive metal of choice (see, WO 98/52618, U.S. Pat. Nos. 5,879,658, and 5,849,261).

IDO1 imaging agents comprising $^{18}F$, 4-[$^{18}F$]fluorobenzaldehyde ($^{18}FB$), Al[$^{18}F$]-NOTA, $^{68}Ga$-DOTA, and $^{68}Ga$-NOTA are of preferred interest for diagnostic imaging. Complexes of radioactive technetium are also useful for diagnostic imaging, and complexes of radioactive rhenium are particularly useful for radiotherapy. In forming a complex of radioactive technetium with the reagents of this invention, the technetium complex, preferably a salt of $^{99m}Tc$ pertechnetate, is reacted with the reagent in the presence of a reducing agent. Preferred reducing agents are dithionite, stannous and ferrous ions; the most preferred reducing agent is stannous chloride. Means for preparing such complexes are conveniently provided in a kit form comprising a sealed vial containing a predetermined quantity of a reagent of the invention to be labeled and a sufficient amount of reducing agent to label the reagent with $^{99m}Tc$. Alternatively, the complex can be formed by reacting a peptide of this invention conjugated with an appropriate chelator with a pre-formed labile complex of technetium and another compound known as a transfer ligand. This process is known as ligand exchange and is well known to those skilled in the art. The labile complex can be formed using such transfer ligands as tartrate, citrate, gluconate or mannitol, for example. Among the $^{99m}Tc$ pertechnetate salts useful with the present invention are included the alkali metal salts such as the sodium salt, or ammonium salts or lower alkyl ammonium salts.

Preparation of the complexes of the present invention where the metal is radioactive rhenium can be accomplished using rhenium starting materials in the +5 or +7 oxidation state. Examples of compounds in which rhenium is in the Re(VII) state are $NH_4ReO_4$ or $KReO_4$. Re(V) is available as, for example, [$ReOCl_4$]($NBu_4$), [$ReOCl_4$]($AsPh_4$), $ReOCl_3$($PPh_3$)$_2$ and as $ReO_2$(pyridine)$^{4+}$, where Ph is phenyl and Bu is n-butyl. Other rhenium reagents capable of forming a rhenium complex also can be used.

Radioactively labeled PET, SPECT, or scintigraphic imaging agents provided by the present invention are encompassed having a suitable amount of radioactivity. Generally, the unit dose to be administered has a radioactivity of about 0.01 mCi to about 100 mCi, preferably 1 mCi to 20 mCi. The solution to be injected at unit dosage is from about 0.01 mL to about 10 mL. It is generally preferred to form radioactive complexes in solutions containing radioactivity at concentrations of from about 0.01 mCi to 100 mCi per mL.

Typical doses of a radionuclide-labeled IDO1 imaging agent according to the invention provide 10-20 mCi. After injection of the radionuclide-labeled IDO1 imaging agents into the patient, a gamma camera calibrated for the gamma ray energy of the nuclide incorporated in the imaging agent is used to image areas of uptake of the agent and quantify the amount of radioactivity present in the site. Imaging of the site in vivo can take place in a matter of a few minutes. However, imaging can take place, if desired, in hours or even longer, after the radiolabeled peptide is injected into a patient. In most instances, a sufficient amount of the administered dose will accumulate in the area to be imaged within about 0.1 of an hour to permit the taking of scintiphotos.

Proper dose schedules for the radiotherapeutic compounds of the present invention are known to those skilled in the art. The compounds can be administered using many methods including, but not limited to, a single or multiple IV or IP injections, using a quantity of radioactivity that is sufficient to cause damage or ablation of the targeted IDO1-expressing tissue, but not so much that substantive damage is caused to non-target (normal tissue). The quantity and dose required is different for different constructs, depending on the energy and half-life of the isotope used, the degree of uptake and clearance of the agent from the body and the mass of the IDO1-expressing tissue. In general, doses can range from a single dose of about 30-50 mCi to a cumulative dose of up to about 3 Ci.

The radiotherapeutic compositions of the invention can include physiologically acceptable buffers, and can require radiation stabilizers to prevent radiolytic damage to the compound prior to injection. Radiation stabilizers are known to those skilled in the art, and can include, for example, para-aminobenzoic acid, ascorbic acid, gentistic acid and the like.

A single, or multi-vial kit that contains all of the components needed to prepare the complexes of this invention, other than the radionuclide, is an integral part of this invention.

A single-vial kit preferably contains a chelating ligand, a source of stannous salt, or other pharmaceutically acceptable reducing agent, and is appropriately buffered with pharmaceutically acceptable acid or base to adjust the pH to a value of about 3 to about 9. The quantity and type of reducing agent used would depend on the nature of the exchange complex to be formed. The proper conditions are well known to those that are skilled in the art. It is preferred that the kit contents be in lyophilized form. Such a single vial kit can optionally contain labile or exchange ligands such as glucoheptonate, gluconate, mannitol, malate, citric or tartaric acid and can also contain reaction modifiers such as diethylenetriamine-pentaacetic acid (DPTA), ethylenediamine tetraacetic acid (EDTA), or .alpha., .beta., or .gamma. cyclodextrin that serve to improve the radiochemical purity and stability of the final product. The kit also can contain stabilizers, bulking agents such as mannitol, that are designed to aid in the freeze-drying process, and other additives known to those skilled in the art.

A multi-vial kit preferably contains the same general components but employs more than one vial in reconstituting the radiopharmaceutical. For example, one vial can contain all of the ingredients that are required to form a labile Tc(V) complex on addition of pertechnetate (e.g., the stannous source or other reducing agent). Pertechnetate is added to this vial, and after waiting an appropriate period of time, the contents of this vial are added to a second vial that contains the ligand, as well as buffers appropriate to adjust the pH to its optimal value. After a reaction time of about 5 to 60 minutes, the complexes of the present invention are formed. It is advantageous that the contents of both vials of this multi-vial kit be lyophilized. As above, reaction modifiers, exchange ligands, stabilizers, bulking agents, etc. can be present in either or both vials.

Also provided herein is a method to incorporate an $^{18}$F radiolabeled prosthetic group onto an IDO1 imaging agent. In one embodiment, 4-[$^{18}$F]fluorobenzaldehyde ($^{18}$FB) is conjugated onto an imaging agent bearing an aminooxy moiety, resulting in oxime formation. In another embodiment, [$^{18}$F]fluorobenzaldehyde is conjugated onto an imaging agent bearing an acyl hydrazide moiety, resulting in a hydrazone adduct. 4-Fluorobenzaldehyde, can be prepared in $^{18}$F form by displacement of a leaving group, using $^{18}$F ion, by known methods.

$^{18}$F-labeled imaging agents can also be prepared from imaging agents possessing thiosemicarbazide moieties under conditions that promote formation of a thiosemicarbozone, or by use of a $^{18}$F-labeled aldehyde bisulfite addition complex.

The above methods are particularly amenable to the labeling of imaging agents, e.g., the imaging agents described herein, which can be modified during synthesis to contain a nucleophilic hydroxylamine, thiosemicarbazide or hydrazine (or acyl hydrazide) moiety that can be used to react with the labeled aldehyde. The methods can be used for any imaging agent that can accommodate a suitable nucleophilic moiety. Typically the nucleophilic moiety is appended to the N-terminus of the peptide, but the skilled artisan will recognize that the nucleophile also can be linked to an amino acid side chain or to the peptide C-terminus. Methods of synthesizing a radiolabeled peptide sequence are provided in which 4-[$^{18}$F]fluorobenzaldehyde is reacted with a peptide sequence comprising either a hydroxylamine, a thiosemicarbazide or a hydrazine (or acyl hydrazide) group, thereby forming the corresponding oximes, thiosemicarbazones or hydrazones, respectively. The 4-[$^{18}$F]fluorobenzaldehyde typically is generated in situ by the acid-catalyzed decomposition of the addition complex of 4-[$^{18}$F]fluorobenzaldehyde and sodium bisulfite. The use of the bisulfite addition complex enhances the speed of purification since, unlike the aldehyde, the complex can be concentrated to dryness. Formation of the complex is also reversible under acidic and basic conditions. In particular, when the complex is contacted with a peptide containing a hydroxylamine, a thiosemicarbazide or a hydrazine (or acyl hydrazide) group in acidic medium, the reactive free 4-[$^{18}$F]fluorobenzaldehyde is consumed as it is formed in situ, resulting in the corresponding $^{18}$F radiolabeled peptide sequence.

In the instances when the oxime, thiosemicarbazone or hydrazone linkages present in vivo instability, an additional reduction step may be employed to reduce the double bond connecting the peptide to the $^{18}$F bearing substrate. The corresponding reduced peptide linkage would enhance the stability. One of skill in the art would appreciate the variety of methods available to carry out such a reduction step. Reductive amination steps as described in Wilson et al., Journal of Labeled Compounds and Radiopharmaceuticals, XXVIII (10), 1189-1199, 1990 may also be used to form a Schiff's base involving a peptide and 4-[$^{18}$F]fluorobenzaldehyde and directly reducing the Schiff's base using reducing agents such as sodium cyanoborohydride.

The 4-[$^{18}$F]fluorobenzaldehyde may be prepared as described in Wilson et al., Journal of Labeled Compounds and Radiopharmaceuticals, XXVIII (10), 1189-1199, 1990; Iwata et al., Applied radiation and isotopes, 52, 87-92, 2000; Poethko et al., The Journal of Nuclear Medicine, 45, 892-902, 2004; and Schottelius et al., Clinical Cancer Research, 10, 3593-3606, 2004. The Na$^{18}$F in water may be added to a mixture of Kryptofix and $K_2CO_3$. Anhydrous acetonitrile may be added and the solution is evaporated in a heating block under a stream of argon. Additional portions of acetonitrile may be added and evaporated to completely dry the sample. The 4-trimethylammoniumbenzaldehyde triflate may be dissolved in DMSO and added to the dried F-18. The solution may then be heated in the heating block. The solution may be cooled briefly, diluted with water and filtered through a Waters®. Oasis HLB LP extraction cartridge. The cartridge may be washed with 9:1 water:acetonitrile and water to remove unbound $^{18}$F and unreacted 4-trimethylammoniumbenzaldehyde triflate. The 4-[$^{18}$F] fluorobenzaldehyde may then be eluted from the cartridge with methanol in fractions.

Therapeutic Applications

Provided herein in certain embodiments are methods of using the IDO1 binding and capture agents disclosed herein to identify, detect, quantify, and/or separate IDO1 in a biological sample. In certain embodiments, these methods utilize an immunoassay, with the capture agent replacing an antibody or its equivalent. In certain embodiments, the immunoassay may be a Western blot, pull-down assay, dot blot, or ELISA.

A biological sample for use in the methods provided herein may be selected from the group consisting of organs, tissue, bodily fluids, and cells. Where the biological sample is a bodily fluid, the fluid may be selected from the group consisting of blood, serum, plasma, urine, sputum, saliva, stool, spinal fluid, cerebral spinal fluid, lymph fluid, skin secretions, respiratory secretions, intestinal secretions, genitourinary tract secretions, tears, and milk. The organs include, e.g., the adrenal glands, bladder, bones, brain, breasts, cervix, esophagus, eyes, gall bladder, genitals, heart, kidneys, large intestine, liver, lungs, lymph nodes, ovaries, pancreas, pituitary gland, prostate, salivary glands, skeletal muscles, skin, small intestine, spinal cord, spleen, stomach, thymus gland, trachea, thyroid, testes, ureters, and urethra. Tissues include, e.g., epithelial, connective, nervous, and muscle tissues.

Provided herein in certain embodiments are methods of using the IDO1 imaging agents disclosed herein to diagnose and/or classify (e.g., stage) a condition associated with IDO1 expression. In certain of these embodiments, the methods comprise (a) obtaining a biological sample from a subject; (b) measuring the presence or absence of IDO1 in the sample with the IDO1 imaging agent; (c) comparing the levels of IDO1 to a predetermined control range for IDO1; and (d) diagnosing a condition associated with IDO1 expression based on the difference between IDO1 levels in the biological sample and the predetermined control.

In other embodiments, the IDO1 capture agents disclosed herein are used as a mutant specific targeted therapeutic. In certain aspects of this embodiment, the IDO1 capture agent is administered alone without delivering DNA, a radiopharmaceutical or another active agent.

The IDO capture agents described herein also can be used to target genetic material to IDO1 expressing cells. The genetic material can include nucleic acids, such as RNA or DNA, of either natural or synthetic origin, including recombinant RNA and DNA and antisense RNA and DNA. Types of genetic material that can be used include, for example, genes carried on expression vectors such as plasmids, phagemids, cosmids, yeast artificial chromosomes (YACs) and defective or "helper" viruses, antigene nucleic acids, both single and double stranded RNA and DNA and analogs thereof, such as phosphorothioate and phosphorodithioate oligodeoxynucleotides. Additionally, the genetic material can be combined, for example, with lipids, proteins or other polymers. Delivery vehicles for genetic material can include, for example, a virus particle, a retroviral or other gene therapy vector, a liposome, a complex of lipids (especially cationic lipids) and genetic material, a complex of dextran derivatives and genetic material, etc.

In an embodiment the capture agents of the invention are utilized in gene therapy. In this embodiment, genetic material, or one or more delivery vehicles containing genetic material can be conjugated to one or more IDO1 capture agents of this disclosure and administered to a patient.

Therapeutic agents and the IDO1 capture agents disclosed herein can be linked or fused in known ways, optionally using the same type of linkers discussed elsewhere in this application. Preferred linkers will be substituted or unsubstituted alkyl chains, amino acid chains, polyethylene glycol chains, and other simple polymeric linkers known in the art. More preferably, if the therapeutic agent is itself a protein, for which the encoding DNA sequence is known, the therapeutic protein and IDO1 binding polypeptide can be coexpressed from the same synthetic gene, created using recombinant DNA techniques, as described above. The coding sequence for the IDO1 binding polypeptide can be fused in frame with that of the therapeutic protein, such that the peptide is expressed at the amino- or carboxy-terminus of the therapeutic protein, or at a place between the termini, if it is determined that such placement would not destroy the required biological function of either the therapeutic protein or the IDO1 binding polypeptide. A particular advantage of this general approach is that concatamerization of multiple, tandemly arranged IDO1 capture agents is possible, thereby increasing the number and concentration of IDO1 binding sites associated with each therapeutic protein. In this manner, IDO1 binding avidity is increased, which would be expected to improve the efficacy of the recombinant therapeutic fusion protein.

The following examples are provided to better illustrate the claimed invention and are not to be interpreted as limiting the scope of the invention. To the extent that specific materials are mentioned, it is merely for purposes of illustration and is not intended to limit the invention. One skilled in the art may develop equivalent means or reactants without the exercise of inventive capacity and without departing from the scope of the invention.

EXAMPLES

Example 1: IDO1 Epitope Design

Using the crystal structure of human IDO1 (PDB ID: 5EK3), two epitopes (IDO1 Epitope1 and IDO1 Epitope2) were identified in the heme-containing active site of IDO1, which would serve as good candidates for Synthetic Epitope Targeting (FIG. 1A). These two epitopes are located within 11 to 38 Å of each other near the active site of IDO1. An additional epitope (IDO1 Epitope3) that is located on the other side of the IDO1 protein from Epitope1N was designed against the protein surface (FIG. 1B). They were deemed suitable epitopes for PCC agent development based on the following criteria:

Epitope is a continuous sequence (8 to 30 amino acids).

Epitope occurs in a region of the protein that is accessible in the native folded structure.

Epitopes are separated by short distances.

High homologies are demonstrated between the human and mouse IDO1 sequences.

The sequences of IDO1 Epitope1, IDO1 Epitope2, and IDO1 Epitope3 are shown in FIG. 1C. The high homology between the human and mouse IDO1 proteins was leveraged to design epitopes lying in the overlapping region. The primary sequences of human and mouse IDO1 show 62.5% identity (83.8% similarity) in 395 a.a. overlap.

Each epitope was synthesized to include an azide click handle (Az4=L-azidolysine) at a selected internal amino acid location. For IDO1 Epitope3, the D149Az4 substitution was made as it is located in the middle of the exposed loop of interest. For IDO1 Epitope1 and Epitope2, the F259Az4 and L131Az4 substitutions were made because they are adjacent to the residues key to substrate binding. The active site residues of G262-A264 (IDO1 Epitope1) and Y126-V130 (IDO1 Epitope2) are highlighted in FIG. 1C. Because the azide click handle was installed as a centrally located residue, screening each epitope could yield two sets of epitope-targeted macrocyclic peptide ligands—one set pointing towards the N-terminus and another set pointing towards the C-terminus of the epitope. Epitopes 1C and 2N contain residues forming the active site pockets, while the Epitopes 1N and 2C can be found on the surface of the IDO1 protein.

Example 2: Screening a Macrocycle Library Against IDO1 Epitopes 1, 2, and 3

Screens were performed against human IDO1 epitopes that show high homology with mouse IDO1 with the goal of identifying leads that show equivalent binding to the human and mouse IDO1 proteins. The library was composed exclusively of amino acids with D-chirality and artificial amino acids, and contained all possible combinations of pentapeptide (5-mer) sequences in the variable region. Standard Fmoc-amino acid coupling chemistries and solid-phase synthesis were used. The diversity of the macrocycle D-amino acid library was expanded by including 4-fluoro-L-phenylalanine (F-Phe) to assist in cell penetration and 1-methyl-L-tryptophan (Me-Trp) to help in biasing the screen towards hits that recognize the IDO1 active site.

Screens were performed using a triazole-cyclized OBOC library of the form $H_2N$-Pra-Cy(XXXXX-click)-(D-Met)-TG, where TG=TentaGel® S $NH_2$ resin (S 30 902, Rapp Polymere), Pra=L-propargylglycine (alkyne click handle), D-Met=D-methionine, and X=one of sixteen D-amino acids (D-Ala, D-Arg, D-Asn, D-Asp, D-Glu, Gly, D-His, D-Leu, D-Lys, D-Phe, D-Pro, D-Ser, D-Thr, D-Trp, D-Tyr, D-Val), 4-fluoro-L-phenylalanine (F-Phe), or 1-methyl-L-tryptophan (Me-Trp). The notation Cy(XXXXX-click) indicates that macrocycles were closed using Cu-catalyzed azide-alkyne cycloaddition (CuAAC). Macrocycles were identified against the three synthesized IDO1 epitopes in a five-step screening process: 1) a pre-clear to eliminate non-specific binders, 2) a product screen to identify hits resulting from IDO1 Epitope1-templated in situ click chemistry, 3) another product screen to identify hits resulting from IDO1 Epitope2-templated in situ click chemistry, 4) a further product screen to identify hits resulting from IDO1 Epitope3-templated in situ click chemistry, and 5) a target screen against His-tagged IDO1 human recombinant protein to identify peptides that bind to the protein as well as the epitopes.

Pre-Clear.

Swelled library beads (750 mg) were blocked overnight with Blocking Buffer (25 mM Tris-HCl, 150 mM NaCl, 1% (w/v) BSA, and 0.05% (v/v) Tween-20, pH 7.6) at 4° C., then washed with Blocking Buffer three times. A 1:10,000 dilution of Streptavidin-Alkaline Phosphatase (V559C, Promega) and 1:10,000 dilution of Anti-6×His Tag® antibody [HIS-1](Alkaline Phosphatase-conjugated) (ab49746, Abcam) in 4 mL Blocking Buffer was added to the beads and incubated with gentle shaking at room temperature for 1 h. The beads were subsequently washed with 3×3 mL TBS (25 mM Tris-HCl, 150 mM NaCl, pH 7.6) (1 min ea), 3×3 mL 0.1 M glycine pH 2.8 wash buffer, 3×3 mL TBS, then 3×3 mL Alkaline Phosphatase buffer (100 mM Tris-HCl, 150 mM NaCl, 1 mM $MgCl_2$, pH 9) (5 min ea). Binding was visualized by incubating the beads in the presence of 5-bromo-4-chloro-3-indolyl phosphate/nitro blue tetrazolium (BCIP/NBT) substrate (S3771, Promega) for 25 min. Purple beads indicated background binders and were removed by pipet and discarded. The remaining clear beads were collected and stripped with 7.5 M guanidine hydrochloride pH 2.0 for 30 min, washed ten times with water, and incubated in 1-methyl-2-pyrrolidinone (NMP) overnight to decolorize.

Product Screen with IDO1 Epitope1.

Beads remaining from the pre-clear were washed with water ten times and TBS three times. Beads were then incubated with 3 mL of 100 µM IDO1 Epitope1 fragment (Biotin-PEG3-GFWEDPKE[Az4]AGGSAGQSSVFQ (SEQ ID NO: 4)) in TBS for 3 h at room temperature to allow for an in situ click reaction to occur. The beads were washed with TBS ten times and then incubated with 7.5 M guanidine hydrochloride pH 2.0 for 1 h to remove all IDO1 epitope not attached covalently to the beads. These beads were washed with TBS ten times and re-blocked with Blocking Buffer for 2 h. A 1:10,000 dilution of Streptavidin-Alkaline Phosphatase in 5 mL Blocking Buffer was added for 1 h to detect the presence of IDO1 epitope clicked to beads. The beads were subsequently washed with 3×3 mL TBS (1 min ea), 3×3 mL 0.1 M glycine pH 2.8 wash buffer, 3×3 mL TBS, then 3×3 mL Alkaline Phosphatase (pH 9) buffer (5 min ea). After this, the beads were developed with BCIP/NBT for 25 min as outlined in the pre-clear. Purple epitope-conjugated hit beads were selected by pipet. These hits and separately the non-hits were treated with 7.5 M guanidine hydrochloride pH 2.0 for 30 min to remove attached streptavidin, washed ten times with water, and incubated in NMP overnight to decolorize.

Product Screen with IDO1 Epitope2.

The hits and separately the non-hit beads obtained from the previous product screen were washed with water ten times and TBS three times. The non-hit beads were then incubated with 3 mL of 100 µM IDO1 Epitope2 fragment (Biotin-PEG3-LPPILVYADCV[Az4]ANWKKKDPNK (SEQ ID NO: 5)) in TBS for 3 h at room temperature to allow for an in situ click reaction to occur. The beads were washed with TBS ten times and then incubated with 7.5 M guanidine hydrochloride pH 2.0 for 1 h to remove all IDO1 epitope not attached covalently to the beads. These beads were washed with TBS ten times and re-blocked with Blocking Buffer for 2 h. A 1:10,000 dilution of Streptavidin-Alkaline Phosphatase in 5 mL Blocking Buffer was added for 1 h to detect the presence of IDO1 epitope clicked to beads. The beads were subsequently washed with 3×3 mL TBS (1 min ea), 3×3 mL 0.1 M glycine pH 2.8 wash buffer, 3×3 mL TBS, then 3×3 mL Alkaline Phosphatase (pH 9) buffer (5 min ea). After this, the beads were developed with BCIP/NBT for 25 min as outlined in the pre-clear. Purple epitope-conjugated hit beads were selected by pipet. These hits were treated with 7.5 M guanidine hydrochloride pH 2.0 for 30 min to remove attached streptavidin, washed ten times with water, and incubated in NMP overnight to decolorize.

Product Screen with IDO1 Epitope3.

The hits and separately the non-hit beads obtained from the previous product screen were washed with water ten times and TBS three times. The non-hit beads were then incubated with 3 mL of 100 μM IDO1 Epitope3 fragment (Biotin-PEG3-NKPLTYENM[Az4]VLFSFR (SEQ ID NO: 6)) in TBS for 3 h at room temperature to allow for an in situ click reaction to occur. The beads were washed with TBS ten times and then incubated with 7.5 M guanidine hydrochloride pH 2.0 for 1 h to remove all IDO1 epitope not attached covalently to the beads. These beads were washed with TBS ten times and re-blocked with Blocking Buffer for 2 h. A 1:10,000 dilution of Streptavidin-Alkaline Phosphatase in 5 mL Blocking Buffer was added for 1 h to detect the presence of IDO1 epitope clicked to beads. The beads were subsequently washed with 3×3 mL TBS (1 min ea), 3×3 mL 0.1 M glycine pH 2.8 wash buffer, 3×3 mL TBS, then 3×3 mL Alkaline Phosphatase (pH 9) buffer (5 min ea). After this, the beads were developed with BCIP/NBT for 25 min as outlined in the pre-clear. Purple epitope-conjugated hit beads were selected by pipet. These hits were treated with 7.5 M guanidine hydrochloride pH 2.0 for 30 min to remove attached streptavidin, washed ten times with water, and incubated in NMP overnight to decolorize.

Target Screen with His-Tagged IDO1 Protein.

The hits obtained from the third product screen were washed with water ten times and TBS three times. Next, the hits isolated for IDO1 Epitope1, Epitope2, and Epitope3 were transferred to three Corning® 8162 Costar® Spin-X® centrifuge tube filters (cellulose acetate membrane) and incubated with Blocking Buffer for 3 h at room temperature. The beads were rinsed three times with Blocking Buffer and then incubated with 150 nM of His-tagged IDO1 human recombinant protein (71182, BPS Biosciences) in Blocking Buffer (preparation: 5.8 μL His-tagged IDO1 human recombinant protein in 642 μL Blocking Buffer) for 1 h at room temperature. The beads were washed three times with Blocking Buffer and then incubated with 500 μL of 1:10,000 Anti-6×His Tag® antibody [HIS-1] (Alkaline Phosphatase-conjugated) (ab49746, Abcam) in Blocking Buffer for 1 h at room temperature. The beads were subsequently washed with 3×500 μL Blocking Buffer, 3×500 μL TBS, then 3×500 μL Alkaline Phosphatase (pH 9) buffer (centrifuging at 7000 rpm for 30 sec after each wash). After this, the beads were developed with BCIP/NBT for 10 min. Purple hit beads bound to IDO1 protein were selected by pipet and saved. The target hits for IDO1 Epitope1, Epitope2, and Epitope3 were treated with 7.5 M guanidine hydrochloride pH 2.0 for 30 min to remove bound proteins, washed ten times with water, and incubated in NMP overnight to decolorize. The hits were finally washed with water ten times to prepare for sequencing analysis.

Example 3: Sequencing Cyclic Peptide Hits by MALDI-TOF/TOF

Manual Edman Degradation.

The process is shown with chemical structures in FIG. 2. Edman steps were adapted from Klemm *Methods Mol. Biol.* 1984. Cycle 1 (to remove the Pra click handle): Cyclic peptide hits were transferred in 5-10 μL water into a 10×75 mm Pyrex tube. The coupling reaction was initiated by adding 50 μL phenylisothiocyanate (2.5% (v/v) in 50% aq. pyridine) to the beads. The tube was flushed with $N_2$ (g) for 10 s, sealed with a rubber stopper, and allowed to react for 20 min at 50° C. The solution was washed once with 300 μL heptane:ethyl acetate (10:1). The tube was centrifuged at 500 rpm for 30 s, and the organic layer was removed by pipet (being careful to not disturb the beads at the bottom of the tube). The solution was then washed once with 300 μL heptane:ethyl acetate (1:2). The tube was centrifuged at 500 rpm for 30 s, and again the organic layer was removed by pipet. The remaining solution in the tube was dried under centrifugal vacuum at 60° C. for 10 min. The cleavage reaction was initiated by adding 50 μL trifluoroacetic acid (TFA) to the beads. The tube was flushed with $N_2$ (g) for 10 s, lightly covered with a rubber stopper, and allowed to react for 10 min at 45° C. The TFA was then removed by centrifugal vacuum for 10 min. The tube was then placed in an ice bath. Pyridine (50 μL) was added, and the solution was washed three times with 250 μL ice-cold n-butyl acetate saturated with water. The remaining solution (containing the beads) was then dried under centrifugal vacuum at 60° C. for 15 min. Cycle 2 (ring opening): Beads were taken up in 10 μL water and allowed to re-equilibrate. The coupling and cleavage reactions were performed again (following the same protocol as Cycle 1). The resulting beads containing the linear anilinothiazolinone (ATZ)-peptide were taken up in 200 μL water and allowed to re-equilibrate overnight at room temperature. On the next day, beads were transferred to a Corning® 8170 Costar® Spin-X® centrifuge tube filter (nylon membrane) and washed with 10×500 μL water by centrifuge (30 s, 7000 rpm).

Cleavage of Hit Peptides from Single Beads with Cyanogen Bromide (CNBr).

Following the manual Edman degradation, each hit bead was transferred to a microcentrifuge tube containing pure water (10 μL). After addition of CNBr (10 μL, 0.50 M in 0.2 N HCl solution) the reaction vessel was purged with argon and then placed under microwave for 1 min (Lee et al. *J. Comb. Chem.* 2008). Acidic aq. CNBr results in methionine-specific cleavage at the C-terminus of the linear ATZ-peptide, resulting in cleavage of the peptide from the bead. The resulting solution was concentrated under centrifugal vacuum for 2 hours at 45° C.

Sequencing of Linear aTZ-Peptides Cleaved from Single Beads by MALDI-MS and MS/MS.

To each tube was added α-cyano-4-hydroxycinnamic acid (CHCA) (0.5 μL, 5 mg/mL matrix solution in acetonitrile/water (70:30) containing 0.1% TFA (v/v)). The mixture was taken up to be spotted onto a 384-well MALDI plate, which was allowed to stand for 15 min to dry naturally. Samples were then analyzed by matrix-assisted laser-desorption/ionization (MALDI) time-of-flight (TOF) mass spectrometry (MS) using a Bruker ultrafleXtreme™ TOF/TOF instrument (Bruker Daltonics; Bremen, Germany) operated in reflectron mode. MS/MS spectra were acquired for each sample in LIFT™ mode. BioTools™ was used to assign the sequence based on analysis of the MS/MS spectra.

Candidate peptides were re-synthesized on a cleavable resin. The linear peptide was first synthesized on Rink amide resin using conventional Fmoc-based solid phase peptide synthesis (SPPS). The peptide was cyclized between the N-terminal Pra and C-terminal Az4 using copper(I) iodide (1.5 equiv) and ascorbic acid (5 equiv) in 4:1 NMP:piperidine. On the next day, the residual copper bound to the resin was removed by shaking the resin with NMP containing 5% (w/v) sodium diethyldithiocarbamate trihydrate and 5% (v/v) N,N-diisopropylethylamine for 5 min. These monocyclic peptides were then cleaved from the resin for 2 h with 92.5% TFA, 2.5% H$_2$O, 2.5% TIS (triisopropylsilane), and 2.5% DODT (3,6-dioxa-1,8-octanedithiol), and then purified by reversed phase HPLC using a C$_{18}$ column (Phenomenex Luna, 5 µm, 250×10 mm).

Example 4: In Vitro Assays with IDO1 Epitope Targeted Ligands

IDO1 ELISA (Affinity Assay). Protocol:

A black 96-well NeutrAvidin Coated High Binding Capacity plate (15510, Pierce) was coated with 2 µM biotinylated macrocyclic peptide ligand in TBS (25 mM Tris-HCl, 150 mM NaCl, pH 7.6) for 2 h at room temperature. The plate was aspirated and then washed with Wash Buffer (0.05% (v/v) Tween-20 in PBS, 6×). His-tagged IDO1 human recombinant protein (71182, BPS Biosciences) was serially diluted in Wash Buffer (from 200 to 0 nM) and incubated in the designated microwells for 1 h at room temperature. Microwells were aspirated and subsequently washed with Wash Buffer (11×). To detect the bound IDO1 protein, Alkaline Phosphatase (AP)-conjugated Anti-6×His Tag® antibody [HIS-1] (ab49746, Abcam) was prepared at 1:10,000 dilution and added to the microwells for 1 h at room temperature. The plate was aspirated and washed with Wash Buffer (5×). AttoPhos® AP Fluorescent Substrate System (S1000, Promega) was employed to develop the microwells. Using an excitation wavelength of 430 nm, fluorescent emission at 535 nm was recorded by Beckman Coulter DTX880 photometer. Titration curves were fit using a four-parameter regression curve fitting program to determine EC$_{50}$ values.

Results and Discussion:

The binding affinities of biotin-PEG$_3$-modified macrocyclic peptide ligands were tested in an ELISA format. For these assays, a dilution series of His-tagged IDO1 human recombinant protein was captured using the macrocyclic peptide ligands immobilized on a NeutrAvidin-coated plate. The nine macrocyclic peptide ligands displayed EC$_{50}$ values ranging from 20 to 125 nM for human IDO1 protein. The sequences of the peptide ligands are listed in Table 1, where D-amino acids are denoted in lowercase, Me-Trp=1-methyl-L-tryptophan, and F-Phe=4-fluoro-L-phenylalanine. Chemical structures and in vitro binding data are shown in FIGS. 3 to 11.

TABLE 1

Sequences of macrocyclic peptide hits identified against IDO1

| | Epitope Targeted | x2 | x3 | x4 | x5 | x6 |
|---|---|---|---|---|---|---|
| hit1 | 1 | f | r | f | Me-Trp | s |
| hit2 | 1 | n | s | f | r | Me-Trp |
| hit3 | 2 | r | y | s | Me-Trp | r |
| hit4 | 2 | n | l | f | Me-Trp | F-Phe |
| hit5 | 2 | n | l | w | Me-Trp | r |
| hit6 | 2 | s | p | w | w | F-Phe |
| hit7 | 3 | r | f | f | y | l |
| hit8 | 3 | n | s | h | F-Phe | r |
| hit9 | 1 | w | y | r | a | y |

Example 5: Species Cross-Reactivity Analysis

To test for cross-reactivity with murine IDO1, the human IDO1 targeted macrocyclic peptide ligands were assayed against the murine IDO1 protein by ELISA. FIG. 12 shows curves from the ELISA titrations of human and murine IDO1 proteins against the immobilized macrocycles. As expected, the macrocyclic peptide ligands showed binding to both proteins because they were developed against IDO1 epitopes that show high homology between human and mouse. EC$_{50}$ values ranging from 18 to 158 nM for human IDO1 protein, and 17 to 130 nM for mouse IDO1 protein were obtained.

Example 6: Enzyme Assay for IDO1

Figure 13A:
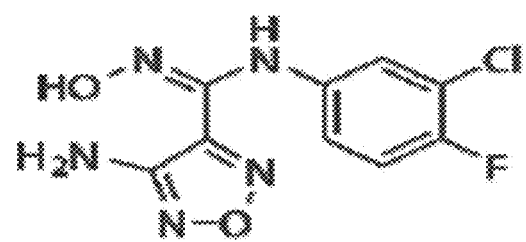
FIGS. 13A and 13B: IDO1 enzyme assay.
Figure 13B:
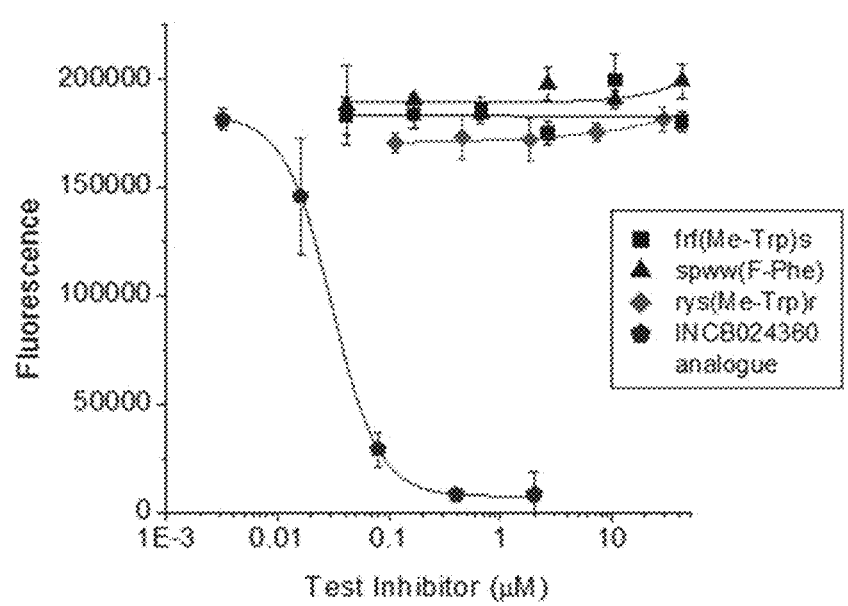

Since the macrocyclic peptide ligands are designed against epitopes near the active site, we sought to determine whether they can modulate the activity of IDO1. The IDO1 Fluorogenic Inhibitor Screening Assay Kit (72037, BPS Biosciences) was used to measure the enzyme inhibition of human IDO1 in the presence of macrocyclic peptide ligands. IDO1 catalyzes the conversion of the essential amino acid L-tryptophan (L-Trp) to N-formylkynurenine (NFK). In the assay, the test inhibitor and enzyme were added to a sample containing L-Trp substrate. After incubation for 1 h at room temperature, 20 µL Fluorescence Solution was added and incubated at 37° C. for 4 h to produce a fluorescent product. Activity was measured by reading sample fluorescence at λ=510 nm following excitation of the reaction product at λ=400 nm. INCB024360 analogue was tested as a control IDO1 inhibitor (FIG. 13A). INCB024360 analogue displayed an IC$_{50}$ value of 31 nM, in agreement with the published value (Röhrig et al. *J. Med. Chem.* 2015). Inhibitory potency of the macrocyclic peptide ligands was not observed (IC$_{50}$>40 µM) (FIG. 13B).

Example 7: Assay to Determine Orientation of Macrocycle Binding to Synthetic IDO1 Epitopes Protocol:

A black 96-well NeutrAvidin Coated High Binding Capacity plate (15510, Pierce) was coated with 2 µM macrocyclic peptide ligand in TBS (pH 7.6) for 1 h at room temperature. The plate was aspirated and then washed with Wash Buffer (0.05% (v/v) Tween-20 in PBS, 6×). Chemically synthesized 6×His-tagged IDO1 epitopes ("6×His" disclosed as SEQ ID NO: 7) were prepared at 2 µM in Wash Buffer and incubated in the designated microwells for 1 h at room temperature. Wash Buffer without epitope was added as a control. Microwells were aspirated and subsequently washed with Wash Buffer (11×). To detect the bound IDO1 epitopes, AP-conjugated Anti-6×His Tag® antibody [HIS-1] (ab49746, Abcam) was prepared at 1:10,000 dilution and added to the microwells for 1 h at room temperature. The plate was aspirated and washed with Wash Buffer (5×). AttoPhos® AP Fluorescent Substrate System (S1000, Promega) was employed to develop the microwells. Using an excitation wavelength of 430 nm, fluorescent emission at 535 nm was recorded by Beckman Coulter DTX880 photometer. Data are shown after subtraction of the no-epitope background.

Results and Discussion:

For this experiment, variants of IDO1 Epitope1 were synthesized with a 6×His assay handle ("6×His" disclosed as SEQ ID NO: 7) and strategic scrambling of the sequences either N-terminal or C-terminal to the location of the click handle (F259) (FIG. 14A). Variants of IDO1 Epitope2 were similarly synthesized with a 6×His assay handle ("6×His" disclosed as SEQ ID NO: 7) and strategic sequence scrambling (either N-terminal or C-terminal to L131) (FIG. 14B). Point ELISAs for these 6×His-tagged IDO1 epitopes ("6× His" disclosed as SEQ ID NO: 7) were conducted against the immobilized macrocyclic peptide ligands. For biotin-PEG$_3$-modified frf(Me-Trp)s, maximum ELISA signals were obtained for binding to IDO1 Epitope1N (FIG. 14C) indicating preferential binding to the N-terminal portion of IDO1 Epitope1. For biotin-PEG$_3$-modified nlw(Me-Trp)r and spww(F-Phe), maximum ELISA signals were obtained for binding to IDO1 Epitope2N (FIGS. 14D and 14E) indicating preferential binding to the N-terminal portion of IDO1 Epitope2. These results confirm the selective nature of the epitope-targeting strategy.

Example 8: Alanine Scan and Tighter Rings (3- and 4-Mers)

The effect of amino acid substitutions of the macrocycles on IDO1 binding was also studied. Each amino acid was systematically replaced with a D-alanine (Tables 2-5).

TABLE 2

Synthesis Data for spww(F-Phe) Alanine Scan Variants

1

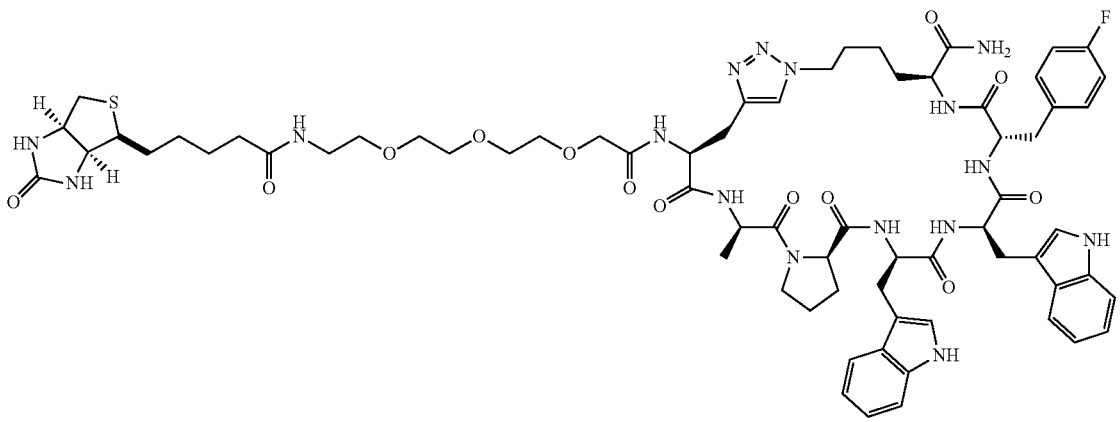 [SMILES: C[C@H]1NC(=O)[C@@H](NC(=O)COCCOCCOCCNC(=O)CCCC[C@@H]2SC[C@@H]3NC(=O)N[C@@H]32)Cc2cn(nn2)CCCC[C@@H](C(N)=O)NC(=O)[C@H](Cc2ccc(F)cc2)NC(=O)[C@@H](Cc2c[nH]c3ccccc23)NC(=O)[C@@H](Cc2c[nH]c3ccccc23)NC(=O)[C@H]2CCCN2C1=O]

Biotin-PEG$_3$-Cy(apww(F-Phe)). MALDI-MS (m/z): calcd. for $C_{68}H_{87}FN_{16}O_{13}S$ (M + H) 1387.63; found 1388.07.

2

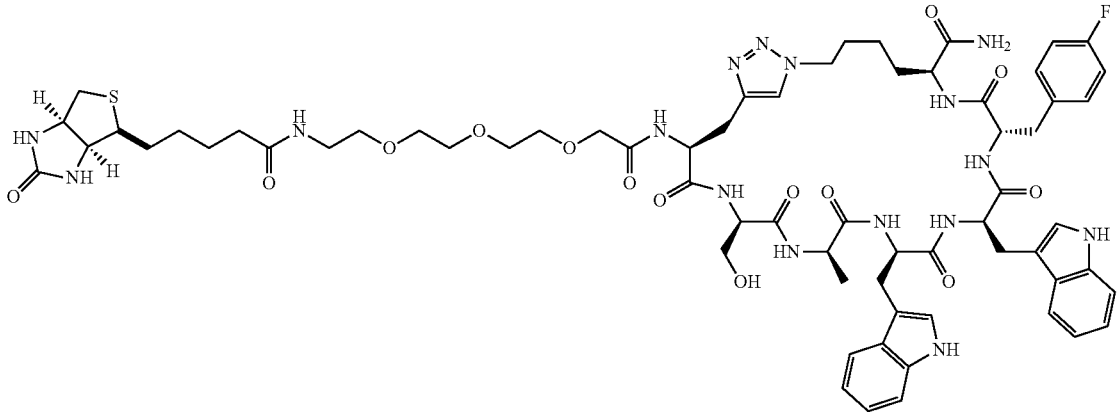 [SMILES: C[C@H]1NC(=O)[C@@H](CO)NC(=O)[C@@H](NC(=O)COCCOCCOCCNC(=O)CCCC[C@@H]2SC[C@@H]3NC(=O)N[C@@H]32)Cc2cn(nn2)CCCC[C@@H](C(N)=O)NC(=O)[C@H](Cc2ccc(F)cc2)NC(=O)[C@@H](Cc2c[nH]c3ccccc23)NC(=O)[C@@H](Cc2c[nH]c3ccccc23)NC1=O]

Biotin-PEG3-Cy(saww(F-Phe)). MALDI-MS (m/z): calcd. for $C_{66}H_{85}FN_{16}O_{14}S$ (M + H) 1377.61; found 1377.79.

TABLE 2-continued
Synthesis Data for spww(F-Phe) Alanine Scan Variants
3
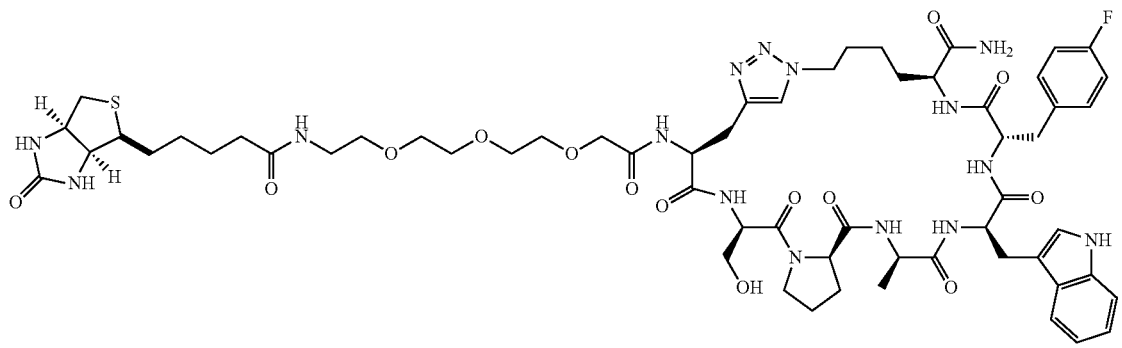 [SMILES: C[C@H]1NC(=O)[C@H]2CCCN2C(=O)[C@@H](CO)NC(=O)[C@@H](NC(=O)COCCOCCOCCNC(=O)CCCC[C@@H]2SC[C@@H]3NC(=O)N[C@@H]32)Cc2cn(nn2)CCCC[C@@H](C(N)=O)NC(=O)[C@H](Cc2ccc(F)cc2)NC(=O)[C@@H](Cc2c[nH]c3ccccc23)NC1=O]
Biotin-PEG$_3$-Cy(spaw(F-Phe)). MALDI-MS (m/z): calcd. for C$_{60}$H$_{82}$FN$_{15}$O$_{14}$S (M + H) 1288.59; found 1288.82.
4
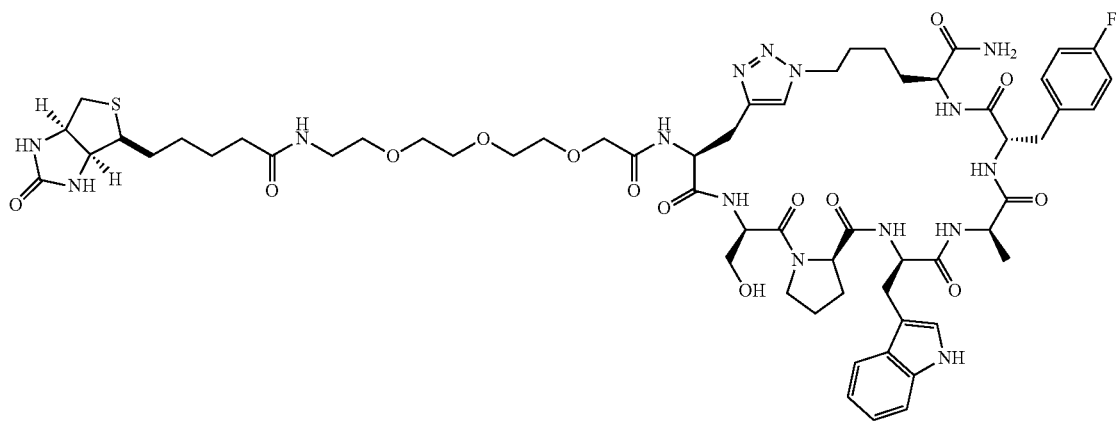 [SMILES: C[C@H]1NC(=O)[C@@H](Cc2c[nH]c3ccccc23)NC(=O)[C@H]2CCCN2C(=O)[C@@H](CO)NC(=O)[C@@H](NC(=O)COCCOCCOCCNC(=O)CCCC[C@@H]2SC[C@@H]3NC(=O)N[C@@H]32)Cc2cn(nn2)CCCC[C@@H](C(N)=O)NC(=O)[C@H](Cc2ccc(F)cc2)NC1=O]
Biotin-PEG$_3$-Cy(spwa(F-Phe)). MALDI-MS (m/z): calcd. for C$_{60}$H$_{82}$FN$_{15}$O$_{14}$S (M + H) 1288.59; found 1288.90.
5
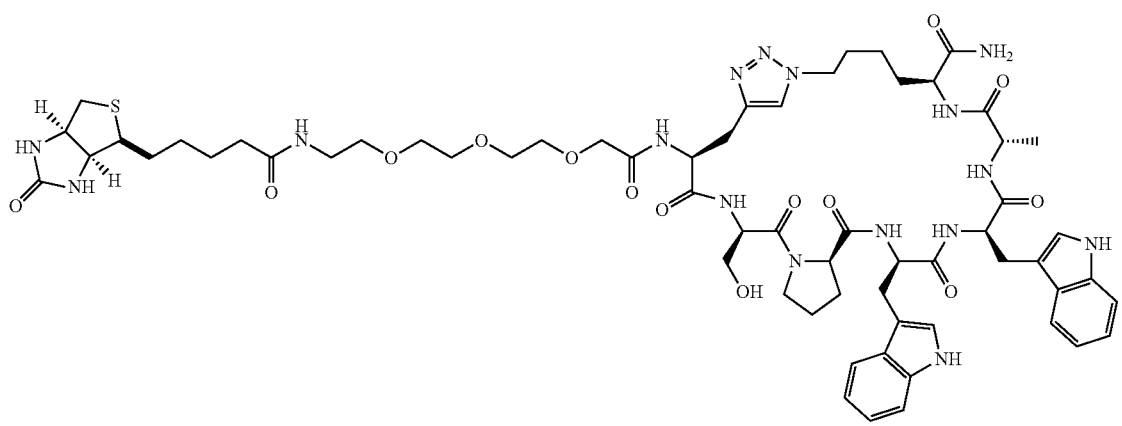 [SMILES: C[C@@H]1NC(=O)[C@@H](Cc2c[nH]c3ccccc23)NC(=O)[C@@H](Cc2c[nH]c3ccccc23)NC(=O)[C@H]2CCCN2C(=O)[C@@H](CO)NC(=O)[C@@H](NC(=O)COCCOCCOCCNC(=O)CCCC[C@@H]2SC[C@@H]3NC(=O)N[C@@H]32)Cc2cn(nn2)CCCC[C@@H](C(N)=O)NC1=O]
Biotin-PEG$_3$-Cy(spwwa). MALDI-MS (m/z): calcd. for C$_{62}$H$_{84}$N$_{16}$O$_{14}$S (M + H) 1309.61; found 1309.92.

TABLE 3
Synthesis Data for nlf(Me-Trp)(F-Phe) Alanine Scan Variants
1
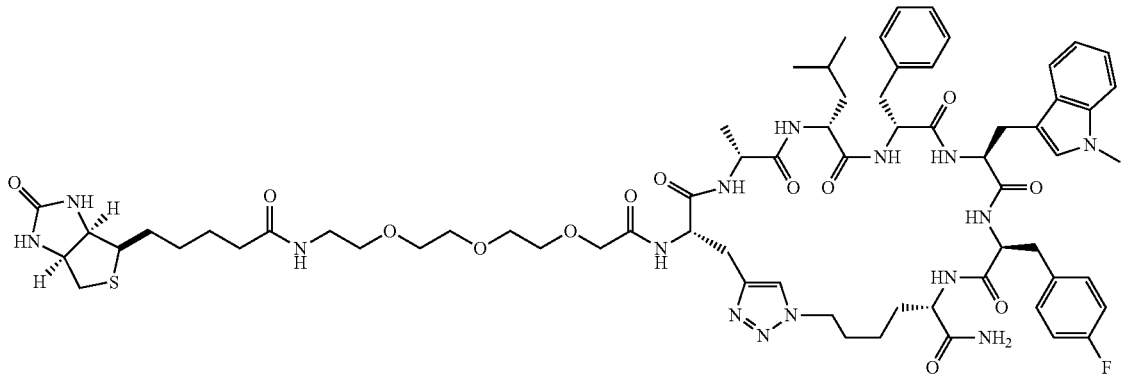 [SMILES: CC(C)C[C@H]1NC(=O)[C@@H](C)NC(=O)[C@@H](NC(=O)COCCOCCOCCNC(=O)CCCC[C@H]2SC[C@H]3NC(=O)N[C@H]32)Cc2cn(nn2)CCCC[C@@H](C(N)=O)NC(=O)[C@H](Cc2ccc(F)cc2)NC(=O)[C@H](Cc2cn(C)c3ccccc23)NC(=O)[C@@H](Cc2ccccc2)NC1=O]
Biotin-PEG$_3$-Cy(alf(Me-Trp)(F-Phe)). MALDI-MS (m/z): calcd. for C$_{68}$H$_{92}$FN$_{15}$O$_{13}$S
(M + H) 1378.67; found 1378.58.
2
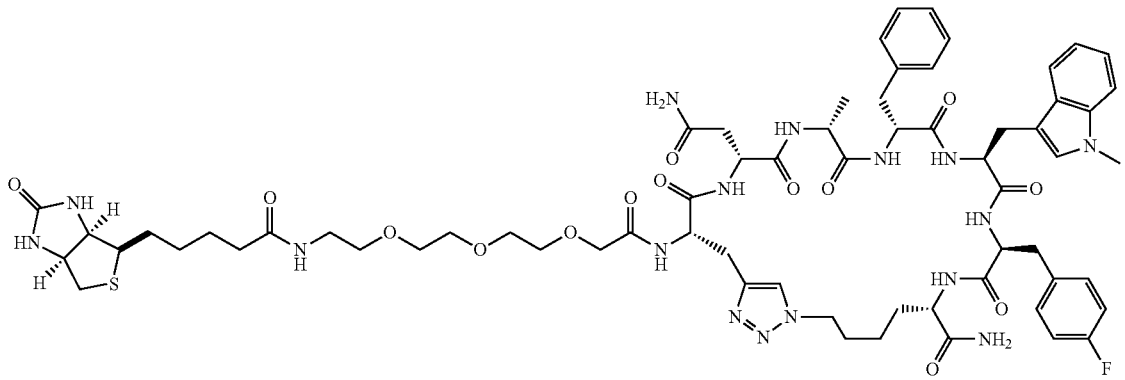 [SMILES: C[C@H]1NC(=O)[C@@H](CC(N)=O)NC(=O)[C@@H](NC(=O)COCCOCCOCCNC(=O)CCCC[C@H]2SC[C@H]3NC(=O)N[C@H]32)Cc2cn(nn2)CCCC[C@@H](C(N)=O)NC(=O)[C@H](Cc2ccc(F)cc2)NC(=O)[C@H](Cc2cn(C)c3ccccc23)NC(=O)[C@@H](Cc2ccccc2)NC1=O]
Biotin-PEG$_3$-Cy(naf(Me-Trp)(F-Phe)). MALDI-MS (m/z): calcd. for C$_{66}$H$_{87}$FN$_{16}$O$_{14}$S
(M + H) 1379.63; found 1379.83.
3
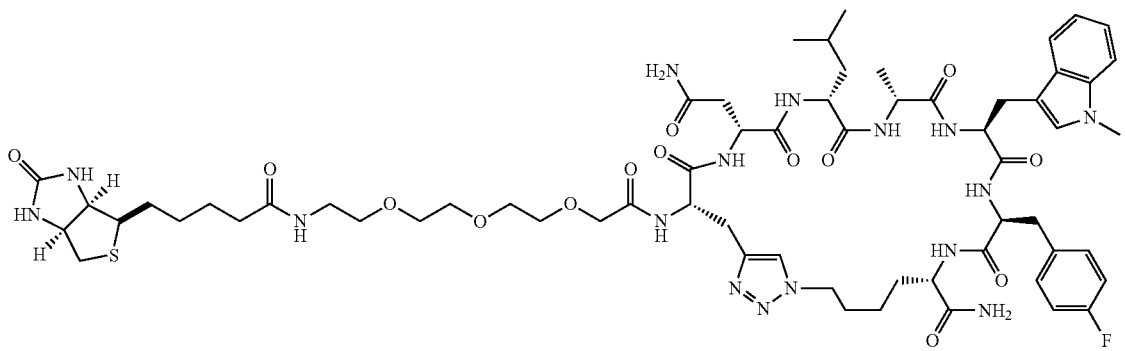 [SMILES: CC(C)C[C@H]1NC(=O)[C@@H](CC(N)=O)NC(=O)[C@@H](NC(=O)COCCOCCOCCNC(=O)CCCC[C@H]2SC[C@H]3NC(=O)N[C@H]32)Cc2cn(nn2)CCCC[C@@H](C(N)=O)NC(=O)[C@H](Cc2ccc(F)cc2)NC(=O)[C@H](Cc2cn(C)c3ccccc23)NC(=O)[C@@H](C)NC1=O]
Biotin-PEG$_3$-Cy(nla(Me-Trp)(F-Phe)). MALDI-MS (m/z): calcd. for C$_{63}$H$_{89}$FN$_{16}$O$_{14}$S
(M + H) 1345.64; found 1345.64.

TABLE 3-continued
Synthesis Data for nlf(Me-Trp)(F-Phe) Alanine Scan Variants
4
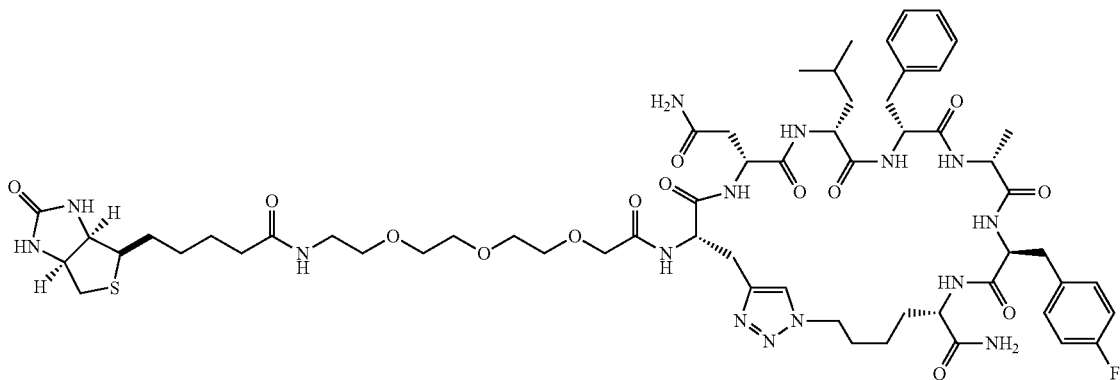 [SMILES: CC(C)C[C@H]1NC(=O)[C@@H](CC(N)=O)NC(=O)[C@@H](NC(=O)COCCOCCOCCNC(=O)CCCC[C@H]2SC[C@H]3NC(=O)N[C@H]32)Cc2cn(nn2)CCCC[C@@H](C(N)=O)NC(=O)[C@H](Cc2ccc(F)cc2)NC(=O)[C@@H](C)NC(=O)[C@@H](Cc2ccccc2)NC1=O]
Biotin-PEG$_3$-Cy(nlfa(F-Phe)). MALDI-MS (m/z): calcd. for C$_{60}$H$_{86}$FN$_{15}$O$_{14}$S (M + H) 1292.62; found 1292.55.
5
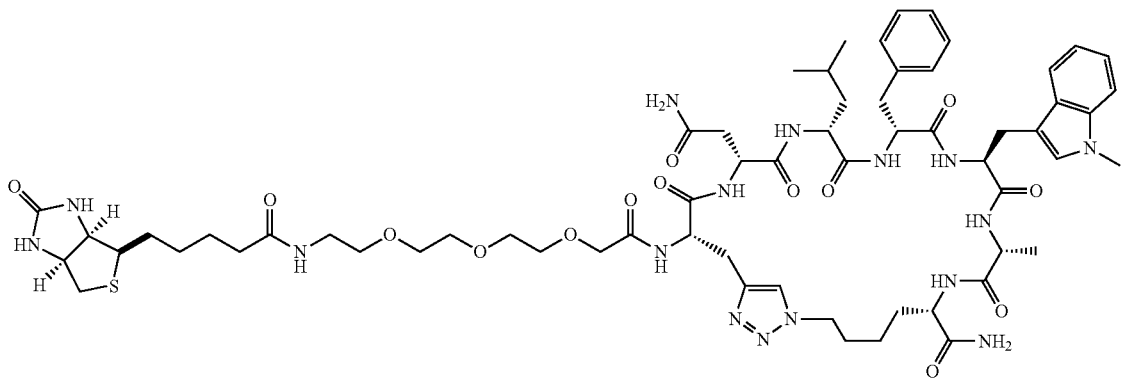 [SMILES: CC(C)C[C@H]1NC(=O)[C@@H](CC(N)=O)NC(=O)[C@@H](NC(=O)COCCOCCOCCNC(=O)CCCC[C@H]2SC[C@H]3NC(=O)N[C@H]32)Cc2cn(nn2)CCCC[C@@H](C(N)=O)NC(=O)[C@@H](C)NC(=O)[C@H](Cc2cn(C)c3ccccc23)NC(=O)[C@@H](Cc2ccccc2)NC1=O]
Biotin-PEG$_3$-Cy(nlf(Me-Trp)a). MALDI-MS (m/z): calcd. for C$_{63}$H$_{90}$N$_{16}$O$_{14}$S (M + H) 1327.65; found 1327.63.
TABLE 4
Synthesis Data for frf(Me-Trp)s Alanine Scan Variants
1
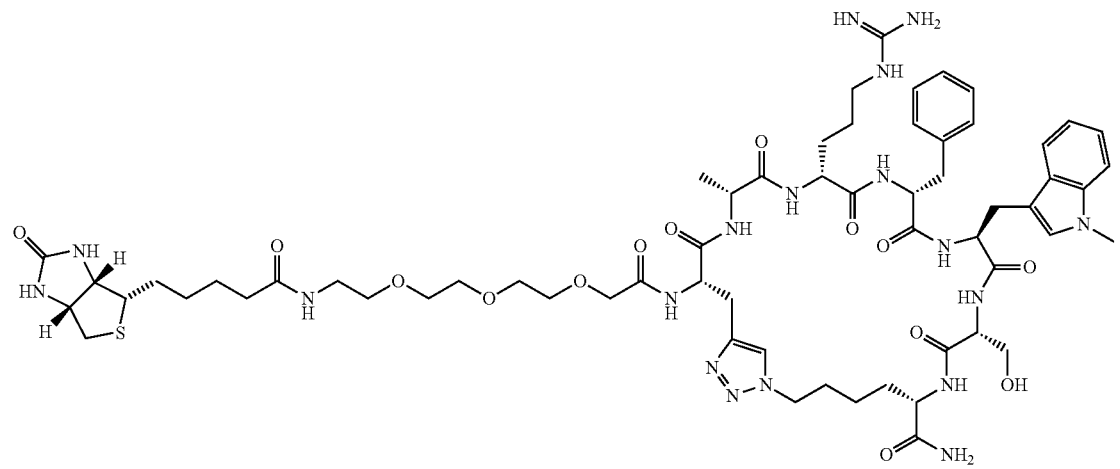 [SMILES: C[C@H]1NC(=O)[C@@H](NC(=O)COCCOCCOCCNC(=O)CCCC[C@@H]2SC[C@@H]3NC(=O)N[C@@H]32)Cc2cn(nn2)CCCC[C@@H](C(N)=O)NC(=O)[C@@H](CO)NC(=O)[C@H](Cc2cn(C)c3ccccc23)NC(=O)[C@@H](Cc2ccccc2)NC(=O)[C@@H](CCCNC(=N)N)NC1=O]
Biotin-PEG$_3$-Cy(arf(Me-Trp)s). MALDI-MS (m/z): calcd. for C$_{62}$H$_{90}$N$_{18}$O$_{14}$S (M + H) 1343.66; found 1343.64.

TABLE 4-continued
Synthesis Data for frf(Me-Trp)s Alanine Scan Variants
2
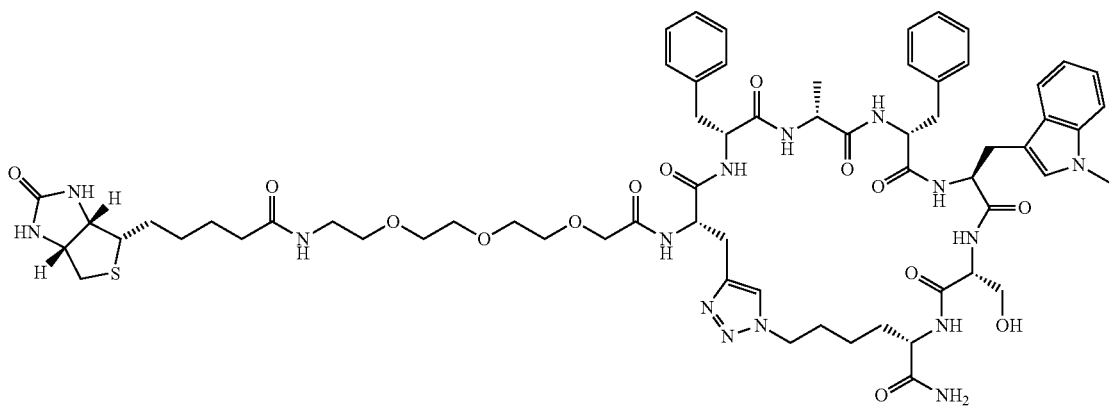 [SMILES: C[C@H]1NC(=O)[C@@H](Cc2ccccc2)NC(=O)[C@@H](NC(=O)COCCOCCOCCNC(=O)CCCC[C@@H]2SC[C@@H]3NC(=O)N[C@@H]32)Cc2cn(nn2)CCCC[C@@H](C(N)=O)NC(=O)[C@@H](CO)NC(=O)[C@H](Cc2cn(C)c3ccccc23)NC(=O)[C@@H](Cc2ccccc2)NC1=O]
Biotin-PEG$_3$-Cy(faf(Me-Trp)s). MALDI-MS (m/z): calcd. for $C_{65}H_{87}N_{15}O_{14}S$ (M + H) 1334.63; found 1334.21.
3
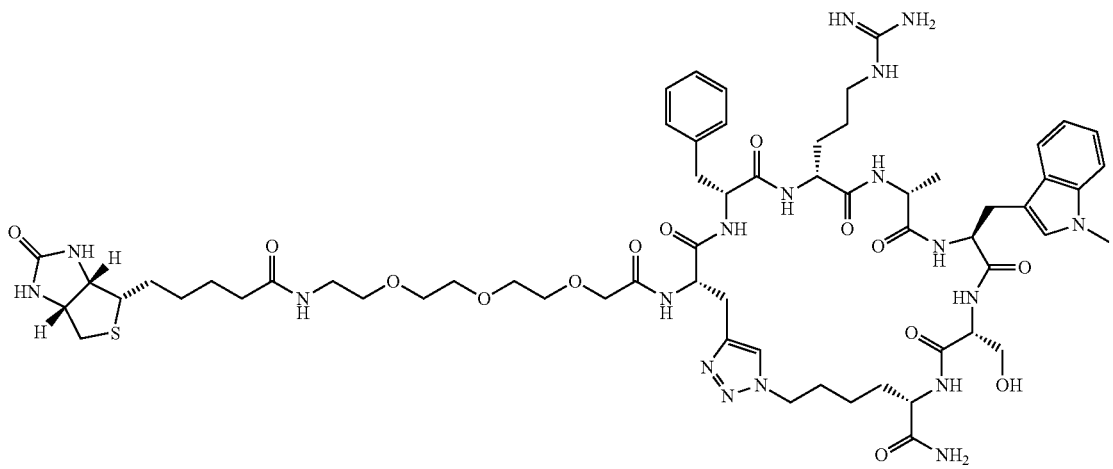 [SMILES: C[C@H]1NC(=O)[C@@H](CCCNC(=N)N)NC(=O)[C@@H](Cc2ccccc2)NC(=O)[C@@H](NC(=O)COCCOCCOCCNC(=O)CCCC[C@@H]2SC[C@@H]3NC(=O)N[C@@H]32)Cc2cn(nn2)CCCC[C@@H](C(N)=O)NC(=O)[C@@H](CO)NC(=O)[C@H](Cc2cn(C)c3ccccc23)NC1=O]
Biotin-PEG$_3$-Cy(fra(Me-Trp)s). MALDI-MS (m/z): calcd. for $C_{62}H_{90}N_{18}O_{14}S$ (M + H) 1343.66; found 1343.66.
4
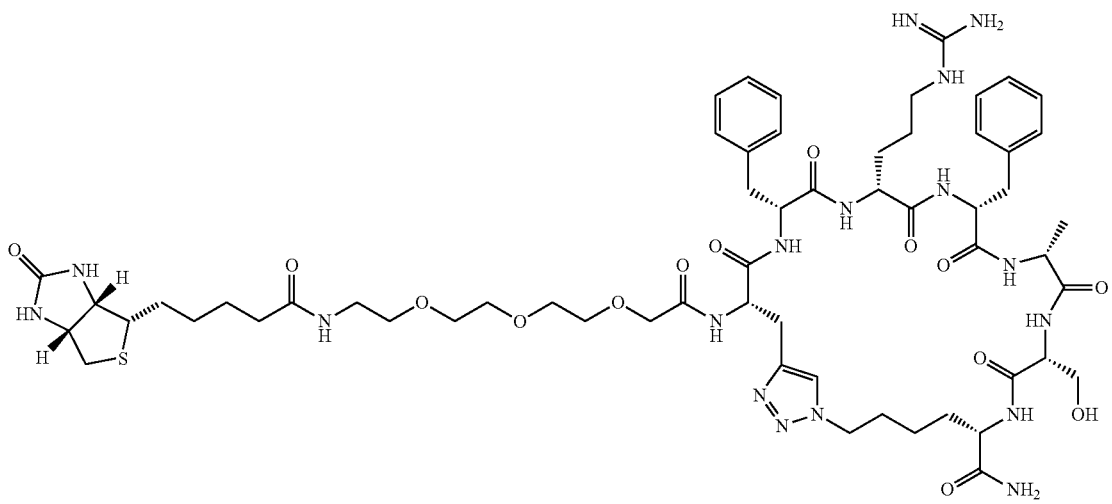 [SMILES: C[C@H]1NC(=O)[C@@H](Cc2ccccc2)NC(=O)[C@@H](CCCNC(=N)N)NC(=O)[C@@H](Cc2ccccc2)NC(=O)[C@@H](NC(=O)COCCOCCOCCNC(=O)CCCC[C@@H]2SC[C@@H]3NC(=O)N[C@@H]32)Cc2cn(nn2)CCCC[C@@H](C(N)=O)NC(=O)[C@@H](CO)NC1=O]
Biotin-PEG$_3$-Cy(frfas). MALDI-MS (m/z): calcd. for $C_{59}H_{87}N_{17}O_{14}S$ (M + H) 1290.63; found 1290.07.

TABLE 4-continued
Synthesis Data for frf(Me-Trp)s Alanine Scan Variants
5
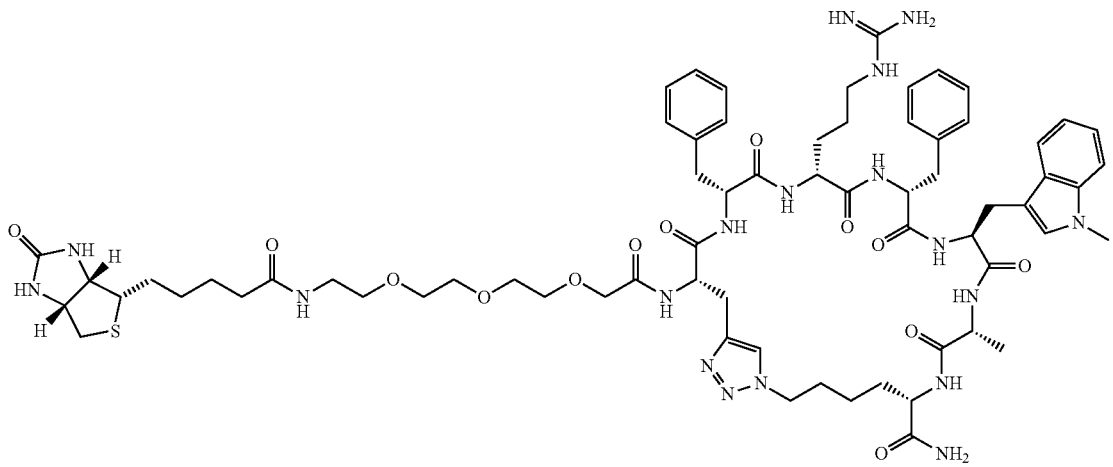 [SMILES: C[C@H]1NC(=O)[C@H](Cc2cn(C)c3ccccc23)NC(=O)[C@@H](Cc2ccccc2)NC(=O)[C@@H](CCCNC(=N)N)NC(=O)[C@@H](Cc2ccccc2)NC(=O)[C@@H](NC(=O)COCCOCCOCCNC(=O)CCCC[C@@H]2SC[C@@H]3NC(=O)N[C@@H]32)Cc2cn(nn2)CCCC[C@@H](C(N)=O)NC1=O]
Biotin-PEG$_3$-Cy(frf(Me-Trp)a). MALDI-MS (m/z): calcd. for C$_{68}$H$_{94}$N$_{18}$O$_{13}$S (M + H)
1403.70; found 1403.84.
TABLE 5
Synthesis Data for wyray Alanine Scan Variants
1
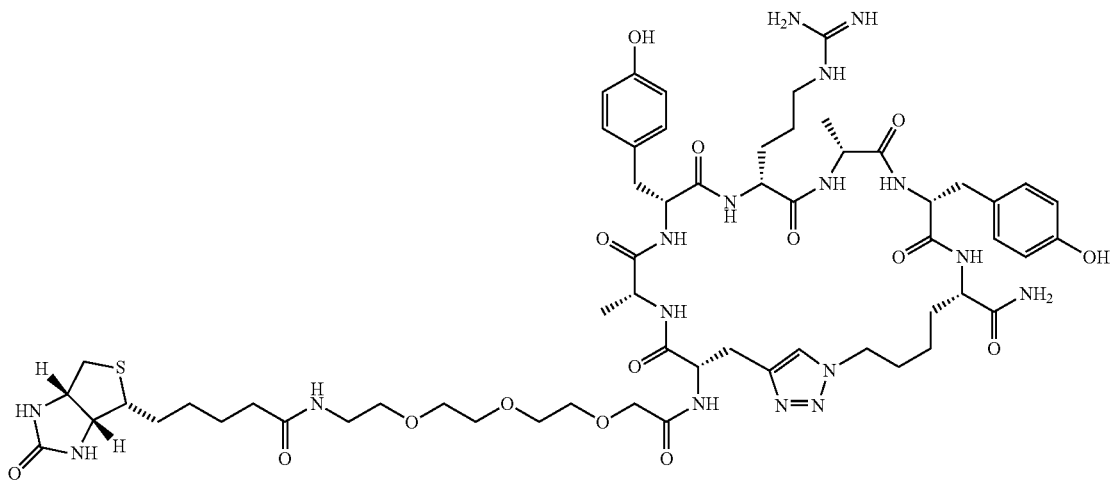 [SMILES: C[C@H]1NC(=O)[C@@H](NC(=O)COCCOCCOCCNC(=O)CCCC[C@H]2SC[C@H]3NC(=O)N[C@H]32)Cc2cn(nn2)CCCC[C@@H](C(N)=O)NC(=O)[C@@H](Cc2ccc(O)cc2)NC(=O)[C@@H](C)NC(=O)[C@@H](CCCNC(=N)N)NC(=O)[C@@H](Cc2ccc(O)cc2)NC1=O]
Biotin-PEG$_3$-Cy(ayray). MALDI-MS (m/z): calcd. for C$_{59}$H$_{87}$N$_{17}$O$_{15}$S (M + H)
1306.63; found 1307.02.

TABLE 5-continued
Synthesis Data for wyray Alanine Scan Variants
2
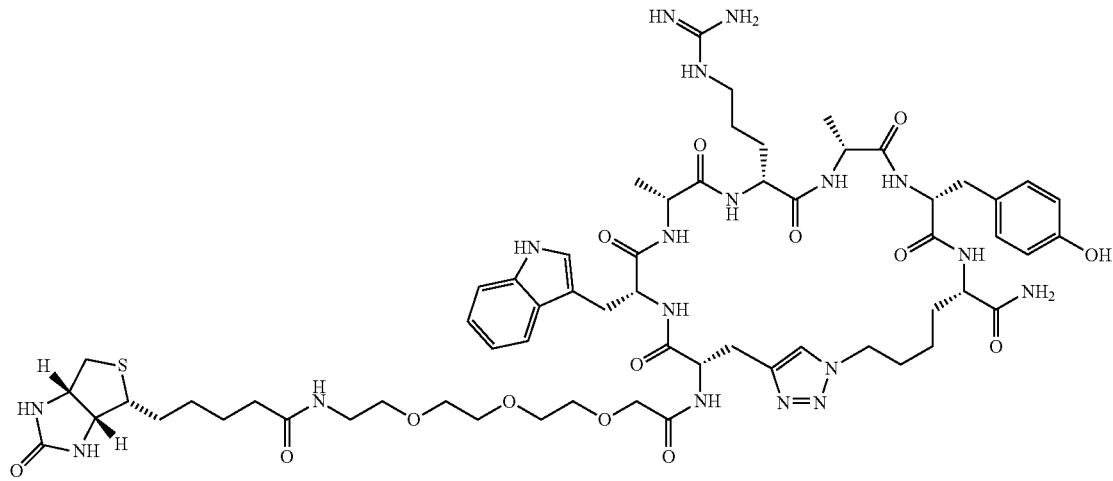 [SMILES: C[C@H]1NC(=O)[C@@H](Cc2c[nH]c3ccccc23)NC(=O)[C@@H](NC(=O)COCCOCCOCCNC(=O)CCCC[C@H]2SC[C@H]3NC(=O)N[C@H]32)Cc2cn(nn2)CCCC[C@@H](C(N)=O)NC(=O)[C@@H](Cc2ccc(O)cc2)NC(=O)[C@@H](C)NC(=O)[C@@H](CCCNC(=N)N)NC1=O]
Biotin-PEG$_3$-Cy(waray). MALDI-MS (m/z): calcd. for $C_{61}H_{88}N_{18}O_{14}S$ (M + H) 1329.64; found 1329.81.
3
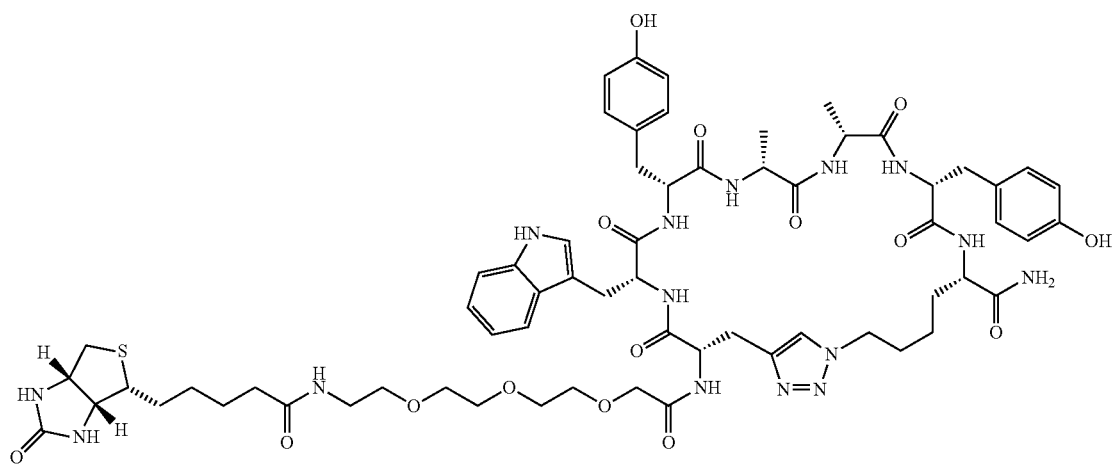 [SMILES: C[C@H]1NC(=O)[C@@H](C)NC(=O)[C@@H](Cc2ccc(O)cc2)NC(=O)[C@@H](Cc2c[nH]c3ccccc23)NC(=O)[C@@H](NC(=O)COCCOCCOCCNC(=O)CCCC[C@H]2SC[C@H]3NC(=O)N[C@H]32)Cc2cn(nn2)CCCC[C@@H](C(N)=O)NC(=O)[C@@H](Cc2ccc(O)cc2)NC1=O]
Biotin-PEG$_3$-Cy(wyaay). MALDI-MS (m/z): calcd. for $C_{64}H_{85}N_{15}O_{15}S$ (M + H) 1336.61; found 1336.76.

TABLE 5-continued

Synthesis Data for wyray Alanine Scan Variants

4
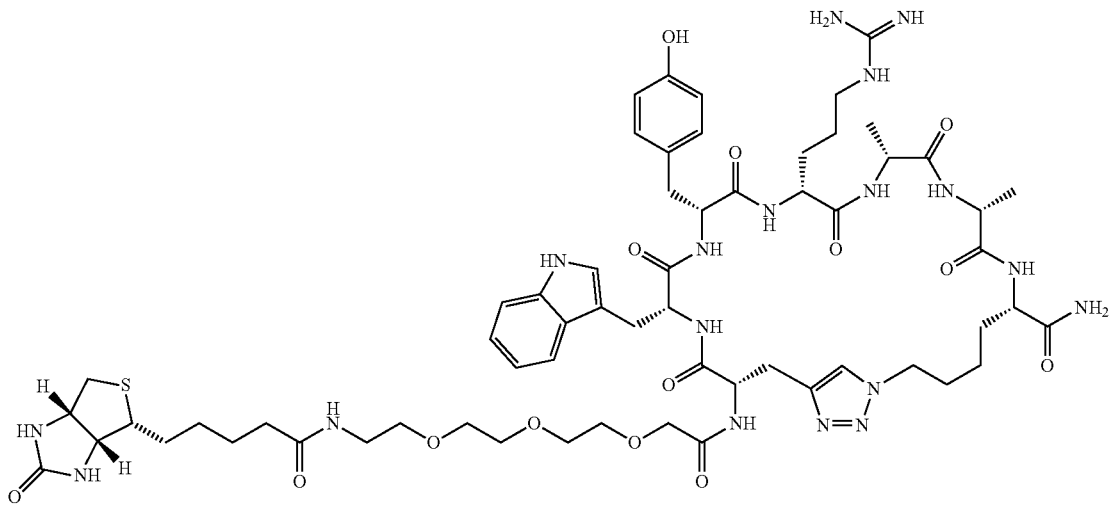 [SMILES: C[C@H]1NC(=O)[C@@H](C)NC(=O)[C@@H](CCCNC(=N)N)NC(=O)[C@@H](Cc2ccc(O)cc2)NC(=O)[C@@H](Cc2c[nH]c3ccccc23)NC(=O)[C@@H](NC(=O)COCCOCCOCCNC(=O)CCCC[C@H]2SC[C@H]3NC(=O)N[C@H]32)Cc2cn(nn2)CCCC[C@@H](C(N)=O)NC1=O]

Biotin-PEG$_3$-Cy(wyraa). MALDI-MS (m/z): calcd. for C$_{61}$H$_{88}$N$_{18}$O$_{14}$S (M + H) 1329.64; found 1330.40.

The D-alanine substituted, biotin-PEG$_3$-modified macrocycles were tested in the IDO1 ELISA (Affinity assay). For these assays, a dilution series of His-tagged IDO1 human recombinant protein was captured using macrocycles immobilized on a NeutrAvidin-coated plate.

Based on the results of the alanine scan, 3-mer and 4-mer macrocycles were synthesized and assayed for IDO1 binding using the IDO1 ELISA (Affinity assay). Synthesis data for the 3-mer and 4-mer macrocycles is shown in Tables 6-9.

TABLE 6

Synthesis Data for spww(F-Phe) 4-mer and 3-mer Variants

1
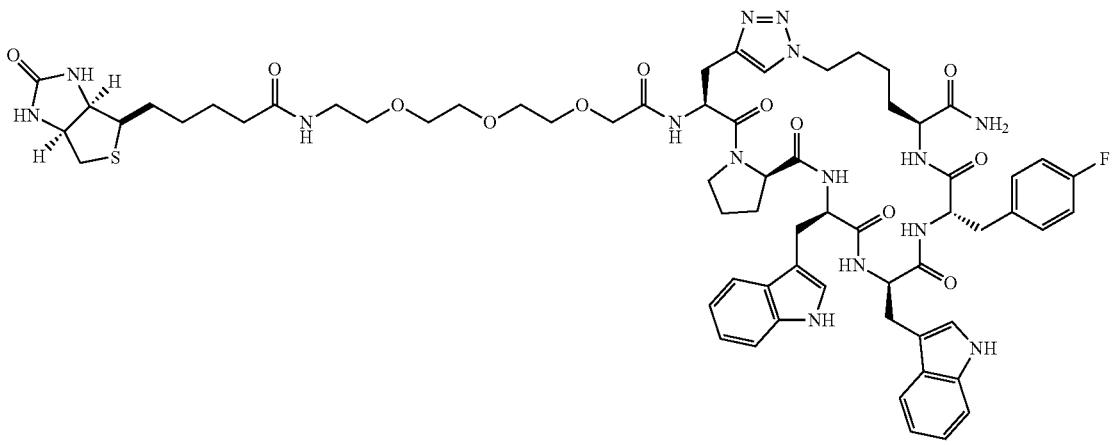 [SMILES: NC(=O)[C@@H]1CCCCn2cc(nn2)C[C@H](NC(=O)COCCOCCOCCNC(=O)CCCC[C@H]2SC[C@H]3NC(=O)N[C@H]32)C(=O)N2CCC[C@@H]2C(=O)N[C@H](Cc2c[nH]c3ccccc23)C(=O)N[C@H](Cc2c[nH]c3ccccc23)C(=O)N[C@@H](Cc2ccc(F)cc2)C(=O)N1]

Biotin-PEG$_3$-Cy(pww(F-Phe)). MALDI-MS (m/z): calcd. for C$_{65}$H$_{82}$FN$_{15}$O$_{12}$S (M + H) 1316.60; found 1316.72.

TABLE 6-continued
Synthesis Data for spww(F-Phe) 4-mer and 3-mer Variants
2
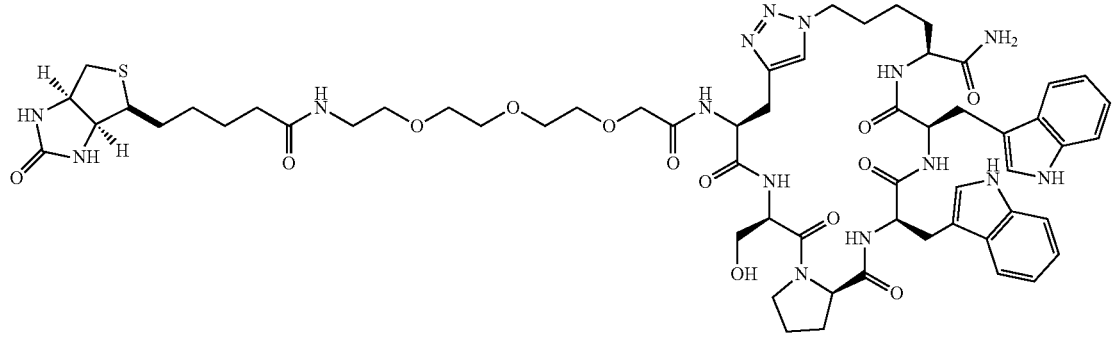 [SMILES: NC(=O)[C@@H]1CCCCn2cc(nn2)C[C@H](NC(=O)COCCOCCOCCNC(=O)CCCC[C@@H]2SC[C@@H]3NC(=O)N[C@@H]32)C(=O)N[C@H](CO)C(=O)N2CCC[C@@H]2C(=O)N[C@H](Cc2c[nH]c3ccccc23)C(=O)N[C@H](Cc2c[nH]c3ccccc23)C(=O)N1]
Biotin-PEG$_3$-Cy(spww). MALDI-MS (m/z): calcd. for C$_{59}$H$_{79}$N$_{15}$O$_{13}$S (M + H) 1238.57; found 1238.59.
3
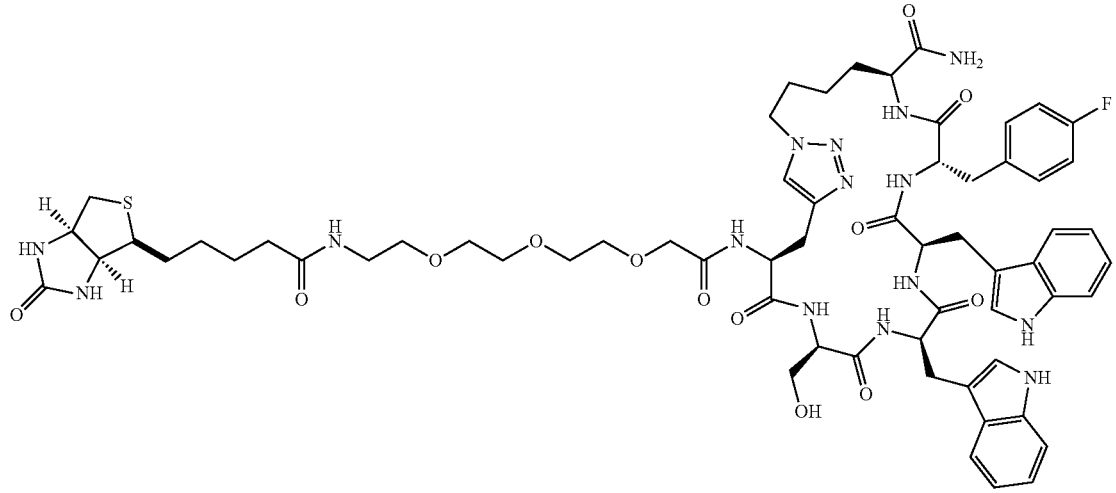 [SMILES: NC(=O)[C@@H]1CCCCn2cc(nn2)C[C@H](NC(=O)COCCOCCOCCNC(=O)CCCC[C@@H]2SC[C@@H]3NC(=O)N[C@@H]32)C(=O)N[C@H](CO)C(=O)N[C@H](Cc2c[nH]c3ccccc23)C(=O)N[C@H](Cc2c[nH]c3ccccc23)C(=O)N[C@@H](Cc2ccc(F)cc2)C(=O)N1]
Biotin-PEG$_3$-Cy(sww(F-Phe)). MALDI-MS (m/z): calcd. for C$_{63}$H$_{80}$FN$_{15}$O$_{13}$S (M + H) 1306.58; found 1306.65.
4
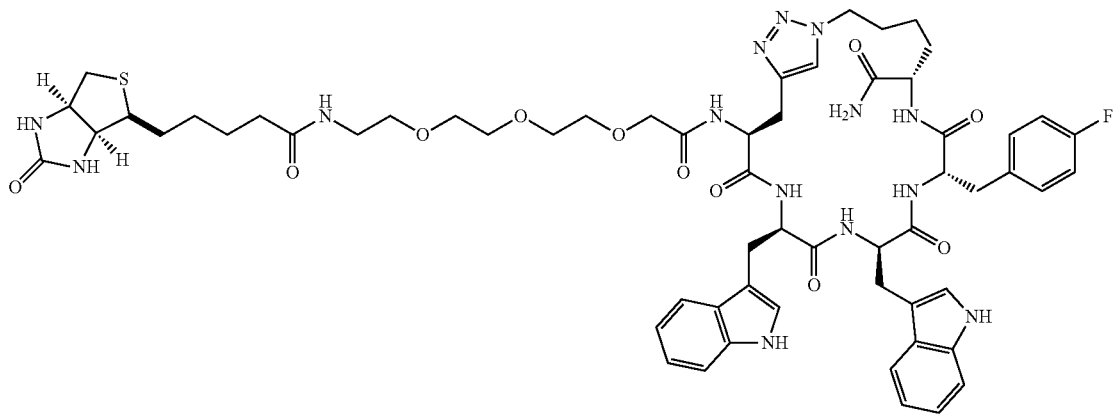 [SMILES: NC(=O)[C@@H]1CCCCn2cc(nn2)C[C@H](NC(=O)COCCOCCOCCNC(=O)CCCC[C@@H]2SC[C@@H]3NC(=O)N[C@@H]32)C(=O)N[C@H](Cc2c[nH]c3ccccc23)C(=O)N[C@H](Cc2c[nH]c3ccccc23)C(=O)N[C@@H](Cc2ccc(F)cc2)C(=O)N1]
Biotin-PEG$_3$-Cy(ww(F-Phe)). MALDI-MS (m/z): calcd. for C$_{60}$H$_{75}$FN$_{14}$O$_{11}$S (M + H) 1219.54; found 1219.29.

TABLE 7
Synthesis Data for nlf(Me-Trp)(F-Phe) 4-mer and 3-mer Variants
1
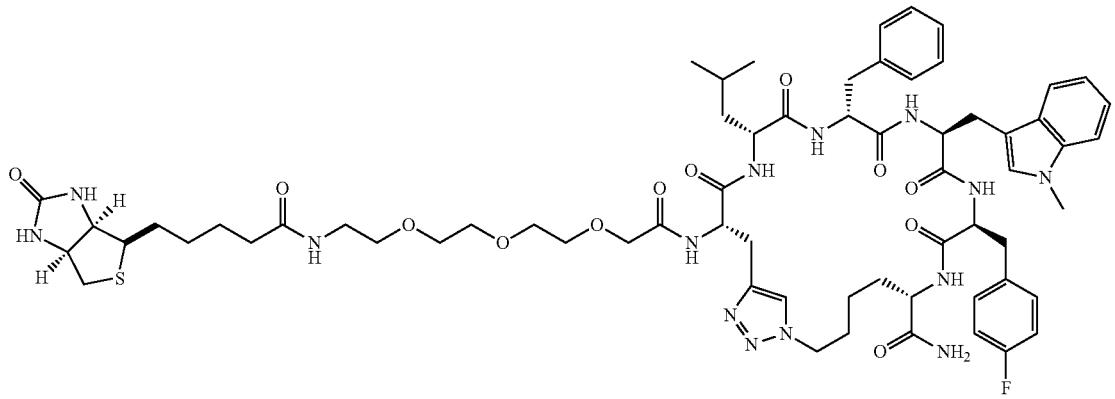 [SMILES: CC(C)C[C@H]1NC(=O)[C@@H](NC(=O)COCCOCCOCCNC(=O)CCCC[C@H]2SC[C@H]3NC(=O)N[C@H]32)Cc2cn(nn2)CCCC[C@@H](C(N)=O)NC(=O)[C@H](Cc2ccc(F)cc2)NC(=O)[C@H](Cc2cn(C)c3ccccc23)NC(=O)[C@@H](Cc2ccccc2)NC1=O]
Biotin-PEG$_3$-Cy(lf(Me-Trp)(F-Phe)). MALDI-MS (m/z): calcd. for C$_{65}$H$_{87}$FN$_{14}$O$_{12}$S
(M + H) 1307.63; found 1307.54.
2
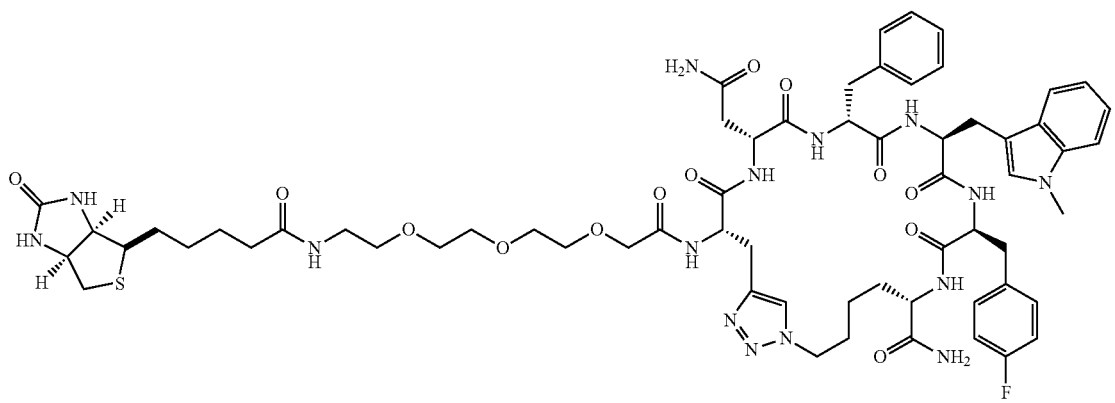 [SMILES: Cn1cc(C[C@@H]2NC(=O)[C@@H](Cc3ccccc3)NC(=O)[C@@H](CC(N)=O)NC(=O)[C@@H](NC(=O)COCCOCCOCCNC(=O)CCCC[C@H]3SC[C@H]4NC(=O)N[C@H]43)Cc3cn(nn3)CCCC[C@@H](C(N)=O)NC(=O)[C@H](Cc3ccc(F)cc3)NC2=O)c2ccccc21]
Biotin-PEG$_3$-Cy(nf(Me-Trp)(F-Phe)). MALDI-MS (m/z): calcd. for C$_{63}$H$_{82}$FN$_{15}$O$_{13}$S
(M + H) 1308.59; found 1308.31.
3
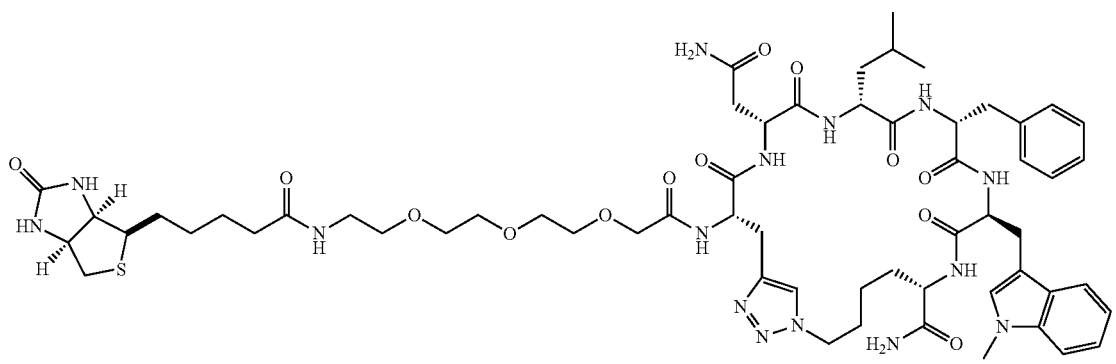 [SMILES: CC(C)C[C@H]1NC(=O)[C@@H](CC(N)=O)NC(=O)[C@@H](NC(=O)COCCOCCOCCNC(=O)CCCC[C@H]2SC[C@H]3NC(=O)N[C@H]32)Cc2cn(nn2)CCCC[C@@H](C(N)=O)NC(=O)[C@H](Cc2cn(C)c3ccccc23)NC(=O)[C@@H](Cc2ccccc2)NC1=O]
Biotin-PEG$_3$-Cy(nlf(Me-Trp)). MALDI-MS (m/z): calcd. for C$_{60}$H$_{85}$N$_{15}$O$_{13}$S (M + H)
1256.62; found 1256.51.

TABLE 7-continued
Synthesis Data for nlf(Me-Trp)(F-Phe) 4-mer and 3-mer Variants
4
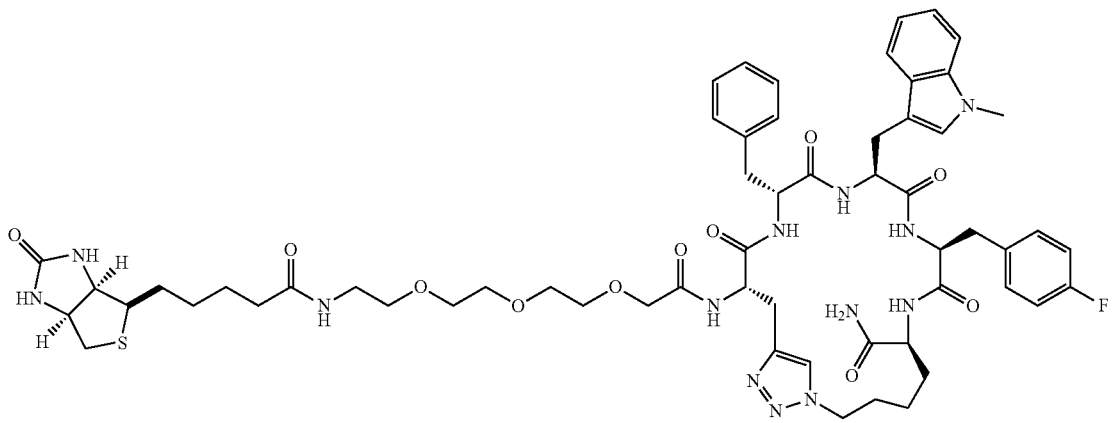 [SMILES: Cn1cc(C[C@@H]2NC(=O)[C@@H](Cc3ccccc3)NC(=O)[C@@H](NC(=O)COCCOCCOCCNC(=O)CCCC[C@H]3SC[C@H]4NC(=O)N[C@H]43)Cc3cn(nn3)CCCC[C@@H](C(N)=O)NC(=O)[C@H](Cc3ccc(F)cc3)NC2=O)c2ccccc21]
Biotin-PEG$_3$-Cy(f(Me-Trp)(F-Phe)). MALDI-MS (m/z): calcd. for C$_{59}$H$_{76}$FN$_{13}$O$_{11}$S (M + H) 1194.55; found 1194.62.
TABLE 8
Synthesis Data for frf(Me-Trp)s 4-mer Variants
1
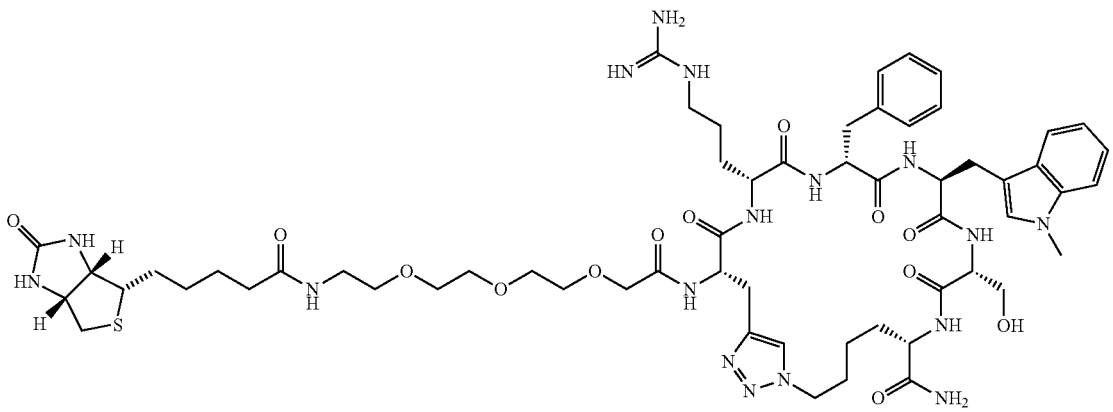 [SMILES: Cn1cc(C[C@@H]2NC(=O)[C@@H](Cc3ccccc3)NC(=O)[C@@H](CCCNC(=N)N)NC(=O)[C@@H](NC(=O)COCCOCCOCCNC(=O)CCCC[C@@H]3SC[C@@H]4NC(=O)N[C@@H]43)Cc3cn(nn3)CCCC[C@@H](C(N)=O)NC(=O)[C@@H](CO)NC2=O)c2ccccc21]
Biotin-PEG$_3$-Cy(rf(Me-Trp)s). MALDI-MS (m/z): calcd. for C$_{59}$H$_{85}$N$_{17}$O$_{13}$S (M + H) 1273.62; found 1273.41.
2
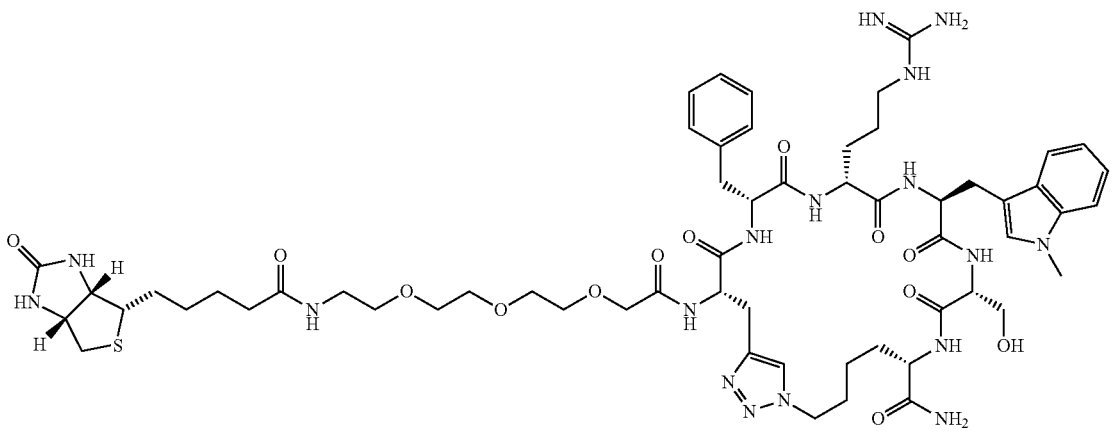 [SMILES: Cn1cc(C[C@@H]2NC(=O)[C@@H](CCCNC(=N)N)NC(=O)[C@@H](Cc3ccccc3)NC(=O)[C@@H](NC(=O)COCCOCCOCCNC(=O)CCCC[C@@H]3SC[C@@H]4NC(=O)N[C@@H]43)Cc3cn(nn3)CCCC[C@@H](C(N)=O)NC(=O)[C@@H](CO)NC2=O)c2ccccc21]
Biotin-PEG$_3$-Cy(fr(Me-Trp)s). MALDI-MS (m/z): calcd. for C$_{59}$H$_{85}$N$_{17}$O$_{13}$S (M + H) 1272.62; found 1273.07.

TABLE 8-continued
Synthesis Data for frf(Me-Trp)s 4-mer Variants
3
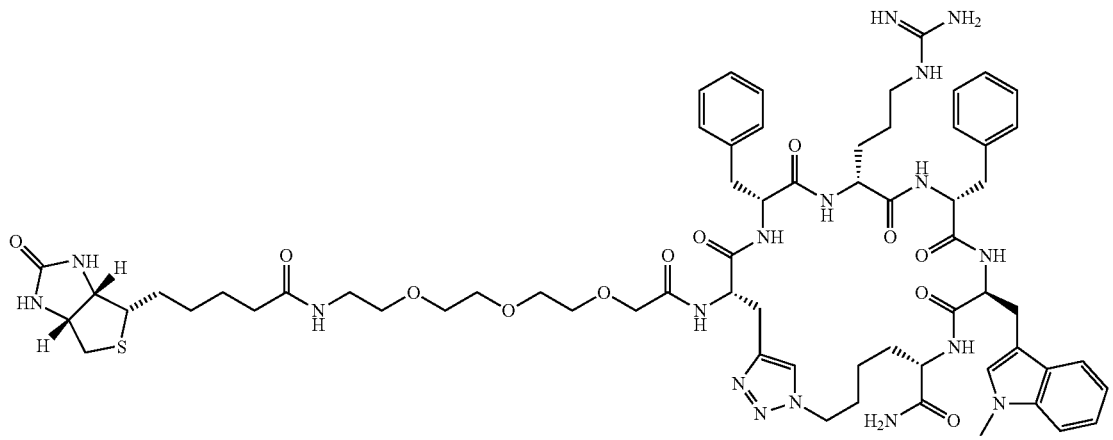 [SMILES: Cn1cc(C[C@@H]2NC(=O)[C@@H](Cc3ccccc3)NC(=O)[C@@H](CCCNC(=N)N)NC(=O)[C@@H](Cc3ccccc3)NC(=O)[C@@H](NC(=O)COCCOCCOCCNC(=O)CCCC[C@@H]3SC[C@@H]4NC(=O)N[C@@H]43)Cc3cn(nn3)CCCC[C@@H](C(N)=O)NC2=O)c2ccccc21]
Biotin-PEG$_3$-Cy(frf(Me-Trp)). MALDI-MS (m/z): calcd. for C$_{65}$H$_{89}$N$_{17}$O$_{12}$S (M + H) 1332.66; found 1333.32.
TABLE 9
Synthesis Data for wyray 4-mer Variants
1
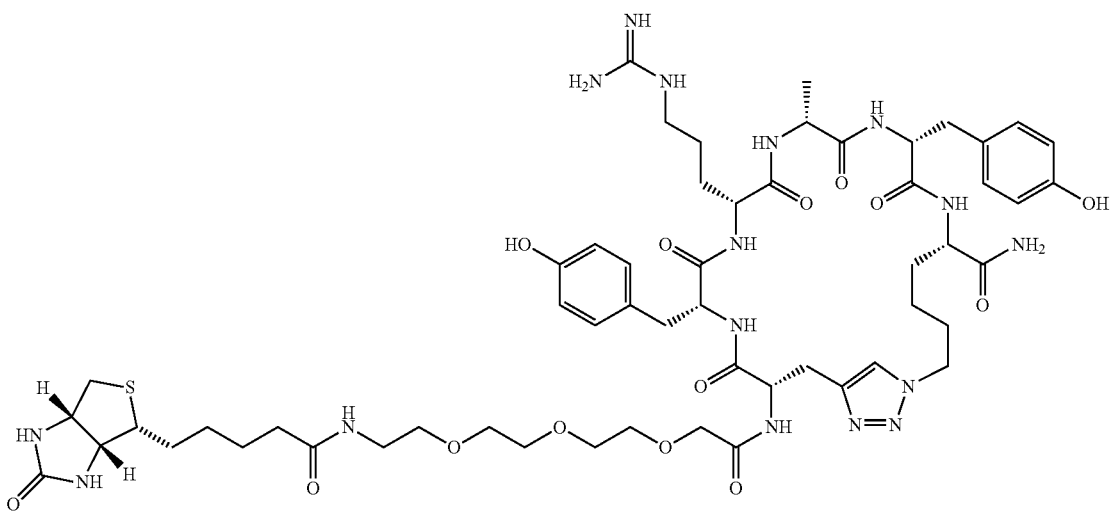 [SMILES: C[C@H]1NC(=O)[C@@H](CCCNC(=N)N)NC(=O)[C@@H](Cc2ccc(O)cc2)NC(=O)[C@@H](NC(=O)COCCOCCOCCNC(=O)CCCC[C@H]2SC[C@H]3NC(=O)N[C@H]32)Cc2cn(nn2)CCCC[C@@H](C(N)=O)NC(=O)[C@@H](Cc2ccc(O)cc2)NC1=O]
Biotin-PEG$_3$-Cy(yray). MALDI-MS (m/z): calcd. for C$_{56}$H$_{82}$N$_{16}$O$_{14}$S (M + H) 1235.59; found 1235.68.

TABLE 9-continued
Synthesis Data for wyray 4-mer Variants
2
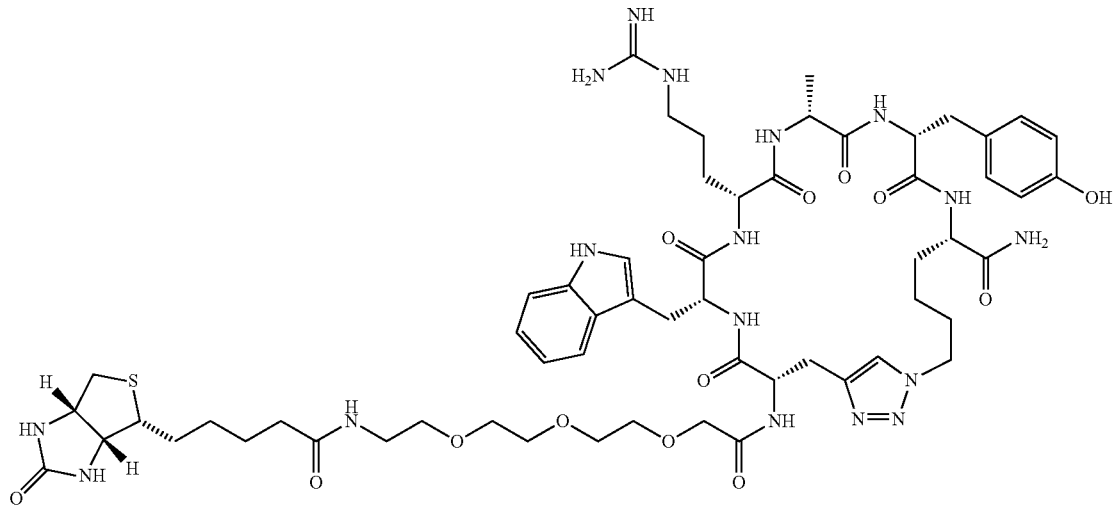 [SMILES: C[C@H]1NC(=O)[C@@H](CCCNC(=N)N)NC(=O)[C@@H](Cc2c[nH]c3ccccc23)NC(=O)[C@@H](NC(=O)COCCOCCOCCNC(=O)CCCC[C@H]2SC[C@H]3NC(=O)N[C@H]32)Cc2cn(nn2)CCCC[C@@H](C(N)=O)NC(=O)[C@@H](Cc2ccc(O)cc2)NC1=O]
Biotin-PEG$_3$-Cy(wray). MALDI-MS (m/z): calcd. for $C_{58}H_{83}N_{17}O_{13}S$ (M + H) 1258.61; found 1259.08.
3
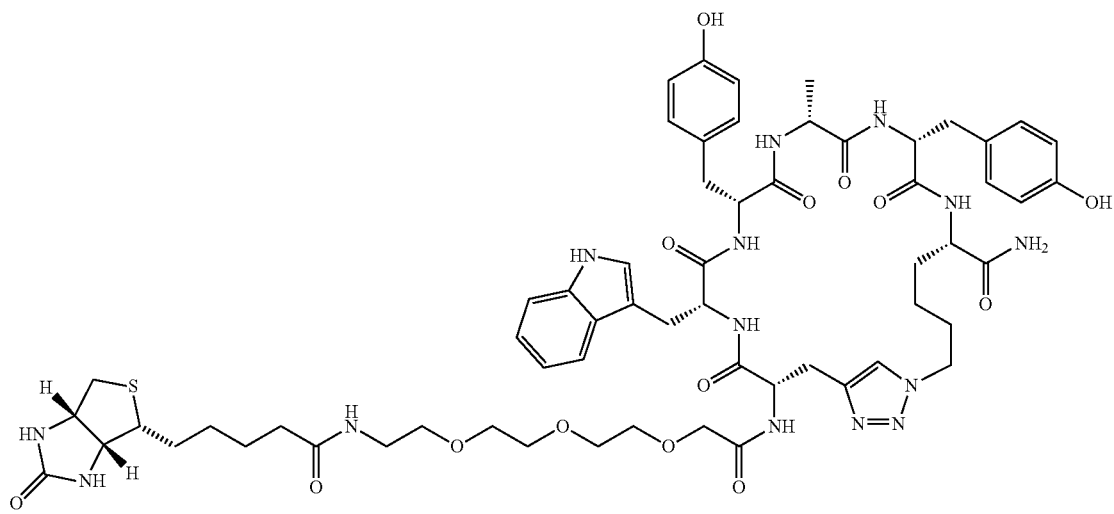 [SMILES: C[C@H]1NC(=O)[C@@H](Cc2ccc(O)cc2)NC(=O)[C@@H](Cc2c[nH]c3ccccc23)NC(=O)[C@@H](NC(=O)COCCOCCOCCNC(=O)CCCC[C@H]2SC[C@H]3NC(=O)N[C@H]32)Cc2cn(nn2)CCCC[C@@H](C(N)=O)NC(=O)[C@@H](Cc2ccc(O)cc2)NC1=O]
Biotin-PEG$_3$-Cy(wyay). MALDI-MS (m/z): calcd. for $C_{61}H_{80}N_{14}O_{14}S$ (M + H) 1265.57; found 1265.69.

TABLE 9-continued

Synthesis Data for wyray 4-mer Variants

4
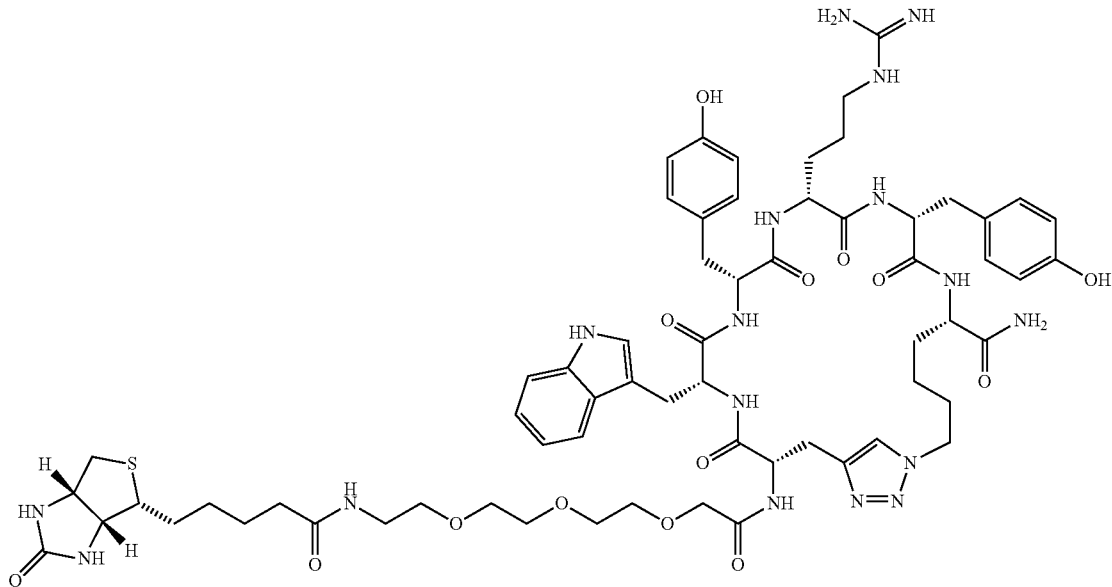 [SMILES: N=C(N)NCCC[C@H]1NC(=O)[C@@H](Cc2ccc(O)cc2)NC(=O)[C@@H](Cc2c[nH]c3ccccc23)NC(=O)[C@@H](NC(=O)COCCOCCOCCNC(=O)CCCC[C@H]2SC[C@H]3NC(=O)N[C@H]32)Cc2cn(nn2)CCCC[C@@H](C(N)=O)NC(=O)[C@@H](Cc2ccc(O)cc2)NC1=O]
Biotin-PEG$_3$-Cy(wyry). MALDI-MS (m/z): calcd. for C$_{64}$H$_{87}$N$_{17}$O$_{14}$S (M + H) 1350.63; found 1350.96.

Figure 15A:
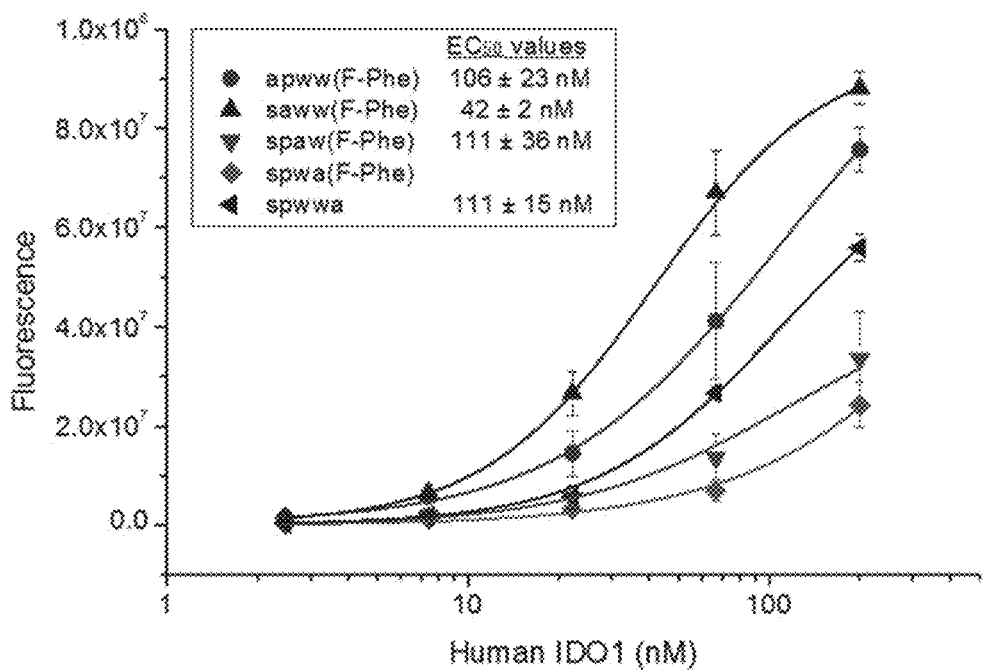
FIGS. 15A and 15B: Optimization of biotin-PEG$_3$-Cy (spww(F-Phe)).
Figure 15B:
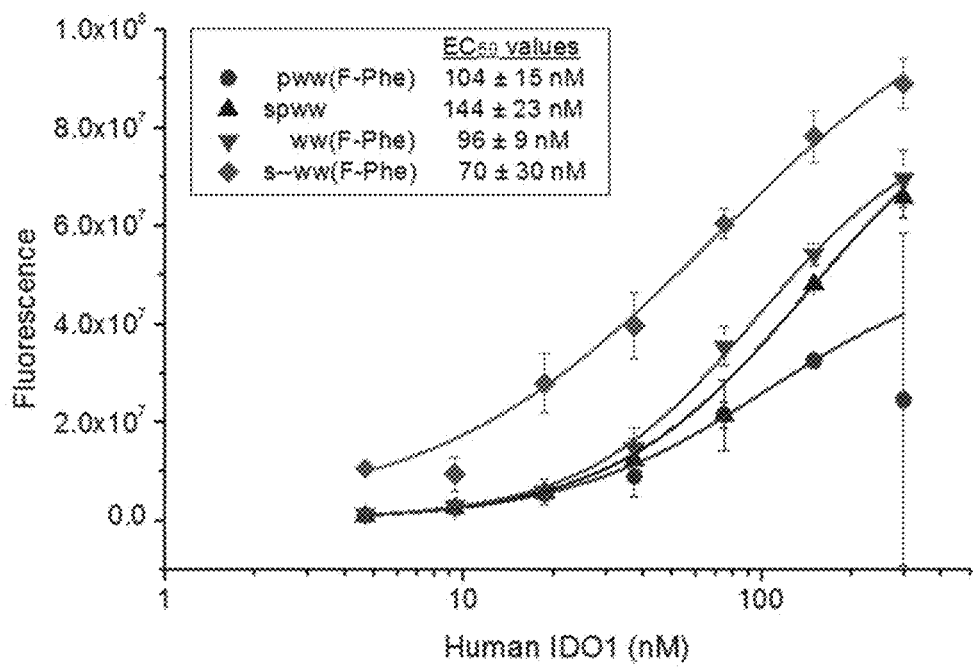

The five single alanine mutants of biotin-PEG$_3$-Cy(spww (F-Phe)) were assayed for binding to human IDO1 (FIG. 15A). Substitution of D-Trp (w) in this macrocycle weakens the binding to IDO1, signifying that D-Trp (w) is important. On the other hand, substitution of D-Pro (p) is tolerated. Macrocycle saww(F-Phe) shows a similar binding affinity to the original spww(F-Phe), with a similar maximum signal. The maximum signal of the 4-mer macrocycle sww(F-Phe), which lacks D-Pro (p), is superior to the other 4-mers generated (FIG. 15B).

Figure 16A:
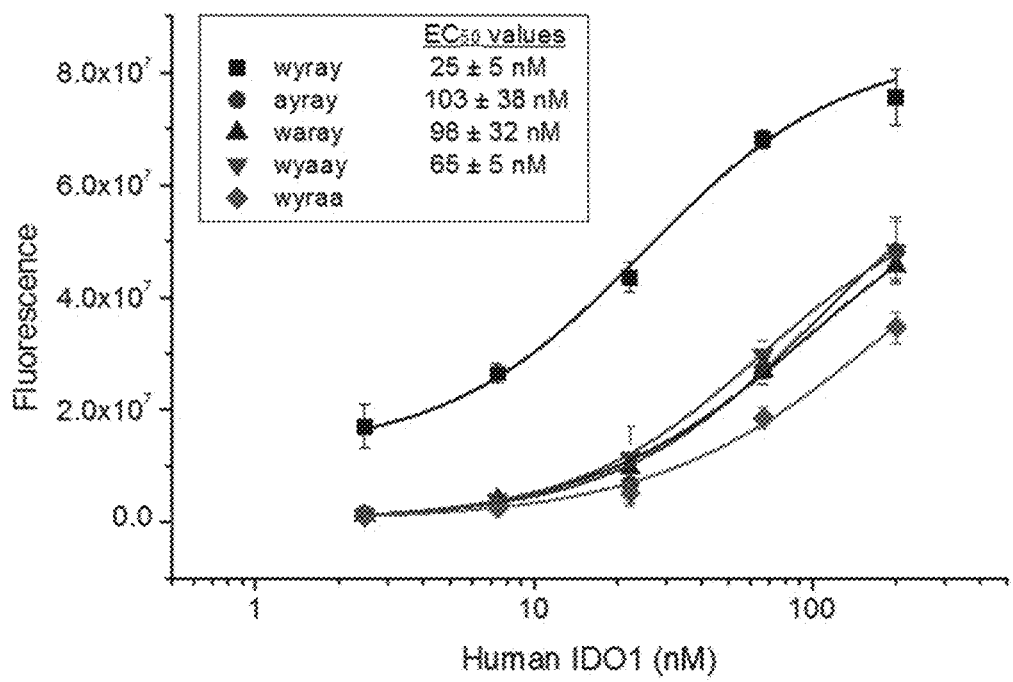
FIGS. 16A and 16B: Optimization of biotin-PEG$_3$-Cy (wyray).
Figure 16B:
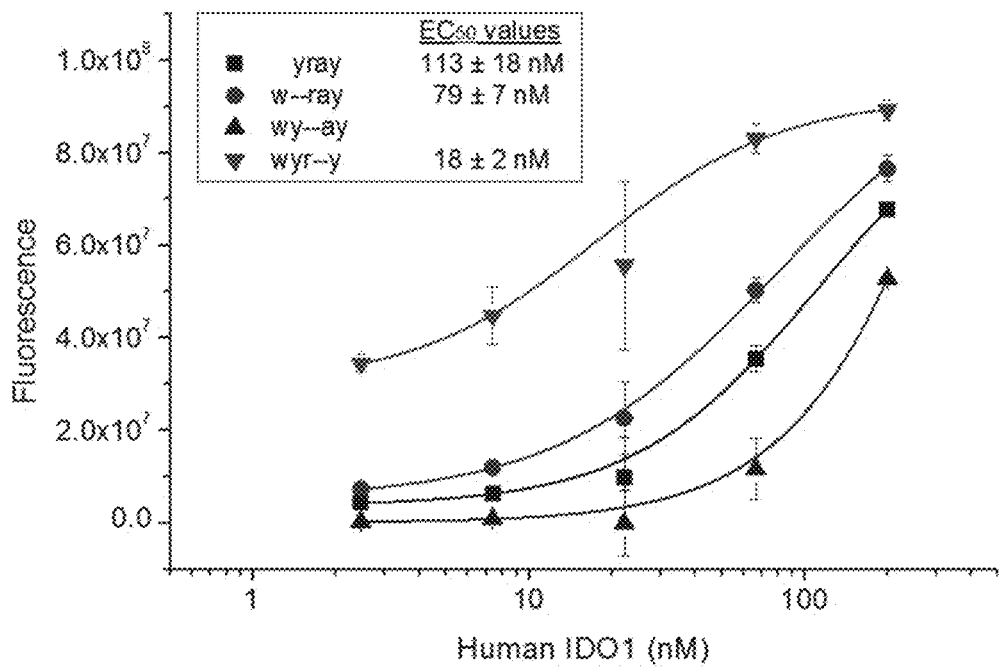

The four single alanine mutants of biotin-PEG$_3$-Cy (wyray) were assayed for binding to human IDO1 (FIG. 16A). Substituting any of the positions causes a small perturbation to IDO1 binding. The EC$_{50}$ values for these alanine mutants are similar, suggesting that all residues are equally important for IDO1 binding. Macrocycle wyry exhibited the best affinity among the 4-mer macrocycles suggesting that the D-Ala (a) is not required for IDO1 binding (FIG. 16B).

Figure 17A:
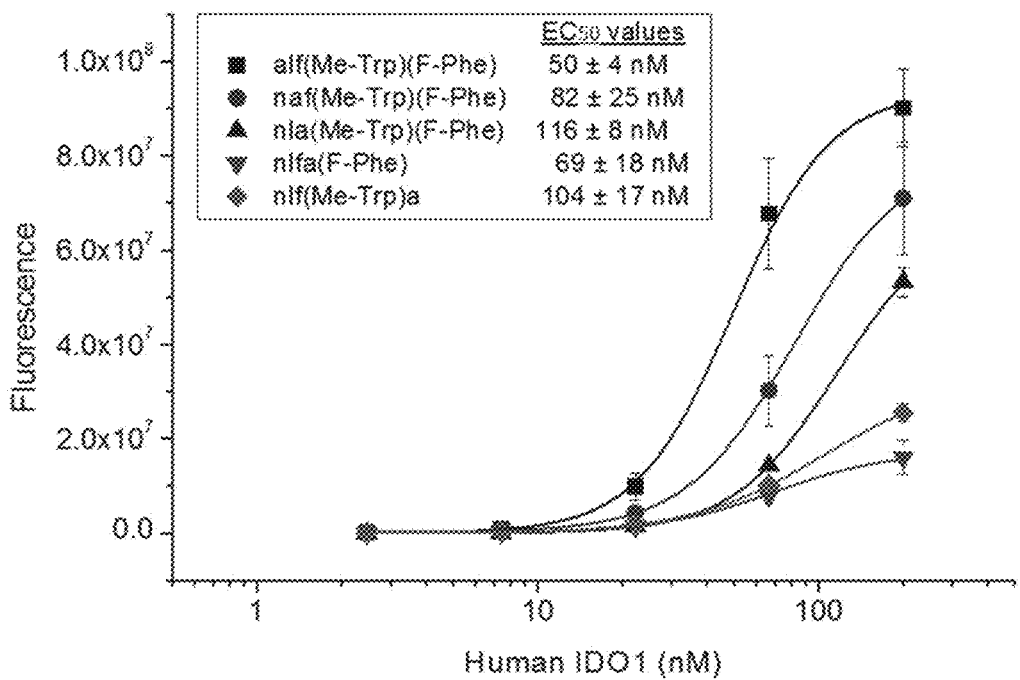
FIGS. 17A and 17B: Optimization of biotin-PEG$_3$-Cy(nlf (Me-Trp)(F-Phe)).
Figure 17B:
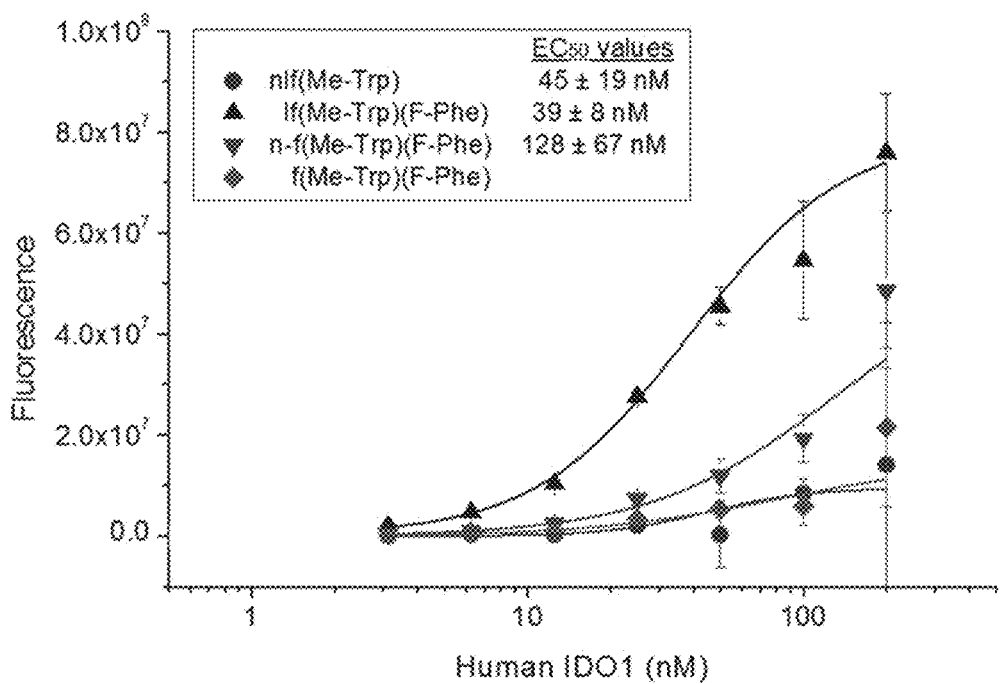

The five single alanine mutants of biotin-PEG$_3$-Cy(nlf (Me-Trp)(F-Phe)) were assayed for binding to human IDO1 (FIG. 17A). Making substitutions to the C-terminus of this macrocycle weakens the binding to IDO1, signifying that the C-terminus is important. The 4-mer macrocycle lf(Me-Trp)(F-Phe) only demonstrated a slight decrease in binding affinity when compared to the original 5-mer (FIG. 17B).

Figure 18A:
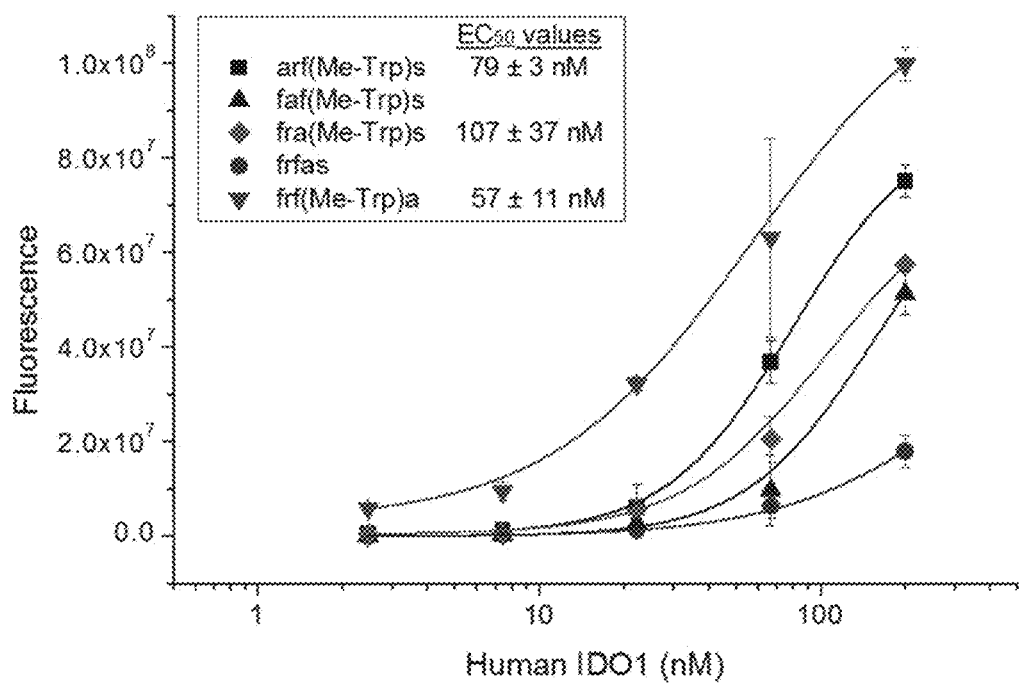
FIGS. 18A and 18B: Optimization of biotin-PEG$_3$-Cy(frf (Me-Trp)s).
Figure 18B:
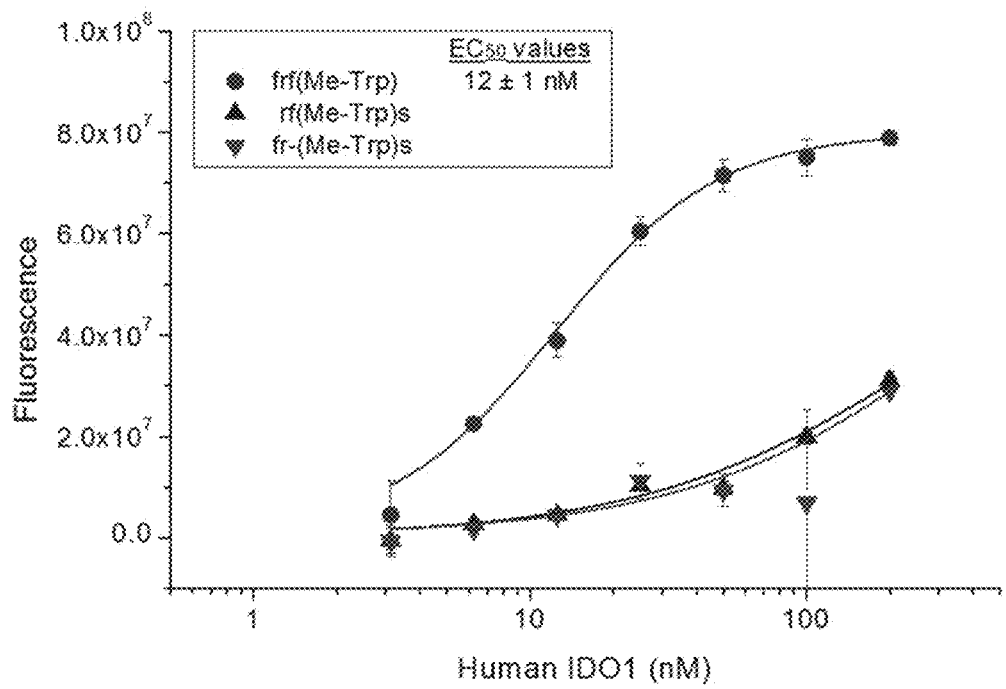

The five single alanine mutants of biotin-PEG$_3$-Cy(frf (Me-Trp)s) were assayed for binding to human IDO1 (FIG. 18A). Me-Trp appears to be the key amino acid for binding. Macrocycle frfas shows the weakest binding to IDO1. Substitution of the N- and C-termini of this macrocycle anchor is tolerated with a small loss of binding affinity. The 4-mer macrocycle frf(Me-Trp) shows a similar binding affinity to the original frf(Me-Trp)s, with a similar maximum signal (FIG. 18B).

The invention claimed is:

1. A binding agent that specifically binds indoleamine 2,3-dioxygenase 1 (IDO1) comprising a first ligand having affinity for an epitope on IDO1, wherein the ligand comprises a cyclic peptide having an amino acid sequence selected from the group consisting of:
   (a) X1rf(Me-Trp)X2, wherein X1 and X2 are independently D-Ala, D-Arg, D-Asn, D-Asp, D-Glu, Gly, D-His, D-Leu, D-Lys, D-Phe, D-Pro, D-Ser, D-Thr, D-Trp, D-Tyr, or D-Val or is not present;
   (b) nsfr(Me-Trp);
   (c) wyrX3y, wherein X3 is D-Ala or is not present;
   (d) rys(Me-Trp)r;
   (e) X4lf(Me-Trp)(F-Phe), wherein X4 is D-Ala, D-Arg, D-Asn, D-Asp, D-Glu, Gly, D-His, D-Leu, D-Lys, D-Phe, D-Pro, D-Ser, D-Thr, D-Trp, D-Tyr, or D-Val or is not present;
   (f) nlw(Me-Trp)r;
   (g) sX5ww(F-Phe), wherein X5 is D-Ala, D-Arg, D-Asn, D-Asp, D-Glu, Gly, D-His, D-Leu, D-Lys, D-Phe, D-Pro, D-Ser, D-Thr, D-Trp, D-Tyr, or D-Val or is not present;
   (h) rffyl; and
   (i) nsh(F-Phe)r.

2. The binding agent of claim 1, wherein the epitope comprises the amino acid sequence GFWEDPKEF-AGGSAGQSSVFQ (SEQ ID NO:1).

3. The binding agent of claim 1, wherein the cyclic peptide of the ligand has an amino acid sequence selected from the group consisting of:
   a. X1rf(Me-Trp)X2, wherein X1 and X2 are independently D-Ala, D-Arg, D-Asn, D-Asp, D-Glu, Gly, D-His, D-Leu, D-Lys, D-Phe, D-Pro, D-Ser, D-Thr, D-Trp, D-Tyr, or D-Val or is not present;
   b. nsfr(Me-Trp); and
   c. wyrX3y, wherein X3 is D-Ala or is not present.

4. The binding agent of claim 1, wherein the cyclic peptide of the ligand has an amino acid sequence selected from the group consisting of frf(Me-Trp)s, arf(Me-Trp)s, rf(Me-Trp)s, frf(Me-Trp)a, frf(Me-Trp), and rf(Me-Trp).

5. The binding agent of claim 1, wherein the cyclic peptide of the ligand has an amino acid sequence of wyray or wyry.

6. The binding agent of claim 1, wherein the epitope comprises the amino acid sequence LPPILVYADCVLANWKKKDPNK (SEQ ID NO:2).

7. The binding agent of claim 1, wherein the cyclic peptide of the ligand has an amino acid sequence selected from the group consisting of:
   a. rys(Me-Trp)r;
   b. X4lf(Me-Trp)(F-Phe), wherein X4 is D-Ala, D-Arg, D-Asn, D-Asp, D-Glu, Gly, D-His, D-Leu, D-Lys, D-Phe, D-Pro, D-Ser, D-Thr, D-Trp, D-Tyr, or D-Val or is not present;
   c. nlw(Me-Trp)r; and
   d. sX5ww(F-Phe), wherein X5 is D-Ala, D-Arg, D-Asn, D-Asp, D-Glu, Gly, D-His, D-Leu, D-Lys, D-Phe, D-Pro, D-Ser, D-Thr, D-Trp, D-Tyr, or D-Val or is not present.

8. The binding agent of claim 1, wherein the cyclic peptide of the ligand has an amino acid sequence of nlf(Me-Trp)(F-Phe), alf(Me-Trp)(F-Phe), or lf(Me-Trp)(F-Phe).

9. The binding agent of claim 1, wherein the cyclic peptide of the ligand has an amino acid sequence of spww(F-Phe), saww(F-Phe), or sww(F-Phe).

10. The binding agent of claim 1, wherein the epitope comprises the amino acid sequence NKPLTYENMDVLFSFR (SEQ ID NO:3).

11. The binding agent of claim 1, wherein the cyclic peptide of the ligand has an amino acid sequence selected from the group consisting of:
   a. rffyl; and
   b. nsh(F-Phe)r.

12. The binding agent of claim 1, wherein the binding agent further comprises a small molecule that inhibits the activity of IDO1, optionally wherein the small molecule is covalently attached to the ligand.

13. A binding agent that specifically binds IDO1, wherein the binding agent comprises a first ligand having affinity for a first epitope on IDO1, a second ligand having affinity for a second epitope on IDO1, and a linker covalently connecting the first ligand to the second ligand, wherein the first and second ligands each comprises a cyclic peptide,
   wherein the cyclic peptide of the first ligand has an amino acid sequence selected from one of the groups (1), (2), or (3) and wherein the cyclic peptide of the second ligand has an amino acid sequence selected from one of the two groups from which the amino acid sequence of the cyclic peptide of the first ligand was not selected, wherein group (1) consists of:
      (a) X1rf(Me-Trp)X2, wherein X1 and X2 are independently D-Ala, D-Arg, D-Asn, D-Asp, D-Glu, Gly, D-His, D-Leu, D-Lys, D-Phe, D-Pro, D-Ser, D-Thr, D-Trp, D-Tyr, or D-Val or is not present;
      (b) nsfr(Me-Trp); and
      (c) wyrX3y, wherein X3 is D-Ala or is not present, wherein group (2) consists of:
      (d) rys(Me-Trp)r;
      (e) X4lf(Me-Trp)(F-Phe), wherein X4 is D-Ala, D-Arg, D-Asn, D-Asp, D-Glu, Gly, D-His, D-Leu, D-Lys, D-Phe, D-Pro, D-Ser, D-Thr, D-Trp, D-Tyr, or D-Val or is not present;
      (f) nlw(Me-Trp)r; and
      (g) sX5ww(F-Phe), wherein X5 is D-Ala, D-Arg, D-Asn, D-Asp, D-Glu, Gly, D-His, D-Leu, D-Lys, D-Phe, D-Pro, D-Ser, D-Thr, D-Trp, D-Tyr, or D-Val or is not present, and
   wherein group (3) consists of:
      (h) rffyl; and
      (i) nsh(F-Phe)r.

14. The binding agent of claim 13, wherein the cyclic peptide of either the first ligand or the second ligand comprises a 1,4-substituted-1,2,3-triazole residue (Tz4) or a 1,5-substituted-1,2,3-triazole residue (Tz5).

15. The binding agent of claim 14, wherein the triazole residue is a 1,4-substituted-1,2,3-triazole (Tz4) residue.

16. The binding agent of claim 13, wherein the length of the linker corresponds to the distance between the first epitope and the second epitope.

17. The binding agent of claim 16, wherein the length of the linker is from about 11 Å to about 38 Å.

18. The binding agent of claim 1, wherein the binding agent further comprises a detectable moiety.

19. The binding agent of claim 18, wherein the detectable moiety is selected from the group consisting of biotin, copper-DOTA, biotin-PEG$_3$, aminooxyacetate, $^{19}$FB, $^{18}$FB, and FITC-PEG$_3$.

20. The binding agent of claim 19, wherein the detectable moiety is selected from the group consisting of $^{64}$Cu DOTA, $^{68}$Ga DOTA, $^{68}$Ga NOTA, $^{18}$F, Al$^{18}$F NOTA, $^{64}$Cu, $^{68}$Ga, $^{89}$Zr, $^{124}$I, $^{86}$Y, $^{94m}$Tc, $^{110m}$In, $^{11}$C and $^{76}$Br.

21. A method of detecting IDO1 in a biological sample, comprising contacting the biological sample with the binding agent of claim 13.

22. A method of reducing IDO1 enzymatic activity comprising contacting IDO1 with an effective amount of a binding agent of claim 1, thereby reducing IDO1 enzymatic activity.

23. A method of detecting IDO1 comprising contacting IDO1 with an effective amount of a binding agent of claim 1.

24. A binding agent that specifically binds indoleamine 2,3-dioxygenase 1 (IDO1) produced by a method comprising
   (a) contacting an epitope of IDO1 to a library of molecules wherein each member of the library comprise distinct cyclic peptides of 5-10 amino acids and an acetylene click handle, wherein the amino acids are D-amino acids, artificial amino acids, or combinations thereof, and wherein the epitope of the IDO1 comprises an azide click handle, wherein the epitope comprises the amino acid sequence GFWEDPKEFAGGSAGQSSVFQ (SEQ ID NO:1), LPPILVYADCVLANWKKKDPNK (SEQ ID NO:2), or NKPLTYENMDVLFSFR (SEQ ID NO:3);
   (b) allowing a member of the library to covalently bind to the azide click handle of the epitope; and
   (c) identifying the amino acid sequence of the library member that covalently binds to the azide click handle of the epitope, wherein the identified amino acid sequence is selected for forming a binding agent having affinity for the epitope of IDO1.

25. The binding agent of claim 1, wherein the cyclic peptide comprises a 1,4-substituted-1,2,3-triazole residue (Tz4) or a 1,5-substituted-1,2,3-triazole residue (Tz5).

26. The binding agent of claim 25, wherein the triazole residue is a 1,4-substituted-1,2,3-triazole (Tz4) residue.

* * * * *

SEQUENCE LISTING

<160> NUMBER OF SEQ ID NOS: 21

<210> SEQ ID NO 1
<211> LENGTH: 21
<212> TYPE: PRT
<213> ORGANISM: Homo sapiens

<400> SEQUENCE: 1

Gly Phe Trp Glu Asp Pro Lys Glu Phe Ala Gly Gly Ser Ala Gly Gln
1               5                   10                  15

Ser Ser Val Phe Gln
            20

```
<210> SEQ ID NO 2
<211> LENGTH: 22
<212> TYPE: PRT
<213> ORGANISM: Homo sapiens

<400> SEQUENCE: 2

Leu Pro Pro Ile Leu Val Tyr Ala Asp Cys Val Leu Ala Asn Trp Lys
1               5                   10                  15

Lys Lys Asp Pro Asn Lys
            20

<210> SEQ ID NO 3
<211> LENGTH: 16
<212> TYPE: PRT
<213> ORGANISM: Homo sapiens

<400> SEQUENCE: 3

Asn Lys Pro Leu Thr Tyr Glu Asn Met Asp Val Leu Phe Ser Phe Arg
1               5                   10                  15

<210> SEQ ID NO 4
<211> LENGTH: 21
<212> TYPE: PRT
<213> ORGANISM: Artificial Sequence
<220> FEATURE:
<223> OTHER INFORMATION: Synthetic Peptide
<220> FEATURE:
<221> NAME/KEY: MISC_FEATURE
<222> LOCATION: (9)..(9)
<223> OTHER INFORMATION: Xaa is L-azidolysine

<400> SEQUENCE: 4

Gly Phe Trp Glu Asp Pro Lys Glu Xaa Ala Gly Gly Ser Ala Gly Gln
1               5                   10                  15

Ser Ser Val Phe Gln
            20

<210> SEQ ID NO 5
<211> LENGTH: 22
<212> TYPE: PRT
<213> ORGANISM: Artificial Sequence
<220> FEATURE:
<223> OTHER INFORMATION: Synthetic Peptide
<220> FEATURE:
<221> NAME/KEY: MISC_FEATURE
<222> LOCATION: (12)..(12)
<223> OTHER INFORMATION: Xaa is L-azidolysine

<400> SEQUENCE: 5

Leu Pro Pro Ile Leu Val Tyr Ala Asp Cys Val Xaa Ala Asn Trp Lys
1               5                   10                  15

Lys Lys Asp Pro Asn Lys
            20

<210> SEQ ID NO 6
<211> LENGTH: 16
<212> TYPE: PRT
<213> ORGANISM: Artificial Sequence
<220> FEATURE:
<223> OTHER INFORMATION: Synthetic Peptide
<220> FEATURE:
<221> NAME/KEY: MISC_FEATURE
<222> LOCATION: (10)..(10)
<223> OTHER INFORMATION: Xaa is L-azidolysine

<400> SEQUENCE: 6

Asn Lys Pro Leu Thr Tyr Glu Asn Met Xaa Val Leu Phe Ser Phe Arg
```

<210> SEQ ID NO 7
<211> LENGTH: 7
<212> TYPE: PRT
<213> ORGANISM: Artificial Peptide
<220> FEATURE:
<223> OTHER INFORMATION: Synthetic Peptide

<400> SEQUENCE: 7

His His His His His His His
1               5

<210> SEQ ID NO 8
<211> LENGTH: 402
<212> TYPE: PRT
<213> ORGANISM: Homo sapiens

<400> SEQUENCE: 8

Ala His Ala Met Glu Asn Ser Trp Thr Ile Ser Lys Glu Tyr His Ile
1               5                   10                  15

Asp Glu Glu Val Gly Phe Ala Leu Pro Asn Pro Gln Glu Asn Leu Pro
                20                  25                  30

Asp Phe Tyr Asn Asp Trp Met Phe Ile Ala Lys His Leu Pro Asp Leu
            35                  40                  45

Ile Glu Ser Gly Gln Leu Arg Glu Arg Val Glu Lys Leu Asn Met Leu
50                  55                  60

Ser Ile Asp His Leu Thr Asp His Lys Ser Gln Arg Leu Ala Arg Leu
65                  70                  75                  80

Val Leu Gly Cys Ile Thr Met Ala Tyr Val Trp Gly Lys Gly His Gly
                85                  90                  95

Asp Val Arg Lys Val Leu Pro Arg Asn Ile Ala Val Pro Tyr Cys Gln
            100                 105                 110

Leu Ser Lys Lys Leu Glu Leu Pro Pro Ile Leu Val Tyr Ala Asp Cys
        115                 120                 125

Val Leu Ala Asn Trp Lys Lys Lys Asp Pro Asn Lys Pro Leu Thr Tyr
130                 135                 140

Glu Asn Met Asp Val Leu Phe Ser Phe Arg Asp Gly Asp Cys Ser Lys
145                 150                 155                 160

Gly Phe Phe Leu Val Ser Leu Leu Val Glu Ile Ala Ala Ala Ser Ala
                165                 170                 175

Ile Lys Val Ile Pro Thr Val Phe Lys Ala Met Gln Met Gln Glu Arg
            180                 185                 190

Asp Thr Leu Leu Lys Ala Leu Leu Glu Ile Ala Ser Cys Leu Glu Lys
        195                 200                 205

Ala Leu Gln Val Phe His Gln Ile His Asp His Val Asn Pro Lys Ala
        210                 215                 220

Phe Phe Ser Val Leu Arg Ile Tyr Leu Ser Gly Trp Lys Gly Asn Pro
225                 230                 235                 240

Gln Leu Ser Asp Gly Leu Val Tyr Glu Gly Phe Trp Glu Asp Pro Lys
                245                 250                 255

Glu Phe Ala Gly Gly Ser Ala Gly Gln Ser Ser Val Phe Gln Cys Phe
            260                 265                 270

Asp Val Leu Leu Gly Ile Gln Gln Thr Ala Gly Gly His Ala Ala
        275                 280                 285

Gln Phe Leu Gln Asp Met Arg Arg Tyr Met Pro Pro Ala His Arg Asn
        290                 295                 300

```
Phe Leu Cys Ser Leu Glu Ser Asn Pro Ser Val Arg Glu Phe Val Leu
305                 310                 315                 320

Ser Lys Gly Asp Ala Gly Leu Arg Glu Ala Tyr Asp Ala Cys Val Lys
                325                 330                 335

Ala Leu Val Ser Leu Arg Ser Tyr His Leu Gln Ile Val Thr Lys Tyr
                340                 345                 350

Ile Leu Ile Pro Ala Ser Gln Gln Pro Lys Glu Asn Lys Thr Ser Glu
                355                 360                 365

Asp Pro Ser Lys Leu Glu Ala Lys Gly Thr Gly Thr Asp Leu Met
370                 375                 380

Asn Phe Leu Lys Thr Val Arg Ser Thr Thr Glu Lys Ser Leu Leu Lys
385                 390                 395                 400

Glu Gly

<210> SEQ ID NO 9
<211> LENGTH: 406
<212> TYPE: PRT
<213> ORGANISM: Mus musculus

<400> SEQUENCE: 9

Ala Leu Ser Lys Ile Ser Pro Thr Glu Gly Ser Arg Arg Ile Leu Glu
1               5                   10                  15

Asp His His Ile Asp Glu Asp Val Gly Phe Ala Leu Pro His Pro Leu
                20                  25                  30

Val Glu Leu Pro Asp Ala Tyr Ser Pro Trp Val Leu Val Ala Arg Asn
                35                  40                  45

Leu Pro Val Leu Ile Glu Asn Gly Gln Leu Arg Glu Glu Val Glu Lys
50                  55                  60

Leu Pro Thr Leu Ser Thr Asp Gly Leu Arg Gly His Arg Leu Gln Arg
65                  70                  75                  80

Leu Ala His Leu Ala Leu Gly Tyr Ile Thr Met Ala Tyr Val Trp Asn
                85                  90                  95

Arg Gly Asp Asp Asp Val Arg Lys Val Leu Pro Arg Asn Ile Ala Val
                100                 105                 110

Pro Tyr Cys Glu Leu Ser Glu Lys Leu Gly Leu Pro Pro Ile Leu Ser
                115                 120                 125

Tyr Ala Asp Cys Val Leu Ala Asn Trp Lys Lys Lys Asp Pro Asn Gly
                130                 135                 140

Pro Met Thr Tyr Glu Asn Met Asp Ile Leu Phe Ser Phe Pro Gly Gly
145                 150                 155                 160

Asp Cys Asp Lys Gly Phe Phe Leu Val Ser Leu Leu Val Glu Ile Ala
                165                 170                 175

Ala Ser Pro Ala Ile Lys Ala Ile Pro Thr Val Ser Ser Ala Val Glu
                180                 185                 190

Arg Gln Asp Leu Lys Ala Leu Glu Lys Ala Leu His Asp Ile Ala Thr
                195                 200                 205

Ser Leu Glu Lys Ala Lys Glu Ile Phe Lys Arg Met Arg Asp Phe Val
                210                 215                 220

Asp Pro Asp Thr Phe Phe His Val Leu Arg Ile Tyr Leu Ser Gly Trp
225                 230                 235                 240

Lys Cys Ser Ser Lys Leu Pro Glu Gly Leu Tyr Glu Gly Val Trp
                245                 250                 255

Asp Thr Pro Lys Met Phe Ser Gly Gly Ser Ala Gly Gln Ser Ser Ile
                260                 265                 270
```

```
Phe Gln Ser Leu Asp Val Leu Gly Ile Lys His Glu Ala Gly Lys
        275                 280                 285

Glu Ser Pro Ala Glu Phe Leu Gln Glu Met Arg Glu Tyr Met Pro Pro
290                 295                 300

Ala His Arg Asn Phe Leu Phe Leu Glu Ser Ala Pro Pro Val Arg
305                 310                 315                 320

Glu Phe Val Ile Ser Arg His Asn Glu Asp Leu Thr Lys Ala Tyr Asn
                325                 330                 335

Glu Cys Val Asn Gly Leu Val Ser Val Arg Lys Phe His Leu Ala Ile
                340                 345                 350

Val Asp Thr Tyr Ile Met Lys Pro Ser Lys Lys Pro Thr Asp Gly
            355                 360                 365

Asp Lys Ser Glu Glu Pro Ser Asn Val Glu Ser Arg Gly Thr Gly Gly
370                 375                 380

Thr Asn Pro Met Thr Phe Leu Arg Ser Val Lys Asp Thr Thr Glu Lys
385                 390                 395                 400

Ala Leu Leu Ser Trp Pro
                405

<210> SEQ ID NO 10
<211> LENGTH: 21
<212> TYPE: PRT
<213> ORGANISM: Mus musculus

<400> SEQUENCE: 10

Gly Val Trp Asp Thr Pro Lys Met Phe Ser Gly Gly Ser Ala Gly Gln
1               5                   10                  15

Ser Ser Ile Phe Gln
            20

<210> SEQ ID NO 11
<211> LENGTH: 21
<212> TYPE: PRT
<213> ORGANISM: Artificial Sequence
<220> FEATURE:
<223> OTHER INFORMATION: Synthetic Peptide
<220> FEATURE:
<221> NAME/KEY: MISC_FEATURE
<222> LOCATION: (9)..(9)
<223> OTHER INFORMATION: Xaa is L-azidolysine

<400> SEQUENCE: 11

Gly Phe Trp Glu Asp Pro Lys Glu Xaa Ala Gly Gly Ser Ala Gly Gln
1               5                   10                  15

Ser Ser Val Phe Gln
            20

<210> SEQ ID NO 12
<211> LENGTH: 22
<212> TYPE: PRT
<213> ORGANISM: Mus musculus

<400> SEQUENCE: 12

Leu Pro Pro Ile Leu Ser Tyr Ala Asp Cys Val Leu Ala Asn Trp Lys
1               5                   10                  15

Lys Lys Asp Pro Asn Gly
            20

<210> SEQ ID NO 13
<211> LENGTH: 22
```

```
<212> TYPE: PRT
<213> ORGANISM: Artificial Sequence
<220> FEATURE:
<223> OTHER INFORMATION: Synthetic Peptide
<220> FEATURE:
<221> NAME/KEY: MISC_FEATURE
<222> LOCATION: (12)..(12)
<223> OTHER INFORMATION: Xaa is L-azidolysine

<400> SEQUENCE: 13

Leu Pro Pro Ile Leu Val Tyr Ala Asp Cys Val Xaa Ala Asn Trp Lys
1               5                   10                  15

Lys Lys Asp Pro Asn Lys
            20

<210> SEQ ID NO 14
<211> LENGTH: 16
<212> TYPE: PRT
<213> ORGANISM: Mus musculus

<400> SEQUENCE: 14

Asn Gly Pro Met Thr Tyr Glu Asn Met Asp Ile Leu Phe Ser Phe Pro
1               5                   10                  15

<210> SEQ ID NO 15
<211> LENGTH: 16
<212> TYPE: PRT
<213> ORGANISM: Artificial Peptide
<220> FEATURE:
<223> OTHER INFORMATION: Synthetic Peptide
<220> FEATURE:
<221> NAME/KEY: MISC_FEATURE
<222> LOCATION: (10)..(10)
<223> OTHER INFORMATION: Xaa is L-azidolysine

<400> SEQUENCE: 15

Asn Lys Pro Leu Thr Tyr Glu Asn Met Xaa Val Leu Phe Ser Phe Arg
1               5                   10                  15

<210> SEQ ID NO 16
<211> LENGTH: 21
<212> TYPE: PRT
<213> ORGANISM: Artificial Sequence
<220> FEATURE:
<223> OTHER INFORMATION: Synthetic Peptide

<400> SEQUENCE: 16

Gly Phe Trp Glu Asp Pro Lys Glu Phe Ala Gly Gly Ser Ala Gly Gln
1               5                   10                  15

Ser Ser Val Phe Gln
            20

<210> SEQ ID NO 17
<211> LENGTH: 21
<212> TYPE: PRT
<213> ORGANISM: Artificial Sequence
<220> FEATURE:
<223> OTHER INFORMATION: Synthetic Peptide

<400> SEQUENCE: 17

Gly Phe Trp Glu Asp Pro Lys Glu Phe Gln Ala Phe Gly Val Gly Ser
1               5                   10                  15

Ser Ala Gln Gly Ser
            20

<210> SEQ ID NO 18
```

```
<211> LENGTH: 21
<212> TYPE: PRT
<213> ORGANISM: Artificial Sequence
<220> FEATURE:
<223> OTHER INFORMATION: Synthetic Pepitde

<400> SEQUENCE: 18

Glu Pro Asp Phe Lys Glu Trp Gly Phe Ala Gly Gly Ser Ala Gly Gln
1               5                   10                  15

Ser Ser Val Phe Gln
            20

<210> SEQ ID NO 19
<211> LENGTH: 22
<212> TYPE: PRT
<213> ORGANISM: Artificial Sequence
<220> FEATURE:
<223> OTHER INFORMATION: Synthetic Peptide

<400> SEQUENCE: 19

Leu Pro Pro Ile Leu Val Tyr Ala Asp Cys Val Leu Ala Asn Trp Lys
1               5                   10                  15

Lys Lys Asp Pro Asn Lys
            20

<210> SEQ ID NO 20
<211> LENGTH: 22
<212> TYPE: PRT
<213> ORGANISM: Artificial Sequence
<220> FEATURE:
<223> OTHER INFORMATION: Synthetic Peptide

<400> SEQUENCE: 20

Leu Pro Pro Ile Leu Val Tyr Ala Asp Cys Val Leu Lys Ala Lys Asn
1               5                   10                  15

Asn Pro Trp Lys Lys Asp
            20

<210> SEQ ID NO 21
<211> LENGTH: 21
<212> TYPE: PRT
<213> ORGANISM: Artificial Sequence
<220> FEATURE:
<223> OTHER INFORMATION: Synthetic Peptide

<400> SEQUENCE: 21

Leu Cys Pro Asp Pro Ala Ile Val Leu Tyr Leu Ala Asn Trp Lys Lys
1               5                   10                  15

Lys Asp Pro Asn Lys
            20
```